(12) United States Patent
Yang et al.

(10) Patent No.: US 7,355,216 B2
(45) Date of Patent: Apr. 8, 2008

(54) FLUIDIC NANOTUBES AND DEVICES

(75) Inventors: Peidong Yang, Berkeley, CA (US); Rongrui He, El Cerrito, CA (US); Joshua Goldberger, Berkeley, CA (US); Rong Fan, El Cerrito, CA (US); Yiying Wu, Albany, CA (US); Deyu Li, Albany, CA (US); Arun Majumdar, Orinda, CA (US)

(73) Assignee: The Regents of the University of California, Oakland, CA (US)

( * ) Notice: Subject to any disclaimer, the term of this patent is extended or adjusted under 35 U.S.C. 154(b) by 227 days.

(21) Appl. No.: 10/822,148

(22) Filed: Apr. 8, 2004

(65) Prior Publication Data

US 2004/0262636 A1 Dec. 30, 2004

Related U.S. Application Data

(63) Continuation-in-part of application No. 10/731,745, filed on Dec. 8, 2003, now Pat. No. 7,211,143.

(60) Provisional application No. 60/461,346, filed on Apr. 8, 2003, provisional application No. 60/454,038, filed on Mar. 11, 2003, provisional application No. 60/432,104, filed on Dec. 9, 2002.

(51) Int. Cl.
*C30B 23/00* (2006.01)

(52) U.S. Cl. .................................. 257/200

(58) Field of Classification Search ................ 257/200
See application file for complete search history.

(56) References Cited

U.S. PATENT DOCUMENTS 6,113,722 A * 9/2000 Hoffman et al. ............ 156/155
6,613,875 B1 * 9/2003 Ghadiri ...................... 530/321
2002/0117659 A1 8/2002 Lieber et al.
2002/0130311 A1 9/2002 Lieber et al.
2002/0175408 A1 * 11/2002 Majumdar et al. .......... 257/734
2003/0165418 A1 9/2003 Ajayan et al.
2004/0005723 A1 1/2004 Empedocles et al.
2004/0076681 A1 * 4/2004 Dennis et al. ............... 424/489

OTHER PUBLICATIONS

"Heterostructures of ZnO—Zn coaxial nanocables and ZnO nanotubes," Wu et al., Appl. Phys. Lett., vol. 81 No. 7 (Aug. 12, 2002), pp. 1312-1314.*
"Formation of single crystalline ZnO nanotubes without catalysts and templates," Mensah et al., Appl. Phys. Lett., vol. 90 (Mar. 12, 2007), p. 113108.*

* cited by examiner

*Primary Examiner*—Thomas L. Dickey
(74) *Attorney, Agent, or Firm*—John P. O'Banion

(57) ABSTRACT

Fluidic nanotube devices are described in which a hydrophilic, non-carbon nanotube, has its ends fluidly coupled to reservoirs. Source and drain contacts are connected to opposing ends of the nanotube, or within each reservoir near the opening of the nanotube. The passage of molecular species can be sensed by measuring current flow (source-drain, ionic, or combination). The tube interior can be functionalized by joining binding molecules so that different molecular species can be sensed by detecting current changes. The nanotube may be a semiconductor, wherein a tubular transistor is formed. A gate electrode can be attached between source and drain to control current flow and ionic flow. By way of example an electrophoretic array embodiment is described, integrating MEMs switches. A variety of applications are described, such as: nanopores, nanocapillary devices, nanoelectrophoretic, DNA sequence detectors, immunosensors, thermoelectric devices, photonic devices, nanoscale fluidic bioseparators, imaging devices, and so forth.

18 Claims, 42 Drawing Sheets

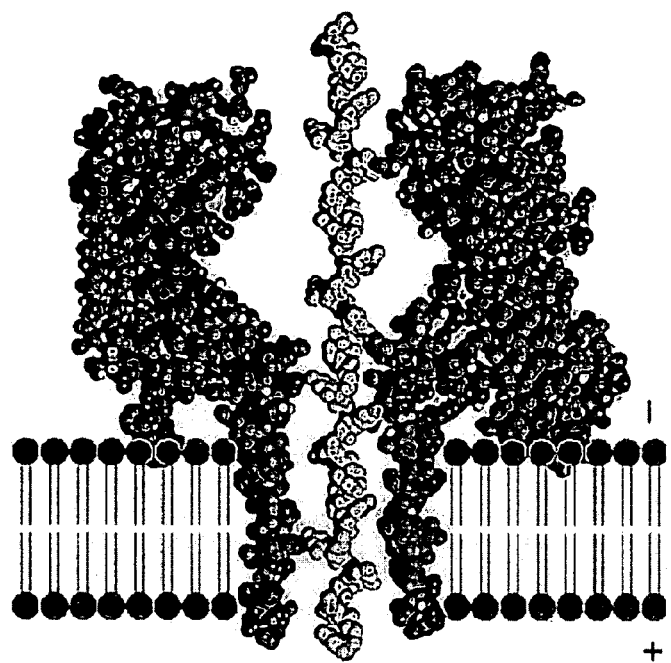
FIG. 1
(Prior Art)
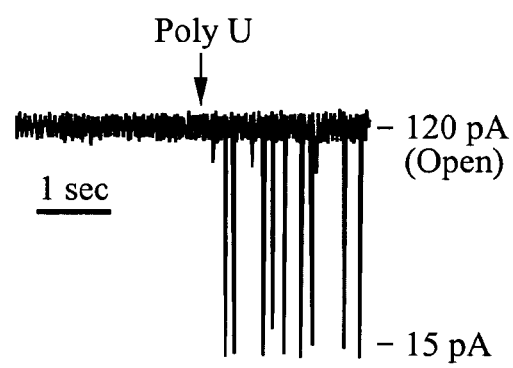
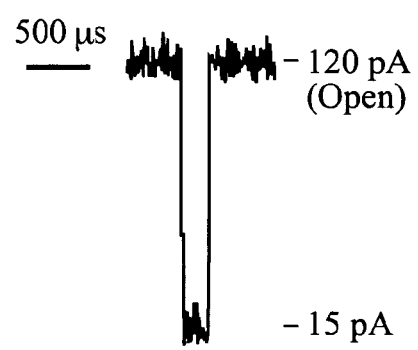
FIG. 2
(Prior Art)

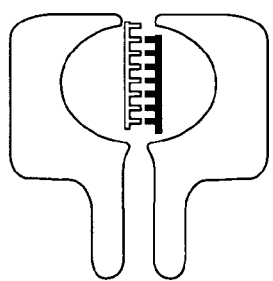
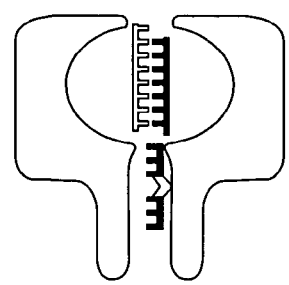
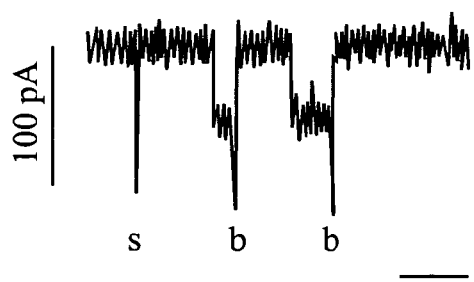
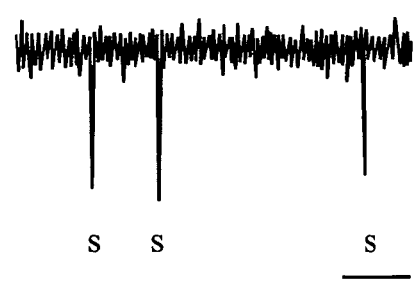
FIG. 3A
(Prior Art)
FIG. 3B
(Prior Art)

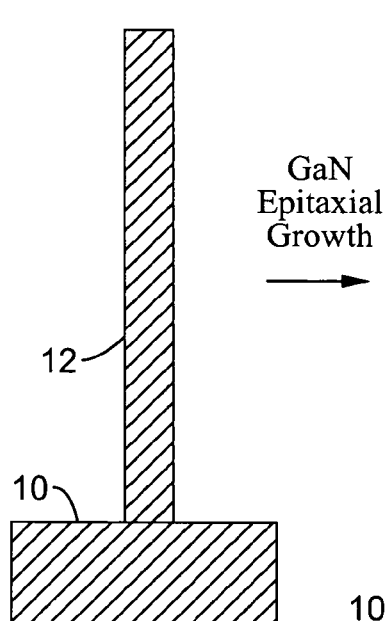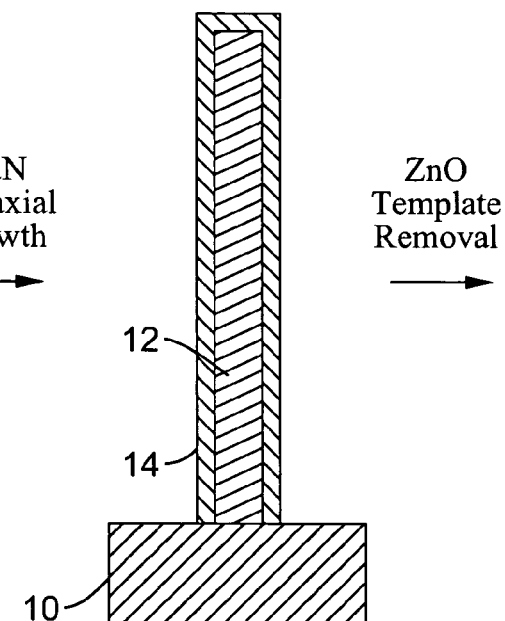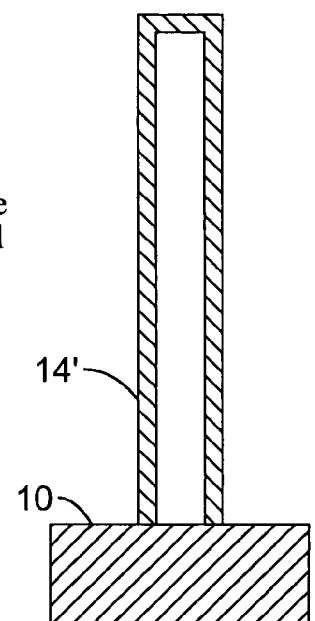
ZnO
Nanowire
FIG. 4A
GaN/ZnO
Core-sheath
Structure
FIG. 4B
GaN
Nanotubes
FIG. 4C

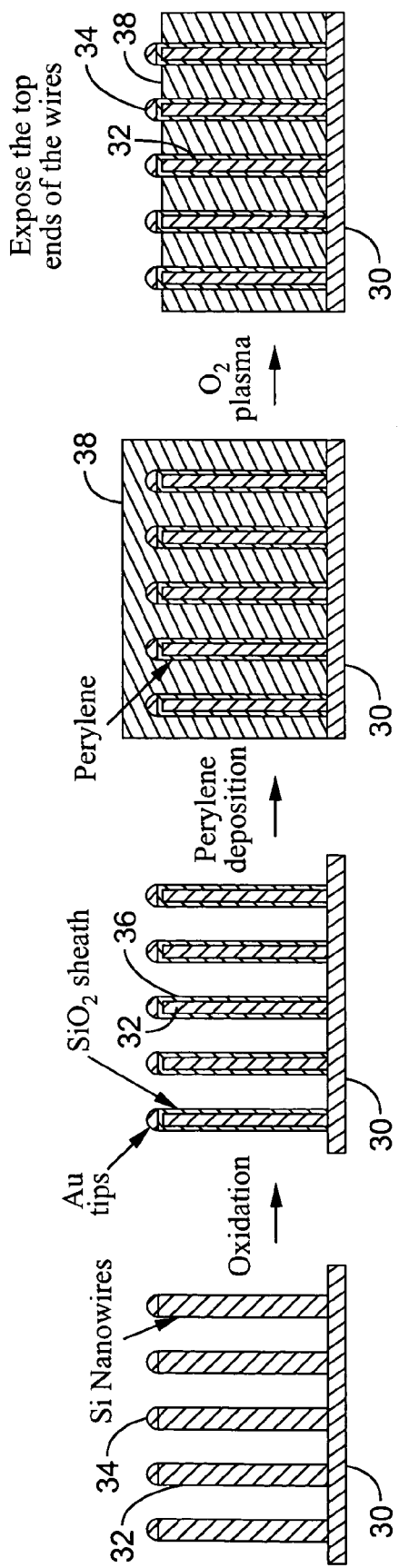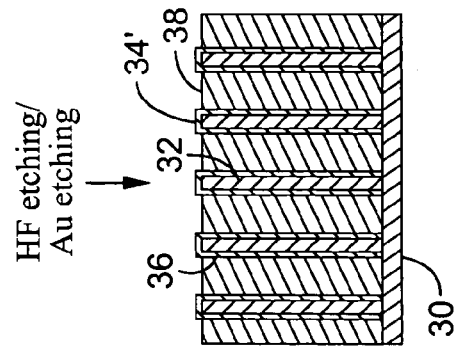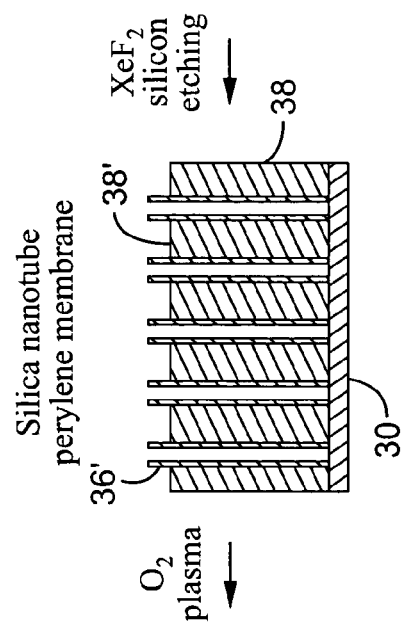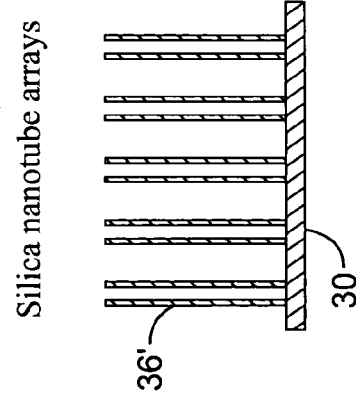

FLUIDIC NANOTUBES AND DEVICES

CROSS-REFERENCE TO RELATED APPLICATIONS

This application is a continuation-in-part of U.S. application Ser. No. 10/731,745 filed on Dec. 8, 2003 now U.S. Pat. No. 7,211,143, incorporated herein by reference in its entirety, which claims priority to U.S. provisional application Ser. No. 60/461,346 filed on Apr. 8, 2003, incorporated herein by reference in its entirety, U.S. provisional application Ser. No. 60/454,038 filed on Mar. 11, 2003, incorporated herein by reference in its entirety, and U.S. provisional application Ser. No. 60/432,104 filed on Dec. 9, 2002, incorporated herein by reference in its entirety.

This application also claims priority to U.S. provisional application Ser. No. 60/461,346 filed on Apr. 8, 2003, incorporated herein by reference in its entirety.

STATEMENT REGARDING FEDERALLY SPONSORED RESEARCH OR DEVELOPMENT

This invention was made with Government support under Contract No. DE-AC03-76SF00098, awarded by the Department of Energy and Grant No. DMR-0092086, awarded by the National Science Foundation. The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to fluidic devices, and more particularly, to fluidic nanotubes and devices fabricated therefrom.

2. Description of Related Art

Sensors utilizing novel nanostructured materials and new mechanisms offer to significant impact a broad range of applications relating to national security, health care, the environment, energy, food safety, and manufacturing. Emerging micro- and nano-technologies can decrease the size, weight and cost of sensors and sensor arrays by orders of magnitude, and increase their spatial and temporal resolution and accuracy.

There are urgent civilian and military needs at this moment for new sensors and sensor systems which include: (1) the ability to respond to new toxic chemicals, explosives and biological agents, (2) providing enhanced sensitivity, selectivity, speed, robustness, and immunity from false alarms, and (3) the ability to function, perhaps autonomously, in unusually complex environments (NSF 03-512). In this regard, the design and synthesis of functionalized nanostructured materials and development of new sensing mechanisms could play a significant role in the process of developing efficient chemical and biological sensors.

In general, ideal nanostructured materials would have some degree of porosity/high surface area with suitable analyte interaction mechanism employing various sensing principles such as mechanical, chemical, electrical, chromatographic, biological, fluidic, optical, and mass sensing.

Since the discovery of carbon nanotubes in 1991, there have been significant research efforts devoted to nanoscale tubular forms of various solids. The formation of a tubular nanostructure generally requires a layered or anisotropic crystal structure. There are reports of nanotube formation of solids lacking layered crystal structures such as silica, alumina, silicon and metals through templating of carbon nanotubes and porous membranes or thin film rolling. Such nanotubes, however, are either amorphous, polycrystalline or exist only in ultra high vacuum.

Hollow inorganic nanotubes are attracting a great deal of attention due to their fundamental significance and potential applications in bioanalysis and catalysis. Among them, silica nanotubes are of special interest because of their hydrophilic nature, easy colloidal suspension formation, and surface functionalization accessibility for both inner and outer walls. Such modified silica nanotubes and nanotube membrane have shown potential applications for bioseparation and biocatalysis. Recently, bright visible photoluminescence from sol-gel template synthesized silica nanotubes was observed. In addition, the study of the physical and chemical nature of molecules or ions confined within the inorganic nanotubes is of great current interest.

Silica nanotubes have been synthesized typically within the pores of porous alumina membrane templates using a sol-gel coating technique. Alumina templates can be dissolved to liberate single silica nanotubes. Such nanotubes, which are prepared at low temperature, have porous walls and are relatively fragile. Once the templates are removed, the silica nanotubes will generally bundle up and become less oriented. The same applies to the silica nanotubes prepared at low-temperature using other templates.

Over the years, various molecular detection techniques have been developed for their chemical/biological sensing, diagnostic and prognostic utility. For most, efficiency is a result of a trade-off between sensitivity, specificity, ease of operation, cost, speed and immunity to false alarms. Novel functional materials such as quantum dots, photonic crystals, nanowires, carbon nanotubes, porous membranes, porous silicon and sol-gel matrices incorporating biomolecules have been used as sensing elements with various possible detection mechanisms. For example, the use of quantum dots has been demonstrated as fluorescent biological labels with several advantages over traditional organic dyes. Major advantages of this approach are the high extinction coefficient, bright wavelength-tunable fluorescence and superior photostability of the quantum dots. Metal nanoparticles have also been utilized for various biological sensing applications with significant enhanced sensitivity and specificity. The ability of porous silicon to display well-resolved Fabry-Perot fringes for biosensing applications has been utilized in this regard, and molecular imprinted sol-gel process for biosensing has been recently developed. In addition, a new sensing scheme has been developed using swellable photonic crystals as active components.

In addition to these efforts, one-dimensional nanostructures (nanotubes and nanowires) have recently received significant attention as possible miniaturized chemical and biological sensing elements. The ultrahigh surface to volume ratios of these structures make their electrical properties extremely sensitive to surface-adsorbed species, as recent work has shown with carbon nanotubes, functionalized silicon nanowires and metal nanowires.

Chemical and biological nanosensors are interesting because of their potential for detecting very low concentrations of biomolecules or pollutants on platforms small enough to be used in vivo or on a microchip. For example, a room temperature photochemical $NO_2$ sensor has recently been demonstrated based on individual single-crystalline oxide nanowires and nanoribbons. Regardless of their nanotube or nanowire morphologies, the sensing mechanism generally used in these studies is the electron-transfer process between the analytes (in solution or gas) and the nanostructures, thus inducing conductivity changes. It has been demonstrated in the field that for metal nanowire sensing, different mechanisms have to be invoked on the metal nanowires. These one dimensional nanostructures generally provide excellent sensitivity due to having an inherent high surface to volume ratio. However, the sensing selectivity for these structures has been less than ideal, although in many cases this can be improved by surface functionalization of specific receptors.

Chemical/sensing systems are being studied using silica and gold tubular membranes. These membranes represent a new class of molecular sieves for molecular separation and electrochemical sensing based on the size of the molecules as well as interaction with the tubes surface functional group. In most of these studies, the inorganic nanotube membrane (polycarbonate or porous alumina) was set up to separate two salt solutions and a constant transmembrane potential was applied, then the transmembrane current was measured. When an analyte of comparable dimensions to the tube diameter was added to one of the solutions, a decrease in transmembrane current was sensed because of the current blocking by the molecules. Using such schemes, ultratrace of different ions and molecules were detected. These experiments, however, have all relied on using entire membranes as sensing elements. No significant efforts have been placed on single tube sensing, although the use of single nanotube sensing would obviously represent the miniaturization limit.

It is also worth noting that recently developed artificial nanopores have been fabricated using soft lithography or ion mill to carry out molecular sensing through individual nanotubes. These processes are subject to the problem of scaling up or the pore size limitation (i.e. 200 nm for the PDMS approach). The use of carbon nanotubes for this type of nanofluidic sensing applications has also been proposed. A number of significant technical hurdles, however, need to be overcome before these can become a viable nanofluidic sensing element. Examples of these hurdles include: the difficulty of surface functionality (both internally and externally), and the difficulty associated with control over the metallic tube versus semiconductor tubes.

Capillary Electrophoresis (CE) is a technique similar to gel electrophoresis with an added advantage of smaller sample consumption (<10 nL), automation, faster analysis and integration with an on-line detection system. The high surface to volume ratio of the capillary allows the application of high voltage to achieve fast separation with efficient heat dissipation to prevent band-broadening effects. The ends of the capillary are in contact with reservoirs filled with the electrolyte, where electrical potential can be applied through non-reactive electrodes. UV absorbance, laser induced fluorescence and electrochemical detections (e.g. potentiometric) can be used on-line for detection of separated molecules in CE. The application of CE to detect sialic acids in serum as a tumor marker has been demonstrated. Even though the cost per run for CE is low, the initial cost of instrumentation and detection systems can be prohibitive.

FIG. 1 and FIG. 2 illustrate a 120 mV bias across an $\alpha$ HL ion channel which produces an ionic current of ≈120 pA. When a single polynucleotide strand passes through the channel, the current drops to 15-50 pA. The amplitude of the current drop and its duration depend on the type of nucleotide.

Previous work on nanopore based single molecule detection can be broadly classified into two categories, namely: (i) non-functionalized nanopores; (ii) functionalized nanopores. Almost all of the prior work has involved the transmembrane protein ion channel $\alpha$-Hemolysin ($\alpha$ HL) embedded in a suspended membrane separating two chambers filled with ionic solution. The entrance on the top (cis) side is about 2.6 nm in diameter whereas the narrow channel through the membrane that is closer to the bottom end (trans) is 1.4 nm in diameter. When a voltage bias of 120 mV is applied across the ion channel, an ionic current of about 120 pA is produced for ionic concentrations of 1 MKCl (the resistance is approximately $10^9$ $\Omega$).

When single-stranded polynucleotides are introduced in one of the chambers, they electrophoretically flow through the ion channel. By doing so, they block the ionic current, which reduces to levels of 15-50 pA as seen in FIG. 2. The time of flight of these polynucleotides seems to vary linearly with their length, and inversely with the applied voltage. It has been hypothesized that different nucleotides would have different blocking signatures (either time of flight or amplitude of current drop), which would allow one to rapidly sequence ssDNA directly. This has led to many attempts over the last decade, and there has been partial success in discriminating between different bases. For example, polycs seem to produce shorter but deeper (lower current) decrease in ionic current whereas polyAs produce longer but shallower reductions. However, direct and rapid sequencing of ssDNA has been unsuccessful and remains a challenge, although hairpin DNA molecules have been detected with single nucleotide resolution.

One of the problems in direct sequencing arises from the fact that the time a single base spends in the nanopore is too short and that the number of ions that it blocks is too few (i.e. approximately 100), making it difficult to detect it above the background noise. Slowing down the polynucleotides could offer a chance of direct sequencing, but that has also remained a challenge. More recently, artificial nanopores have been demonstrated that can be fabricated from inorganic materials, and that show similar behavior in blocking ionic current when ssDNA passes through them. However, direct sequencing of ssDNA has not been reported so far and parallel processing of those artificial nanopores has proven to be very difficult with this approach.

While it has so far been very difficult to achieve biomolecule specificity using non-functionalized nanopores, recent work of using functionalized $\alpha$ HL nanopores has shown promise. Nanopores have been functionalized using a ssDNA probe attached at the cis entrance through a disulphide linkage to a cysteine residue in the $\alpha$ HL protein.

FIG. 3A and FIG. 3B illustrate a probe ssDNA which is attached through a disulphide linkage to a cysteine residue at the cis opening of a α HL nanopore protein as schematically shown in the upper portions of FIG. 3A and FIG. 3B. The lower halves of FIG. 3A and FIG. 3B depict time traces of the ionic current passing through the nanopore. If the complementary target ssDNA is transported through the nanopore as shown in FIG. 3A, it binds with the probe strand which reduces the ionic current for approximately 50 mS. However, if a single base pair mismatch is introduced as shown in FIG. 3B, the binding lifetime is reduced to about 1 mS.

Then by transporting target ssDNA sequences, they found that when the target was fully complementary, its residence time in the nanopore, as measured by the duration of the reduced ionic current, was much longer ($\approx$50 mS) than if even a single base-pair mismatch is introduced ($\approx$1 mS). From this, kinetics of the binding reaction can be quantified. Furthermore, the α HL protein nanopore has been functionalized with other molecules to study reaction kinetics of various molecular interactions such as small molecules with proteins, ions with proteins, and so forth. The use of functionalized nanopores for biomolecular analysis could yield a number of benefits, however, such efforts have met with fabrication difficulties.

Therefore, a need exists for nanofluidic devices and nanotube structures which can be readily implemented, such as within fluidic sensing applications. The present invention fulfills those needs and others, while overcoming the drawbacks inherent in prior nanodevice and nanostructure approaches.

BRIEF SUMMARY OF THE INVENTION

The present invention pertains to fluidic nanotubes and devices fabricated from fluidic nanotubes. The fabrication of oriented, robust nanotube arrays is of interest for their potential use in nanoscale fluidic bioseparation, sensing, catalysis, and so forth. Sensors utilizing novel nanostructured materials and new mechanisms may significantly benefit a broad range of applications relating to national security, health care, the environment, energy, food safety, and manufacturing. Emerging micro- and nano-technologies can decrease the size, weight and cost of sensors and sensor arrays by orders of magnitude, and increase their spatial and temporal resolution and accuracy.

Over the years, various molecular detection techniques have been developed and validated for their chemical/biological sensing, diagnostic and prognostic utility. For most, efficiency is a result of a trade-off between sensitivity, specificity, ease of operation, cost, speed and few false alarms. Novel functional materials such as quantum dots, photonic crystals, nanowires, carbon nanotubes, porous membranes, porous silicon and sol-gel matrices incorporating biomolecules have been used as sensing elements with various possible detection mechanisms. In addition, the growth of nanotubes would be advantageous in potential nanoscale electronics, optoelectronics, and biochemical sensing applications.

It will be appreciated that a cornerstone of devices fabricated from fluidic nanotubes are the nanotubes themselves. While nanotubes can be fabricated according to various methods and have various compositions of matter, an aspect of the present invention is to form a nanotube using a sacrificial core. In such a process, the nanotube is formed around the core and then the core is removed.

Another aspect of the invention is the fabrication of a fluidic nanotube that is non-carbon-based. While fluidic devices can be made using carbon-based nanotubes, such nanotubes are generally hydrophobic and may be unsuitable for fluidic applications without modification. A further aspect of the invention is the fabrication of a non-carbon-based nanotube that is non-porous (e.g., having a seamless tube wall) for use in fluidic applications.

One aspect of the invention is an "epitaxial casting" method for the synthesis of single crystalline nanotubes. In one embodiment, nanotubes with inner diameters of 30-200 nm and wall thicknesses of 5-50 nm are fabricated using hexagonal ZnO nanowires as templates for the epitaxial overgrowth of thin GaN layers in a chemical vapor deposition system. The ZnO nanowire templates are subsequently removed by simple thermal reduction and evaporation, resulting in ordered arrays of GaN nanotubes on the substrates. In another embodiment, single nanotubes or random samples can be formed as an alternative to forming the nanotubes in an ordered array. In addition to GaN as the nanotube material, other semiconductor materials can be used such as Si, GaAs, CdSe, GaP, InP, Ge, and InAs. The nanowire material can be selected from Groups II, III, IV, V, VI, etc. and can include quaternaries and tertiaries, as well as oxides.

According to another aspect of the invention, nanotubes are fabricated using thermal oxidation and etching. In one embodiment, silicon nanowire arrays are used as templates. The process starts with thermal oxidation of the Si nanowire arrays which results in arrays of thin Si nanowires sheathed by a thick layer of silicon oxide. This oxidized nanowire array is then selectively etched with $XeF_2$ to remove the silicon nanowire cores, leaving an array of ordered silicon dioxide nanotubes with controllable inner diameters. The inner diameters are controlled by the initial diameters of the silicon nanowires and the thermal oxidation process. In another embodiment, single nanotubes or random samples can be formed as an alternative to forming the nanotubes in an array. Other nanotube compositions can be fabricated in this manner as well, including, but not limited to, GaO, InO and other oxides and insulating materials.

A number of nanofluidic devices are described, which can be fabricated from conventional nanotubes, but are more preferably fabricated from nanotube structures which are formed according to the aspects of the present invention. By way of example, and not of limitation, a class of devices fabricated from fluidic nanotubes includes a nanofluidic transistor formed from a semiconductor nanotube and having source and drain connections, and optional gate electrode along the length of the nanotube. By way of example another class of devices fabricated from fluidic nanotubes, which have been functionalized, comprises electrophoretic devices formed from insulating or semiconducting nanotubes, and having source and drain electrodes within the reservoirs proximal to each open end of the nanotubes.

From these classes of fluidic devices, separately or in combination, numerous fluidic devices can be implemented, which include but are not limited to, nanocapillary devices, field effect transistors, nanoelectrophoretic devices, detectors, DNA sequence detectors, immunosensors, tube-field-effect transistors, microfluidic wafers, nanocapillary wafers, electrode wafers, MEMS switching chips, transistors, sensors, thermoelectric devices, photonic devices, nanoelectromechanical actuators, nanoelectromechanical sensors, and imaging devices. It will be appreciated that the devices described herein are based on the use of fluidic nanotubes in general; that is, their fabrication need not be based on a specific composition of nanotube but on the use of a fluidic nanotube.

By way of example, aspects of the invention include the description of nanocapillary electrophoresis array technology (NEAT) and tube field effect transistor (TFET) as platforms for ultrasensitive (down to single molecular level) chemical and biological sensors with high specificity.

In one embodiment, NEAT/TFET is based on the use of nanocapillaries 5-20 nm in diameter and made of silicon dioxide ($SiO_2$) or semiconductor gallium nitride (GaN). The inner surface of these nanocapillaries will be functionalized by probe/receptor ligands. A mixture of biomolecules in an ionic solution will be electrophoretically transported through the nanocapillary while the ionic current or the conductivity of the semiconductor tube is monitored. If a target ligand specifically binds to the probe molecules attached to the wall, the residence time of the ligand inside the nanocapillary will be much longer than that for non-binding molecules passing through it. Because the nanocapillaries are on the order of molecular size (5-20 nm diameter), the ionic current will be modulated by the presence or absence of specifically-bound ligands as well as the molecule size. In addition, if there is any charge transfer between the analytes and the semiconductor GaN nanotubes, the conductivity of the tubes can be modified and monitored accordingly. Multiple electrical signals (ionic current and source-drain current) and optical signatures can be used simultaneously for the sensing purposes. In addition, parallel processing and integration of nanocapillary arrays can be used for fabrication of nanofluidic chips for multiplexed chemical and biological sensing. The invention facilitates chemical and biological sensors with fast response, ultrasensitivity, high specificity and few false alarms.

The embodiments of the present invention generally describe a fluidic nanotube which comprises: a tubular member formed from a non-carbon, hydrophilic material (insulating or semiconducting) wherein the nanotube is a functional component of an electrical device. The tubular member (nanotube) has first and second ends and a non-porous inner bore, preferably seamless, between said first and second ends. The functional component could be any of the following nanocapillary devices, field effect transistors, nanoelectrophoretic devices, detectors, DNA sequence detectors, immunosensors, tube-field-effect transistors, microfluidic wafers, nanocapillary wafers, electrode wafers, MEMS switching chips, sensors, thermoelectric devices, photonic devices, nanoelectromechanical actuators, nanoelectromechanical sensors, nanoscale fluidic bioseparators, imaging devices, and combinations thereof.

In one embodiment the nanotube is formed in a sacrificial process wherein a sheath of nanotube material, preferably single-crystalline, is deposited over a nanowire and then the core material is removed. The core material can comprise any material selected from the group of materials consisting essentially of zinc oxide (ZnO), silicon (Si), gallium nitride (GaN), germanium (Ge), silver (Ag), gold (Au), group II-VI materials, group III-V materials, elemental group IV materials, and metals. The material from which the nanotube sheath is formed comprises a material selected from the group of materials consisting essentially of GaN, Si, GaAs, CdSe, GaP, InP, Ge, InAs, Group II, III, IV, V, and VI materials including quaternaries and tertiaries, as well as oxides, SiO, GaO, InO and other insulating materials, elemental metals, and polymers. The material selected for the nanotube material has a sufficiently similar crystalline structure and lattice constant as the material selected for the core material, which allows growth of the nanotube material on the core material.

The present invention has an embodiment which may be generally described as a tubular field effect transistor (TFET), comprising: (a) at least one semiconducting nanotube; (b) a reservoir fluidly coupled to each end of the nanotube; (c) a source electrode attached to a first end of the nanotube; and (d) a drain electrode attached to a second end of the nanotube; (e) wherein the passage of molecular species through the nanotube changes source to drain current flow through the nanotube.

The TFET device may further comprise capture molecules retained within the nanotube for capturing or slowing select molecular species. The TFET may also further comprise a gate electrode attached toward the center of the nanotube for controlling ion transport through the nanotube.

The present invention has another embodiment which may be generally described as a nanocapillary electrophoresis device, comprising: (a) at least one hydrophilic nanotube; (b) a plurality of capture molecules retained within the nanotube for capturing or slowing selected molecular species; (c) a reservoir fluidly coupled to each end of the nanotube; (d) a source electrode coupled proximal a first end of the nanotube; and (e) a drain electrode coupled proximal a second end of the nanotube; (f) wherein the passage of molecular species through said nanotube changes ionic current flow.

The electrical sensing of movement through the electrophoresis device can be augmented with conventional sensing for reducing false positives. One embodiment therefore includes: (a) an optical single-molecule detection and identification system configured for generating an optical detection signal in response to molecules passing through the nanotube; and (b) a coincidence circuit configured to generate coincident molecule detection signals in response to the coincidence between the ionic current flow and the optical detection signal.

The electrophoretic device may be constructed as a cell within an electrophoretic device array, one class of devices is embodied as nanocapillary electrophoresis array technology (NEAT). An embodiment of the neat device can be generally described as: (a) a hydrophilic nanotube; (b) a plurality of capture molecules retained within the nanotube for capturing or slowing selected molecular species; (c) a reservoir fluidly coupled to each end of the nanotube; (d) a source electrode coupled proximal a first end of the nanotube; (e) a drain electrode coupled proximal a second end of the nanotube; (f) wherein the passage of molecular species through said nanotube changes ionic current flow; (g) wherein the above structures comprise an electrophoresis cell; (h) an array of said electrophoresis cells; and (i) means for detecting the current from each of said electrophoresis cells.

The detecting means can comprise for example: (a) a plurality of switching elements configured for selecting one or more of the electrophoresis cells in the array; and (b) a circuit for conditioning the signals received from each of the electrophoresis cells, such as analog amplifiers. In one embodiment the switching elements comprise MEMs switches to sufficiently limit off-state leakage. In an embodiment of a two dimensional array of electrophoretic cells, the switching devices are shown arranged in a row and column format to allow measuring determining I-V for any cell.

The present application therefore describes numerous inventive aspects, including but not limited to the following.

An aspect of the invention is to provide devices for use in fluidic measurement and control systems.

Another aspect of the invention is to provide nanotube based fluidic sensing and control devices.

Another aspect of the invention is to provide devices that contain $SiO_2$ nanocapillaries with diameters below 20 nm and lengths 1-10 µm.

Another aspect of the invention is to provide devices in which the nanocapillaries can be integrated within a microfluidic system to provide fluidic access to both sides.

Another aspect of the invention is to provide electronic controls for applying voltage biases (0.1-1 V) across the nanocapillary, for the measuring of ionic currents down to the 1 pA range.

Another aspect of the invention provides devices for quantitative measurement of specificity and sensitivity of chemical and biological species.

Another aspect of the invention provides functionalized nanocapillaries by immobilizing receptor biomolecules on the inner surface of the nanocapillaries through covalent linkages.

Another aspect of the invention is to provide detection of ionic and sources-drain current within a nanotube-based device and test for specificity and sensitivity of receptor-ligand binding by monitoring modulation of the ionic current.

Another aspect of the invention is to provide quantitative measurements of ionic (NEAT) current and source-drain current (TFET) current as a function of analyte concentration, analyte exposure time, and ambient conditions (temperature and pH).

Another aspect of the invention is to provide for single molecular level optical imaging within individual nanofluidic systems.

Another aspect of the invention is to provide means for parallel processing and integration of nanocapillary arrays for multiplexed chemical and biological sensing Another aspect of the invention is to address the goals of NSF-Sensor network of developing innovative technologies to enable efficient detection and profiling of molecular changes through cross-disciplinary interactions between chemistry, engineering, semiconductor processing, statistical physics, and electronics.

Another aspect of the invention is to provide a new paradigm (NEAT/TFET) for molecular analysis for chemical and biological molecules.

Another aspect of the invention is a fabrication process for making an array of nanocapillaries that are monolithically integrated with a silicon wafer.

Another aspect of the invention is to design a chip containing microfluidics for functionalization and I/O for individual nanocapillaries.

Another aspect of the invention is to design a counter-electrode wafer.

Another aspect of the invention is to integrate multiple wafers (i.e. three wafers) to make a nanotubular electrophoresis array chip.

Another aspect of the invention is to fabricate a MEMS switching chip for connection to the NEAT chip.

A still further aspect of the invention is to establish a nanocapillary electrophoresis database containing various chemical and biological molecules.

Another aspect of the invention is to provide a common sensing platform for health, environment and battlefield applications, while emphasizing high sensitivity, high specificity, cost effectiveness, and user friendliness.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1 is a schematic of a conventional α HL ion channel shown embedded in a suspended membrane separating two chambers.

FIG. 2 is a plot of current flow in response to the passage of a polynucleotide strand through the ion channel of FIG. 1.

FIG. 3A-3B are schematics of conventional ssDNA probes attached through a disulphide linkage to a cysteine residue at the opening of a α HL nanopore protein.

FIG. 4A-4C are cross section views of the epitaxial casting process for fabricating nanotubes according to an embodiment of the present invention, showing GaN nanotubes formed over ZnO nanowires.

FIG. 10 is an image of nanotubes formed according to an embodiment of the present invention and shown end-on.

FIG. 18A-18G are steps in forming $SiO_2$ nanotubes according to an embodiment of the present invention, shown with parylene deposition stages during etching.

DETAILED DESCRIPTION OF THE INVENTION

Figure 55:
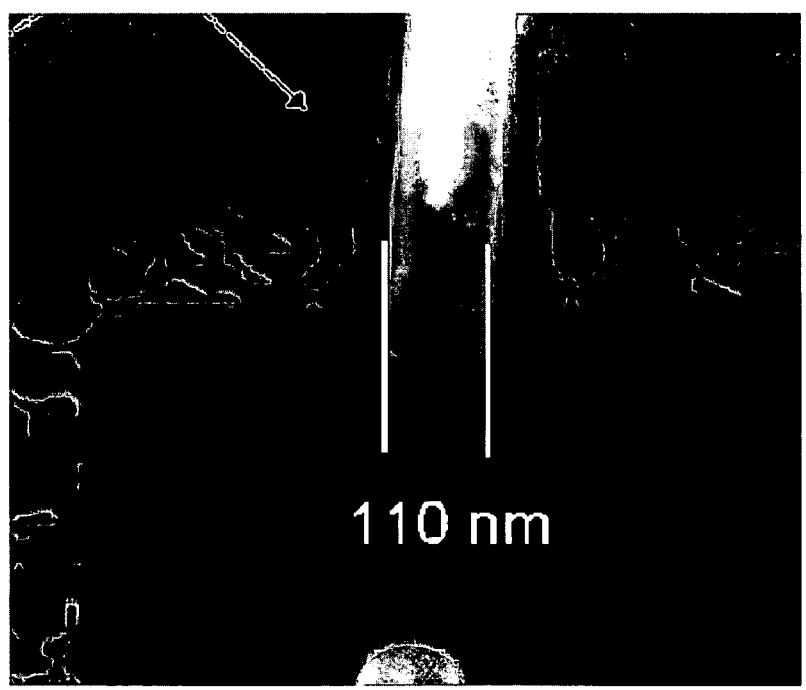

Referring more specifically to the drawings, for illustrative purposes the present invention is embodied in the apparatus generally shown in FIG. 4A through FIG. 55. It will be appreciated that the apparatus may vary as to configuration and as to details of the parts, and that the method may vary as to the specific steps and sequence, without departing from the basic concepts as disclosed herein.

A number of electronic devices can be implemented utilizing nanotube structures, in particular fluidic nanotubes. By way of example tubular field effect transistors and nanocapillary electrophoresis devices are described which can provide a number of benefits within a variety of fields. First, novel methods are described for fabricating nanotubes which may be utilized in these nanotube devices.

In accordance with the present invention, a nanotube is formed by creating at least one sheath layer around a nanowire template. The nanowire template functions as a sacrificial core which is later removed to establish the central opening through the nanotube. Once the sacrificial core is removed, the nanotube can be used in any conventional manner.

By way of example, and not of limitation, two embodiments of a method of fabricating nanotubes using a sacrificial core in accordance with the present invention will be described. It will be appreciated, however, that the invention contemplates any method in which a sacrificial core is used as a template for nanotube fabrication. In a first embodiment, a layer of material such as gallium nitride (GaN) is epitaxially grown on the exterior of a nanowire core, such as zinc oxide (ZnO), followed by removal of the nanowire core. In a second embodiment, a nanowire core such as silicon (Si) is oxidized to form an $SiO_2$ sheath layer, and then the nanowire core is removed to leave the oxide sheath.

Epitaxial Casting Method

FIG. 4A through FIG. 4C illustrate the general steps in what we refer to as an "epitaxial casting" approach. FIG. 4A depicts a substrate 10 upon which a nanowire 12 is being formed, preferably a single-crystalline nanowire. FIG. 4B depicts depositing a preferably single-crystalline sheath 14 over nanowire 12. FIG. 4C depicts removing the nanowire template (core) 12 thereby forming a nanotube 14'.

In one embodiment, the nanowires 12, such as prefabricated hexagonal-shaped single-crystalline nanowires (preferably ZnO) are employed as templates for tubular deposition of a material, such as GaN. Since ZnO and GaN both have wurtzite crystal structures and have similar lattice constants (ZnO: a=3.249 Å, c=5.207 Å; GaN: a=3.189 Å, c=5.185 Å), GaN can grow epitaxially on the side {110} planes of these ZnO nanocylinders and form a thin GaN layer that is single-crystalline in nature. It will be appreciated that many combinations of materials have sufficiently similar crystalline structures and lattice constants to allow epitaxial growth of the sheath material on the nanowire material.

In FIG. 4B, once the ZnO nanocylinders are coated with a thin GaN sheath 14, the template 12 (FIG. 4A) is subsequently removed, such as by thermal processes, leaving a GaN nanotube 14'. By way of example and not of limitation, two possible mechanisms for the removal of ZnO templates can be employed.

In one approach, ZnO is chemically etched by ammonia ($NH_3$) at high temperature. In FIG. 4C, prolonged heating of samples after GaN coating in ammonia ($NH_3$) readily yields pure GaN nanotubes.

Another approach is to utilize a thermal reduction process at high temperatures (e.g. 600° C. in hydrogen gas, $H_2$). The single-crystalline wurtzite GaN nanotubes here differ fundamentally from theoretically simulated GaN nanotubes, where a metastable graphitic GaN structure was proposed.

EXAMPLE 1

The nanowire cores employed in the present invention can be formed in any conventional manner. For example, arrays of zinc oxide (ZnO) nanowires were grown on a substrate material, such as (110) sapphire wafers, preferably using a vapor deposition process. These ZnO nanowire arrays were placed inside a reaction tube (i.e. MOCVD reaction tube) for GaN chemical vapor deposition. Trimethylgallium and ammonia were used as precursors and fed into the system with argon or nitrogen carrier gas. The deposition temperature was preferably set at 600° C. to 700° C.

After the GaN deposition, the samples were treated in a hydrogen atmosphere at elevated temperature, such as 600° C. with 10% $H_2$ in argon, for removing the ZnO nanowire templates. It should be appreciated that other methods and materials may be utilized (although in some instances less preferably) for forming the nanowires, covering the nanowires with the nanotube material, and for sacrificially removing the nanowire material (in select applications only a portion of the nanowire material need be removed according to the present invention).

Figure 5A:
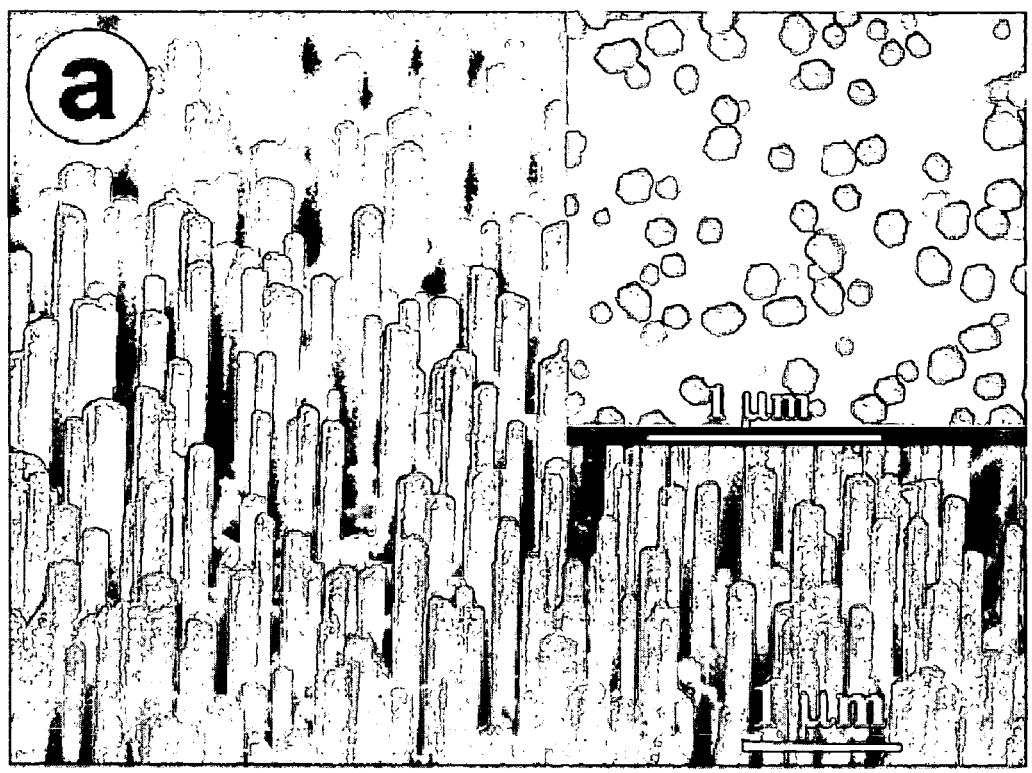
FIG. 5A is an image of a nanowire template array according to an aspect of the present invention fabricated from ZnO, showing in an inset the cross-sections of the nanowire array.

FIG. 5A shows a scanning electron microscopy (SEM) image of the starting ZnO nanowire array templates, which were found to have uniform lengths, such as in the range of from 2-5 μm, and each having a uniform diameter with diameters within the array of nanowires ranging from 30-200 nm. The nanowires are well-facetted as seen in the inset of FIG. 5A with hexagonal cross-sections, exhibiting {110} planes on the sides. After the GaN deposition and template removal to form the nanotubes, the color of the sample had shifted from white to yellowish or darker.

Figure 5B:
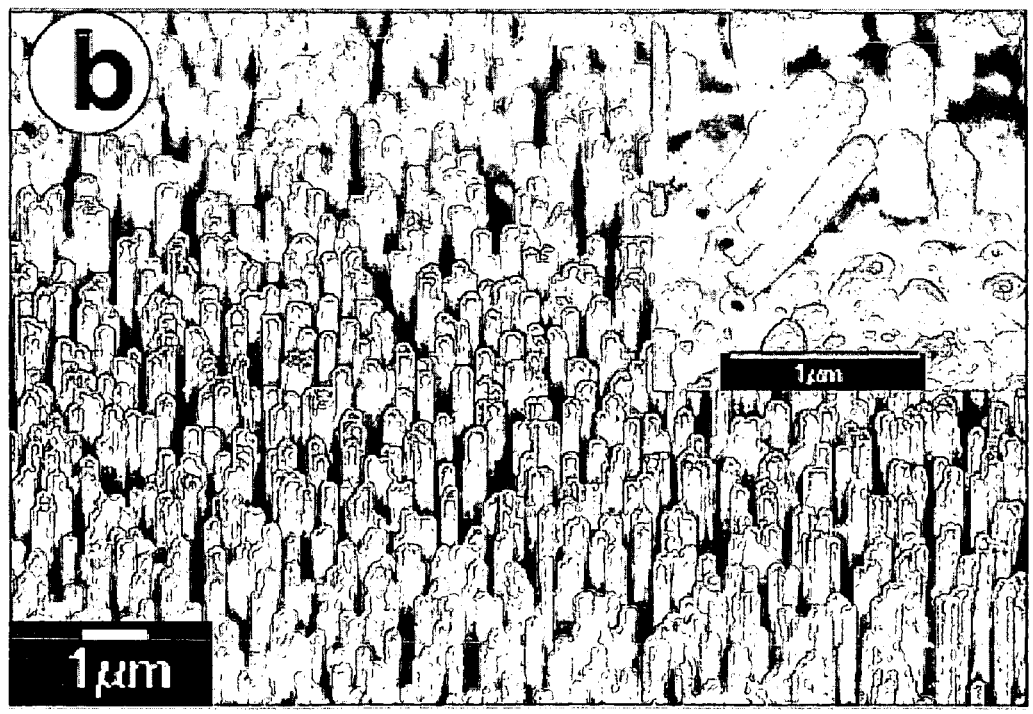
FIG. 5B is an image of a nanotube array formed over the sacrificial nanowire array of FIG. 5A according to an aspect of the present invention fabricated from GaN, shown in an inset is the fractured interface between the GaN nanotubes and the substrates.

FIG. 5B is an example image illustrating that the morphology of the initial nanowire arrays was maintained in the nanotubes, except for the increase in the diameters of the resulting nanostructures. The nanostructures appear less facetted compared with the original ZnO nanowire templates. Compositional analysis on the final product shows only a relatively minor Zn signal.

Figure 6:
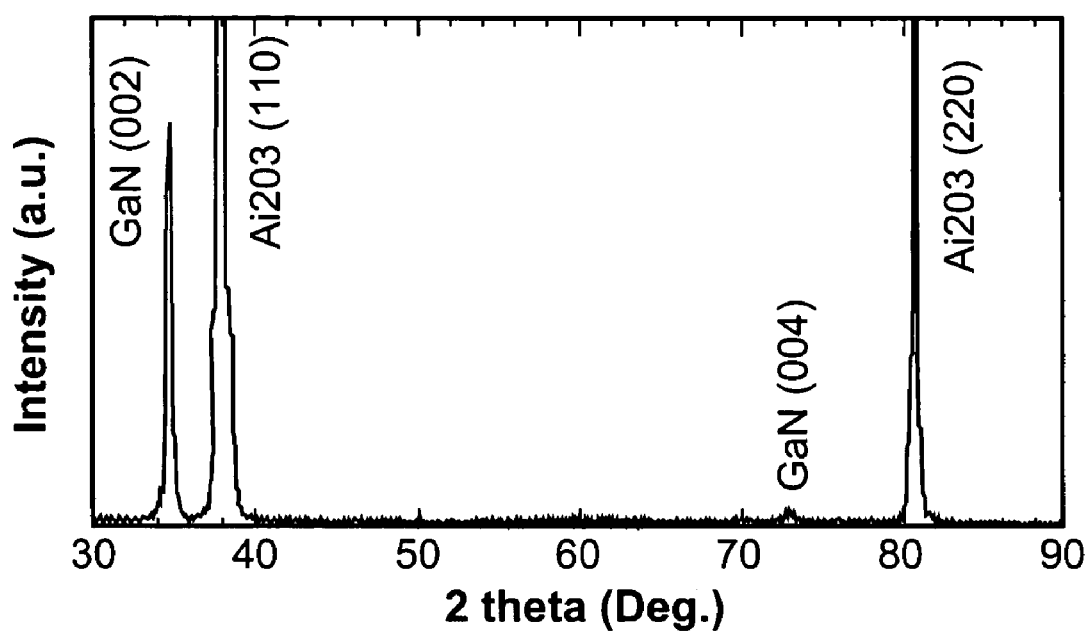
FIG. 6 is a plot of diffraction of the GaN nanotube array of FIG. 5B according to an aspect of the present invention, showing nanotube composition.

FIG. 6 illustrates the result of X-ray diffraction (XRD) on the sample which shows only (00l) diffraction peaks of the wurtzite GaN structure indicative of excellent epitaxy/texturing for the GaN coating.

Figure 7A:
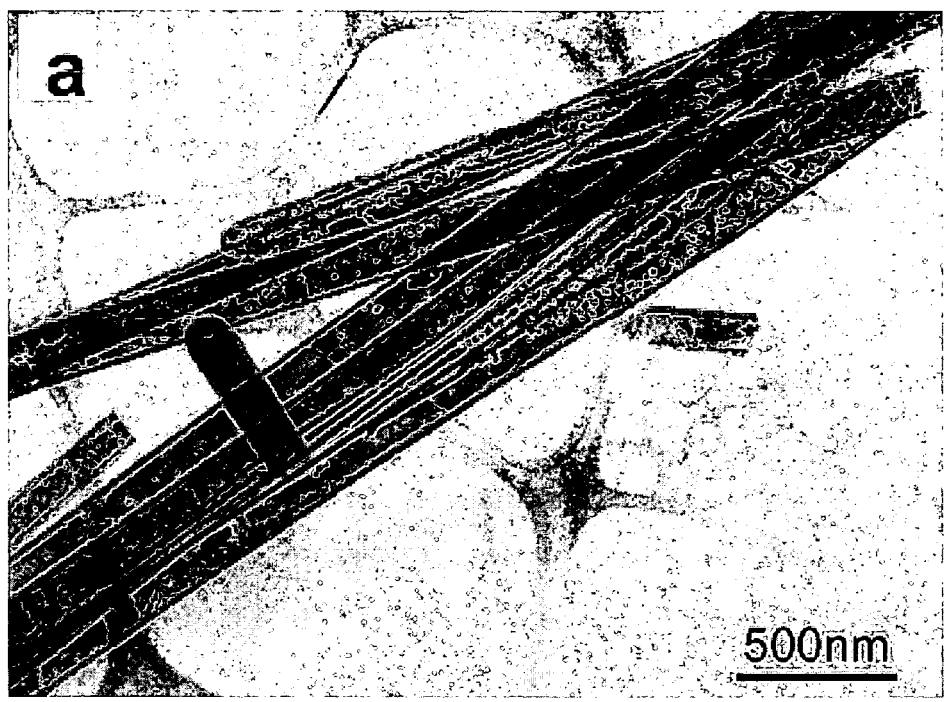
FIG. 7A-7C are images of the nanotubes of FIG. 5B according to an aspect of the present invention, showing the relative uniformity in diameter and wall thickness.
Figure 7B:
Figure 7C:

FIG. 7A through FIG. 7C depict images of dispersing the GaN nanotubes sample in FIG. 5B onto a transmission electron microscopy (TEM) grid for further structural analysis. It was found that the majority of the nanostructures exhibit tubular structures with uniform wall thicknesses, which can be generally seen from FIG. 7A. These nanotubes were found to have inner diameters ranging from 30 nm to 200 nm, similar to the ZnO nanowire arrays, and wall thicknesses between 5 nm to 50 nm.

It was found that the majority of the nanotubes have only one end open, however, tubes with both ends open were also observed. These observations are consistent with the SEM studies, where round-shaped and less-facetted ends are observed after the GaN coating, as depicted in FIG. 5B. It was concluded that the open nanotube ends are originally located at the GaN and substrate interface, which were fractured open during TEM sample preparation. Indeed we have frequently observed these open ends on the substrate surface together with the corresponding nanotubes, an example of which is shown in the inset of FIG. 5B. TEM studies also indicate that the inner cross-section of the nanotubes remains pseudo-hexagonal after template removal.

Figure 8A:
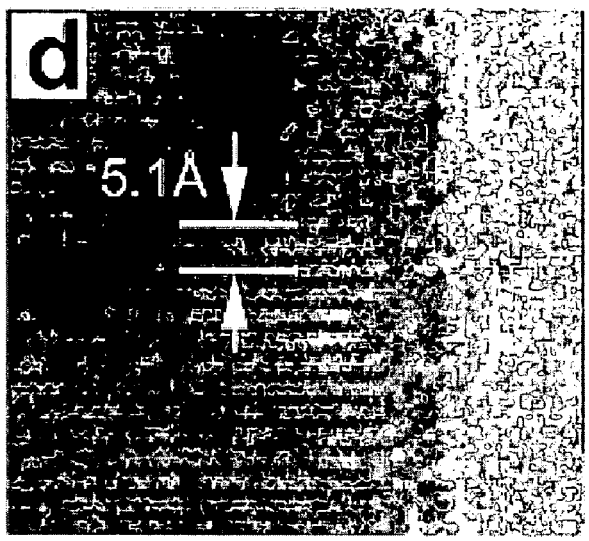
FIG. 8A is a high resolution image of the exterior wall structure in a GaN nanotube of FIG. 5B according to an aspect of the present invention.
Figure 8B:
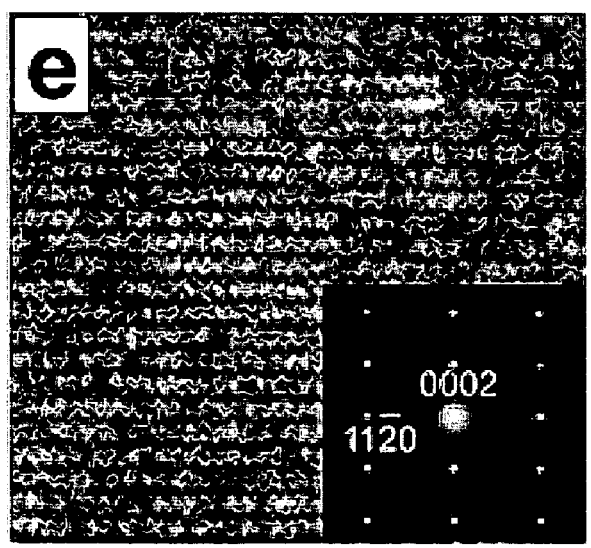
FIG. 8B is a high resolution image of the interior wall structure in a GaN nanotube of FIG. 5B according to an aspect of the present invention, shown with inset of electron diffraction pattern taken on the nanotube along the [T̄ 10] zone axis.

Significantly, electron diffraction (ED) taken on these GaN nanotubes indicates that these tubes are single-crystalline. Returning to FIG. 7E, the inset shows one ED pattern taken along the [$\bar{1}$ 10] zone axis. It can be readily seen that the nanotube is oriented along the c-axis of the wurtzite GaN structure. This is consistent with the XRD data where only (001) peaks were observed. Along the tube axis, a lattice spacing of 0.51 nm for (001) planes of the wurtzite structure can be readily resolved on high resolution TEM images of both the tube surface FIG. 8A and the inside of the tubes FIG. 8B.

Figure 9:
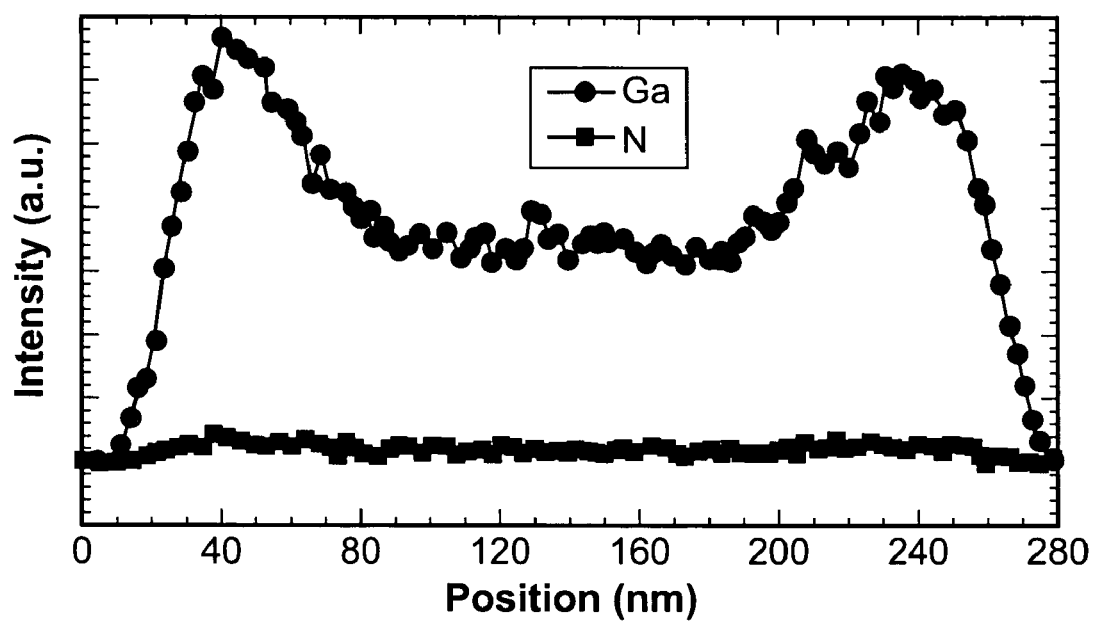
FIG. 9 is a plot of nanotube composition across the nanotube profile according to an aspect of the present invention, as probed by energy dispersive X-ray spectroscopy.
Figure 12:
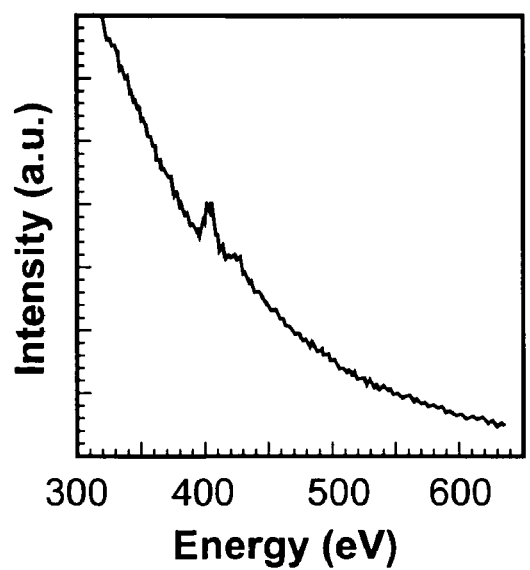
FIG. 12 is a plot of the electron energy loss spectrum collected on the GaN nanotube of FIG. 11.

FIG. 9 illustrates compositional line profile probed by energy dispersive X-ray spectroscopy (EDX) showing well-correlated gallium and nitrogen signals across the tube walls which are indicators of stoichiometric GaN formation during the deposition. This is also clearly reflected in the electron energy loss spectra (EELS) recorded on these nanotubes, as shown in FIG. 12, where strong nitrogen signals were observed. It should be noted that the interfacial diffusion between the GaN layer and the ZnO nanowire templates result in a small amount of Zn or O incorporation within the GaN tube wall.

Figure 10:
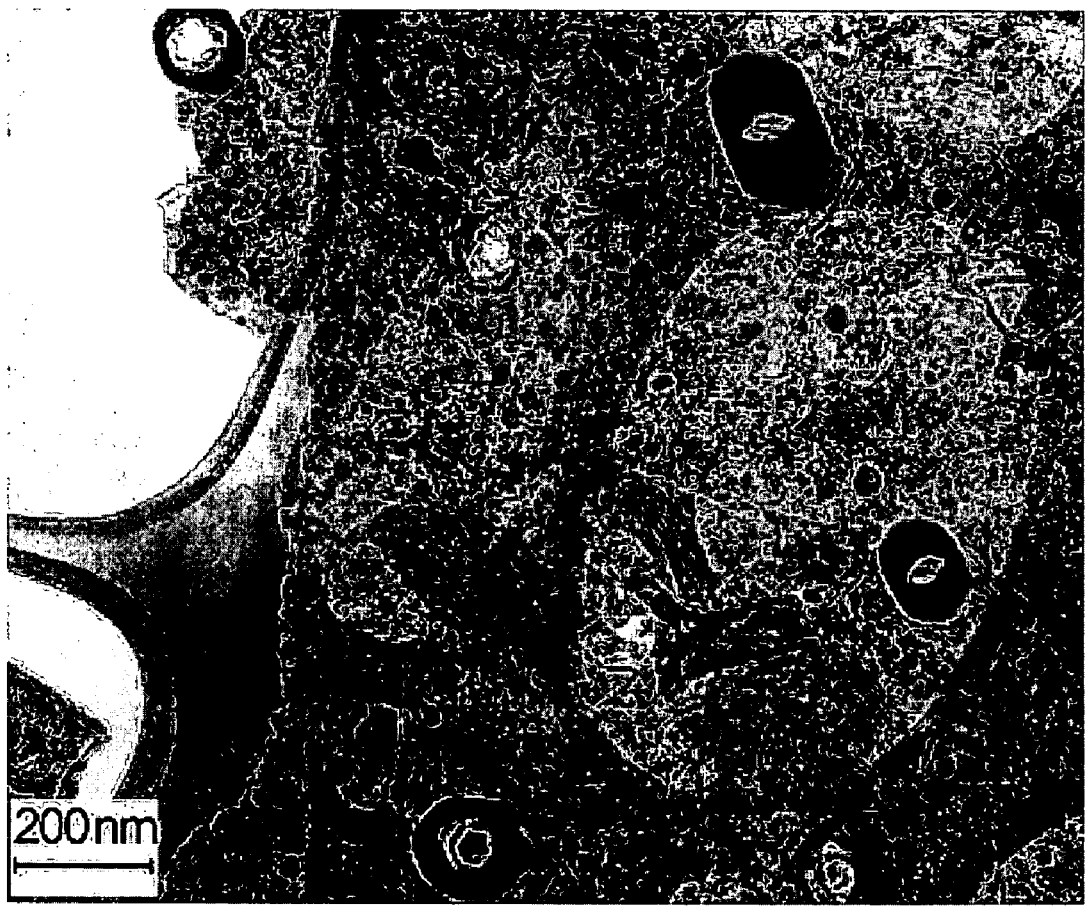

FIG. 10 is a transmission electron microscopy image of an end-on view of several GaN nanotubes. At least two important features can be seen in the image: (1) the inner cross-section of the tubes is pseudo-hexagonal, (2) nanotubes are connected at their base with a porous GaN layer, which is believed to be the primary pathway for the escape of zinc and oxygen species during thermal/chemical etching.

Figure 11:
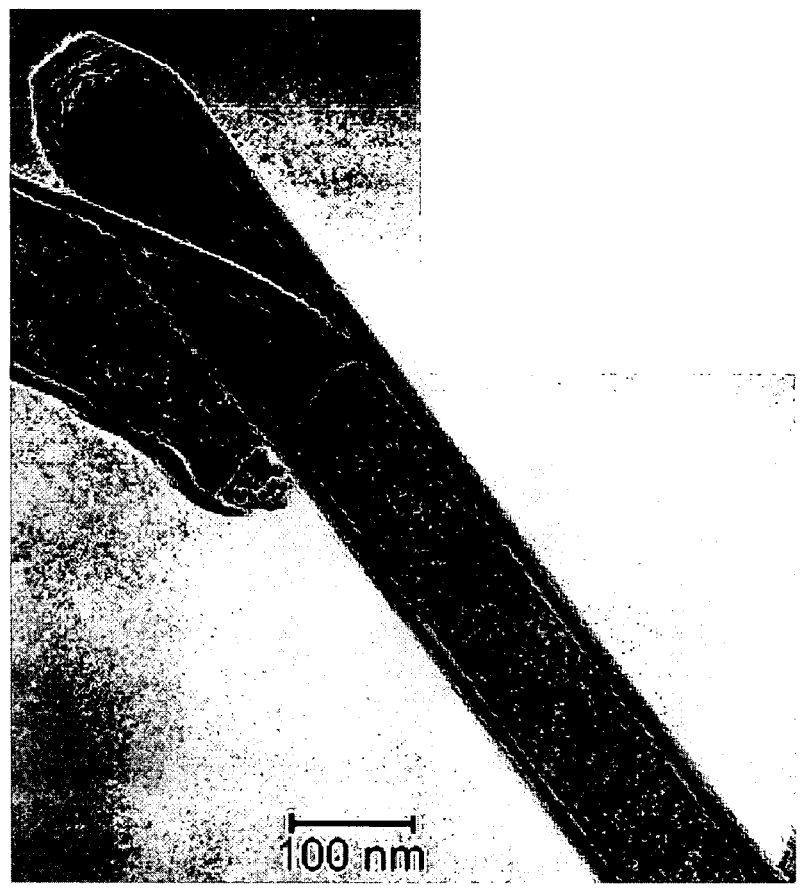
FIG. 11 is an image of a single-crystalline GaN nanotube fabricated according to an embodiment of the present invention and showing its smooth features.

FIG. 11 is a transmission electron microscopy image of a single-crystalline GaN nanotube showing its very smooth internal and external surface.

FIG. 12 is a plot of nitrogen K-edge electron energy loss spectrum collected on the GaN nanotube of FIG. 11.

Taken together, it will be appreciated that high-density arrays of single-crystalline nanotubes can be successfully prepared, such as described for GaN nanotubes fabricated on sapphire substrates. It is important to point out that the GaN nanotube formation process described herein is a marked departure from previous work on inorganic nanotubes.

Previous studies on inorganic nanotubes have been directed toward materials with layered structures (e.g. $VO_x$, $MOS_2$, $NiCl_2$, BN). For those studies on materials that do not have structural anisotropy, (in porous alumina) templating approaches are generally used, which result in predominantly amorphous or polycrystalline tubes. The distinction between amorphous or polycrystalline tubes and the beneficial single crystal tubes shown as being preferably fabricated according to the present invention will be readily recognized by one of ordinary skill in the art.

Figure 13A:
FIG. 13A is an image of an array of nanotubes fabricated according to an embodiment of the present invention, and shown with the nanowire template partially removed.

FIG. 13A, 13B and FIG. 14, FIG. 15 illustrate details of removing the nanowire template within the single-crystalline nanotube. The "epitaxial casting" mechanism described by the invention has been confirmed with TEM studies. In FIG. 13A arrays of GaN nanotubes are shown with their ZnO nanowire templates partially removed. It should be noted that at the bottom of these nanotubes a thin layer of porous GaN film exists. In addition, residues of ZnO nanowire templates remain in the upper portion of the sealed GaN nanotubes. These two observations suggest that the zinc and oxygen species (generated during the thermal chemical etching process) escape from the GaN nanotubes primarily through the underneath porous GaN layer (as shown in FIG. 10).

Figure 13B:
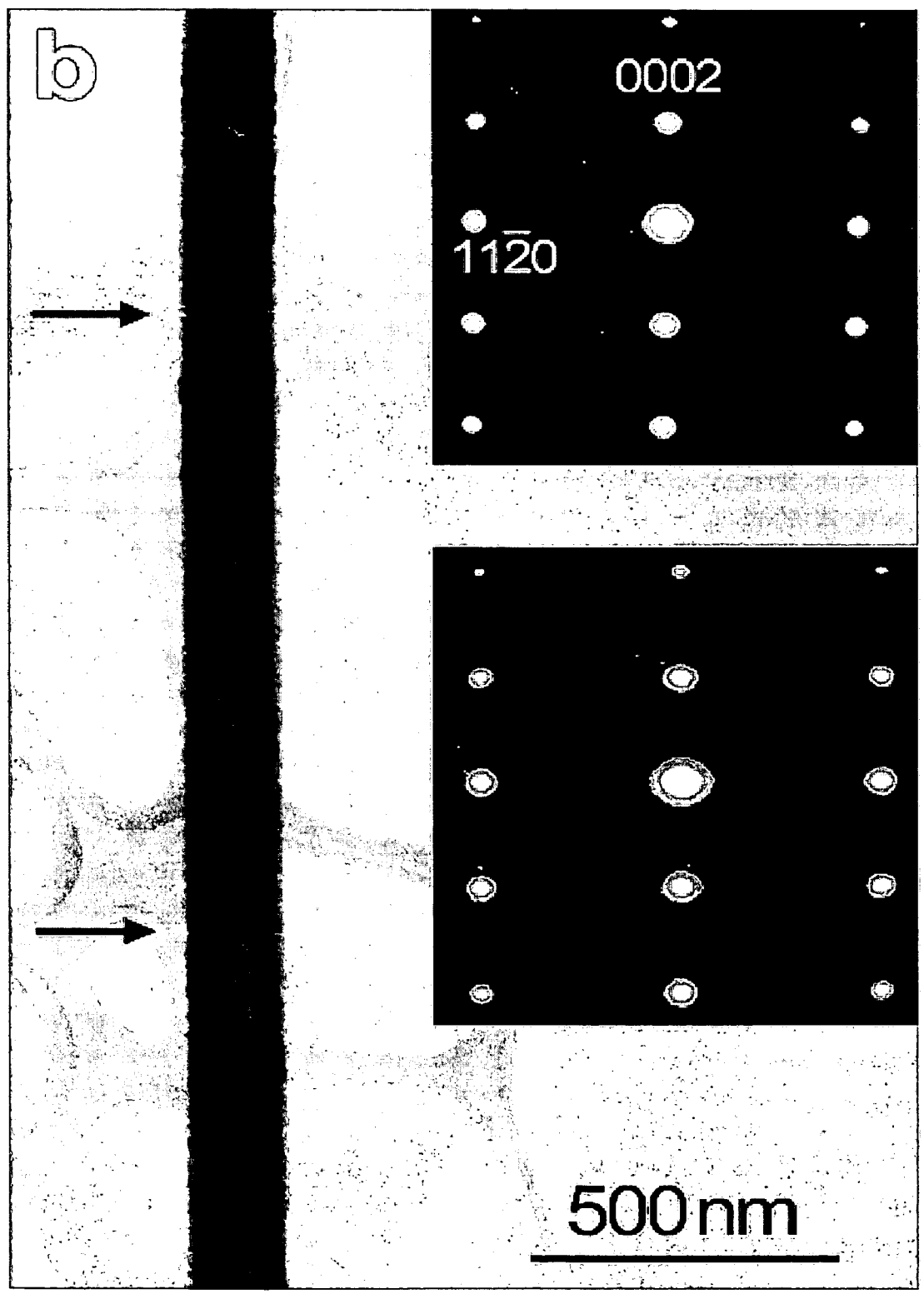
FIG. 13B is an image of a nanotube fabricated according to an embodiment of the present invention with nanowire template partially removed, showing insets of electron diffraction patterns recorded on the core-sheath and the pure tube region along the [T̄ 10] zone axis.
Figure 14:
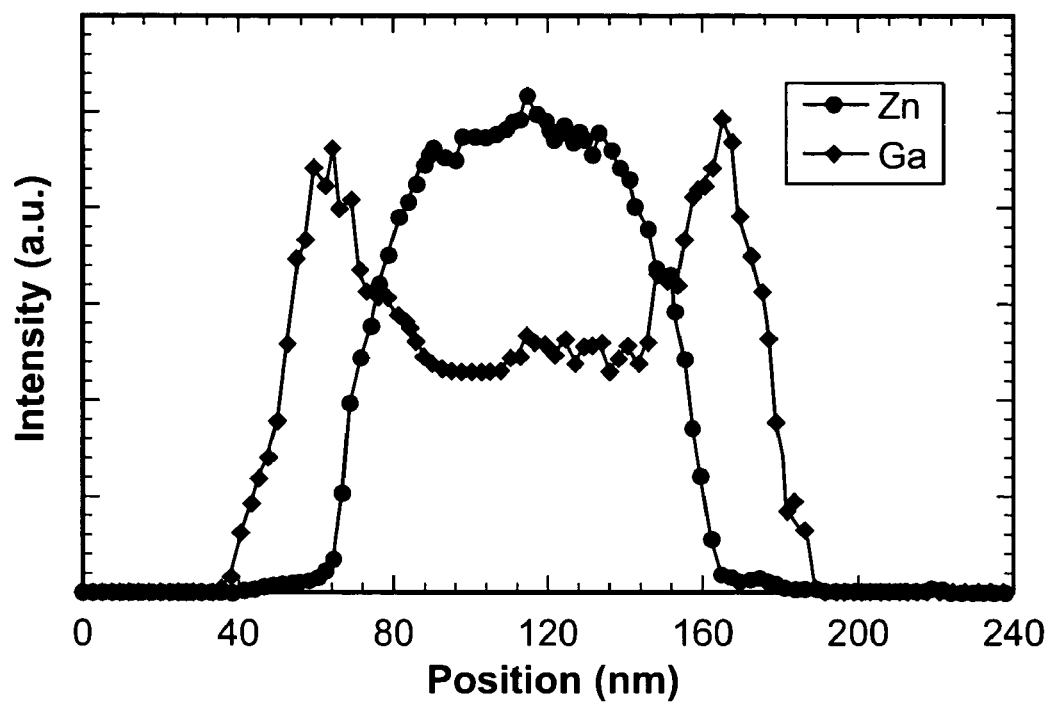
FIG. 14 is a plot of line profiles for the core-sheath of a nanotube at the upper arrow position in FIG. 13B, and showing Ga and Zn signals.
Figure 15:
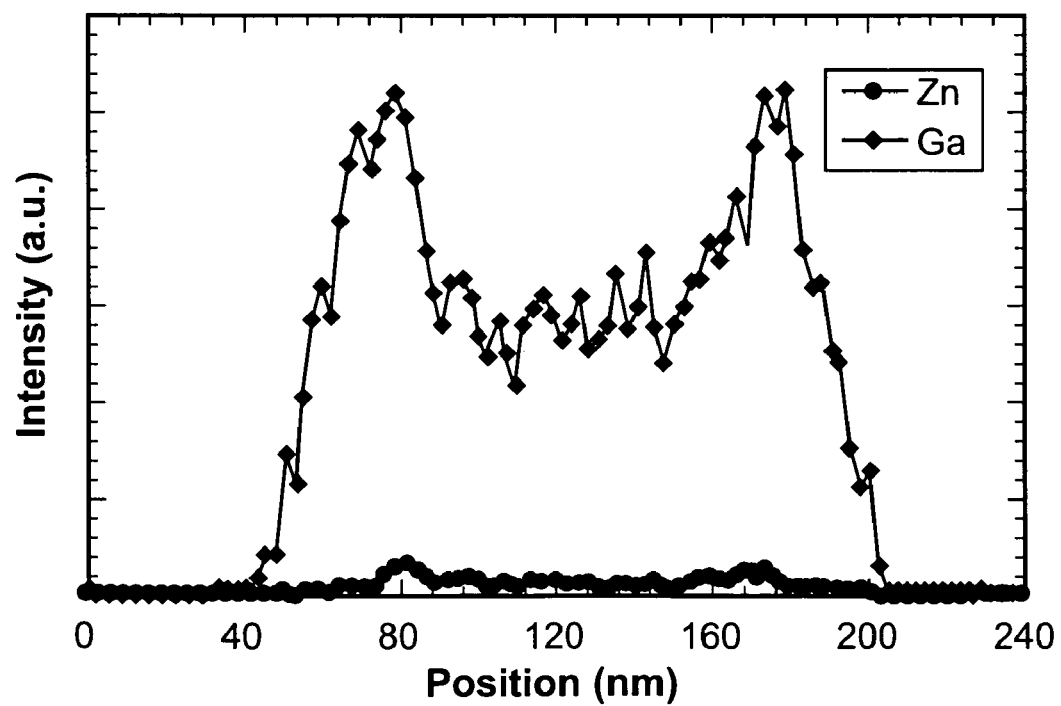
FIG. 15 is a plot of line profiles for the core-sheath of a nanotube at the lower arrow position in FIG. 13B, and showing Ga and Zn signals.

In FIG. 13B a detailed view of a nanotube with a partially removed template is shown at the boundary between the filled (upper arrow) and empty portions (lower arrow) of the nanotube. Electron diffraction shown on the insets of FIG. 13B for the filled and unfilled portions of the nanotube depict an identical set of diffraction patterns for both the tube and the core-sheath region, indicating the wurtzite GaN growth is epitaxial.

The core-sheath nanostructure can be considered as a seamless single domain of a wurtzite GaN/ZnO structure type. Furthermore, comparison of EDX line profiles across the GaN nanotube (aligned at lower arrow) shown in FIG. 14 and the ZnO—GaN core-sheath structure, aligned at the upper arrow, and shown in FIG. 13 unambiguously support the growth mechanism of GaN nanotubes on the ZnO nanowire templates. Once the ZnO nanocylinder is removed, single-crystalline tubes of GaN result. The formation of these single-crystalline GaN nanotubes as taught herein accords a number of benefits over the use of polycrystalline nanotubes in particular in view of the fact that these polycrystalline nanotubes are generally subject to having an irregular shape. It is also interesting to note that microscale tubes of ZnO have been prepared in solution through a preferential chemical dissolution process.

Importantly, the electrical and optical characteristics of these single-crystalline GaN nanotubes are comparable to those of high-quality GaN epilayers grown on ZnO substrates as well as those of GaN nanowires.

Figure 16:
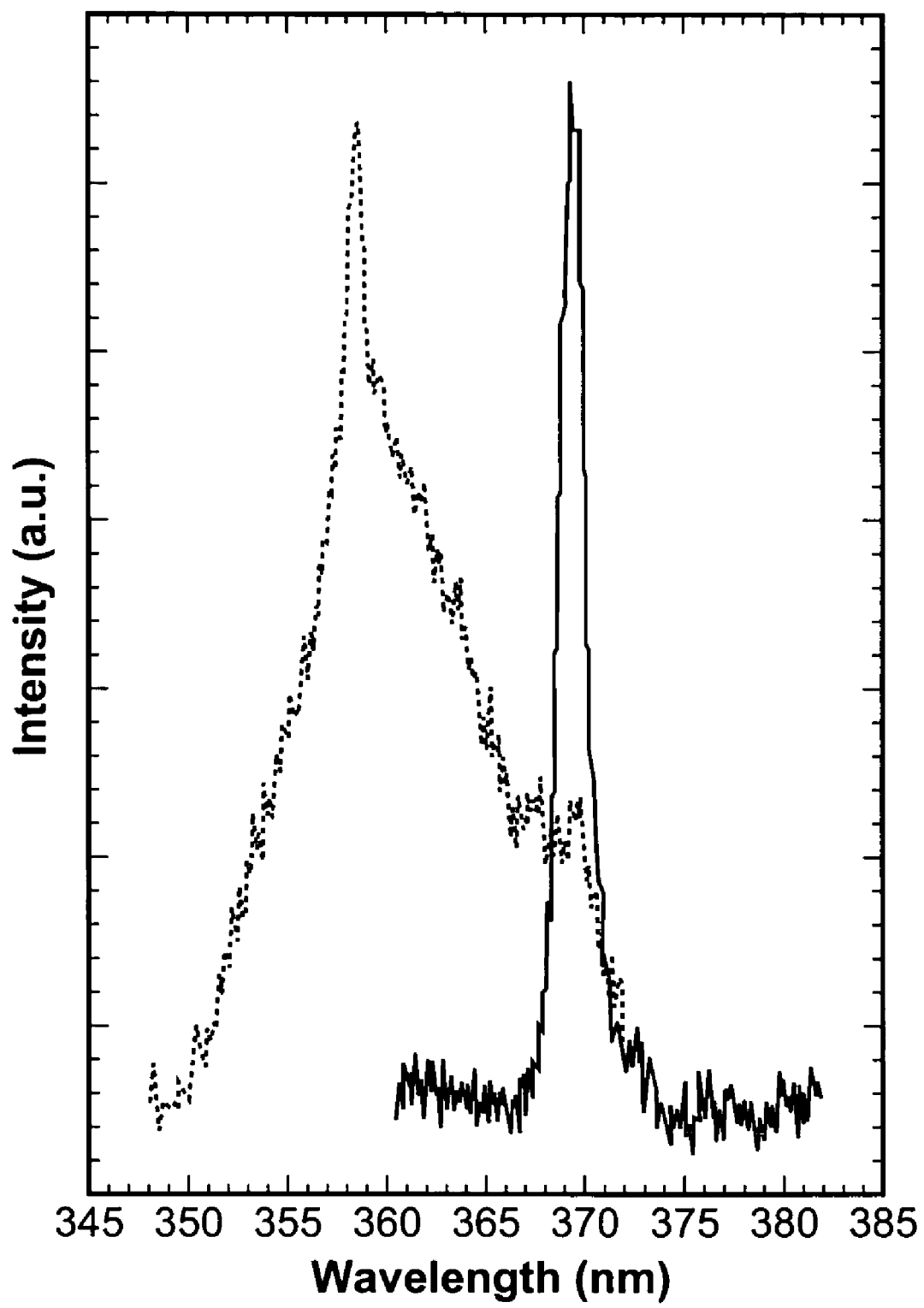
FIG. 16 is a plot of photoluminescence spectra collected on a GaN nanotube according to an aspect of the present invention, showing spectra from both a thin-walled and thick-walled nanotube.

FIG. 16 depicts a low temperature photoluminescence (PL) spectra plot of the as produced nanotubes measured using fourth harmonic output of a YAG laser (266 nm) as an excitation source. It should be noted that no midgap yellow emission was observed. The band edge emission was observed in these nanotube samples between 375 nm and 360 nm, with the thinner tubes emitting at shorter wavelengths. This slight blue shift of the emission could be attributed to the quantum confinement effect since some of the nanotubes have walls as thin as 5 nm, which is smaller than the exciton Bohr radius of GaN.

Referring to the figure, photoluminescence spectra was collected on the GaN nanotubes at 10 K. The samples were excited by 266 nm line of a pulsed Nd:YAG laser (i.e. Spectra Physics™). The photoluminescence signal was transmitted to a 0.3 meter imaging monochromator by an optical fiber, detected by an intensified CCD working under gate mode. Only band edge emission was observed, with the spectra depicted on the left corresponding to the spectra collected on thin-walled (<10 nm) GaN nanotubes, while the spectra depicted on the right corresponds to the spectra collected from thick-walled ($\geq 10$ nm) GaN nanotubes, respectively. It should be appreciated that the emission spectra for the thin tubes is relatively broad due to the broad distribution of tube wall thicknesses for the tested sample.

Figure 17:
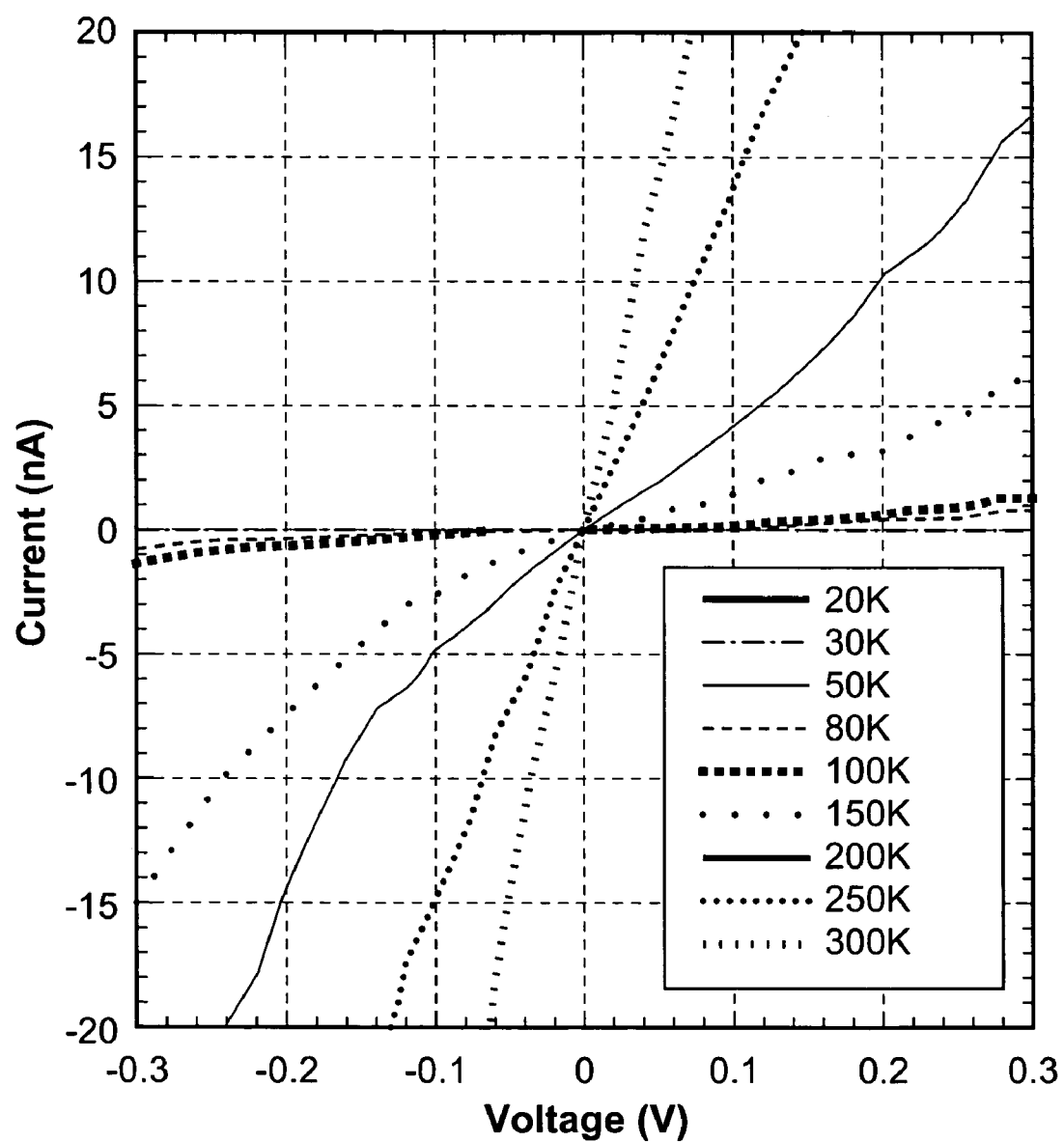
FIG. 17 is a plot of temperature dependence curves of a single GaN nanotube according to an aspect of the present invention.

FIG. 17 depicts an example of electron transport measurements which indicate the resistances of these nanotubes are on the order of 10 M$\Omega$ at room temperature and increases with decreasing temperature, similar to those of high quality GaN nanowires. Referring to the figure, temperature dependence I-V curves of a single GaN nanotube are shown. The electrodes (20 nm titanium, Ti and 80 nm gold, Au) for the electrical measurements were fabricated using e-beam lithography and thermal evaporation, although other techniques may be utilized. To form a stable contact, a rapid thermal annealing step was performed at 450° C. for about thirty seconds, although any convenient means of contact formation may be utilized.

The successful preparation of single-crystalline GaN nanocapillaries utilizing the present epitaxial casting process is indicative of the ability to prepare nanotubes/nanocapillaries, in particular single-crystalline nanotubes/nanocapillaries, of inorganic solids having non-layered crystal structures. It is anticipated that this new class of semiconductor nanotubes/nanocapillaries can be utilized in a number of beneficial technical applications in the fields of nanoscale electronics, optoelectronics, and chemistry in addition to use with fluidic systems. The present invention provides robust semiconductor nanotubes, having uniform inner diameter, and inner walls that can be readily functionalized, while both ends of the nanotubes can be made accessible for fluid flow applications.

Oxidation and Etching Method

Referring now to FIG. 18A through FIG. 18G, a second method of fabricating nanotubes using a sacrificial template according to the present invention is illustrated. This method is referred to herein as "oxidation and etching" since this method forms robust nanotube arrays by translating vertical nanowire arrays into oxide nanotube arrays. In one embodiment, nanotube cores (templates) are formed from silicon (Si) nanowires, with a metal cap (i.e. Au), such as commonly fabricated using thermal oxidation and etching. Next, the Si nanowire arrays are thermally oxidized which results in arrays of thin Si nanowires sheathed by a thick layer of silicon oxide (SiO$_2$). This oxidized nanowire array is then selectively etched, such as with xenon fluorine (XeF$_2$) to remove the silicon nanowire cores, leaving an array of ordered silicon dioxide nanotubes with controllable inner diameters. The inner diameters are controlled by the initial diameters of the silicon nanowires and the thermal oxidation process. The inner tube diameter of the nanotubes may be in the range of from approximately 10 nm to 200 nm.

It should be appreciated that single nanotubes or random samples can be formed as an alternative to forming the nanotubes in an array. Other nanotube compositions can also be fabricated in this manner as well, including, but not limited to, GaO, InO and other oxides and insulating materials. The following describes implementation details of an embodiment of the present fabrication process.

EXAMPLE 2

FIG. 18A illustrates silicon nanowire arrays which were prepared using chemical vapor deposition (CVD) epitaxial growth employing silicon tetrachloride (SiCl$_4$, Aldrich, 99.99%) as the silicon source. Hydrogen (10% balanced by argon) was used to reduce SiCl$_4$ at high temperature (900-950° C.). Gold (Au) thin film was coated on Si (111) substrates 30 to initiate the growth of silicon nanowires 32 via the vapor-liquid-solid growth mechanism. The gold remains as caps 34 on the Si nanowires. This approach to growing Si nanowires was developed and is utilized by the inventors for the synthesis of vertical Si/SiGe superlattice nanowire arrays. The silicon nanowire array samples were heated, such as loaded into a tube furnace and heated at 800-1000° C. for one hour under the continuous flow of pure oxygen (O$_2$).

FIG. 18B depicts the nanowires 32 after being uniformly oxidized to provide SiO$_2$ sheaths 36 with continuous silicon cores inside. During oxidation, the nanowire tips 34 are preferably oxidized to provide an oxide cap 34' on each vertical wire for preventing the selective etching of silicon cores. Therefore, the first step after thermal oxidation is to selectively remove the SiO$_2$ caps 34' from the Si/SiO$_2$ core-sheath nanowires.

FIG. 18C illustrates a preferred mode of removing the SiO$_2$ caps. A polymer 38 is deposited to fill in the space between the nanowires such that the SiO$_2$ sidewall 36 is protected by the matrix polymer as an etch-resistant material. In the present example, parylene dimer (di-para-xylylene, -(CH$_2$-Ph-CH$_2$-)$_2$) was thermally evaporated at 160° C., dissociated at about 650° C. and deposited onto the Si/SiO$_2$ core-sheath nanowire array sample for approximately five (5) hours to yield a continuous coating of parylene (poly-para-xylylene, -(CH$_2$-Ph-CH$_2$-)$_n$) polymer. This parylene deposition is conformal, starting from thin layer coating on the surface of nanowires and then filling all the interval space between nanowires. This process leads to a highly conformal wrapping of the nanowires without pinholes or cracks. It should be appreciated that the core-sheath nanowires may be processed without embedding in polymer, in particular when processed nanowires are processed in a non-array form, or separately.

FIG. 18D illustrates the core-sheath array subsequent to oxygen plasma etching of the surface of the polymer fill 38, such as the parylene in order to expose the tips of the Si/SiO$_2$ nanowires.

FIG. 18E depicts the core-sheath array after immersion in a buffered hydrofluoric acid solution for about two (2) minutes to selectively remove the SiO$_2$ caps 34' and expose the silicon cores 32.

FIG. 18F illustrates the sheath array after the silicon nanowire cores 32 were removed by an etchant, such as XeF$_2$ etchant gas. It will be noted that although some material has been removed, a layer of etch-resistant material 38' still protects the bulk of the nanotube walls. Etching is preferably performed by loading the core-sheath array into a XeF$_2$ etching chamber, with a chamber temperature for example being adjusted to 40° C. After purging and flushing with nitrogen, the XeF$_2$ vapor was introduced together with nitrogen gas, N$_2$(XeF$_2$:N$_2$=4:5) to conduct etching for thirty (30) seconds at total pressure of about nine Torr. The chamber was then evacuated and flushed with nitrogen and etching carried out for a second cycle. In the present embodiment eight cycles were carried out to achieve complete etching of the silicon cores.

According to the above process silica nanotube arrays were obtained which are embedded in the parylene membrane 38, wherein the continuous pores run through the entire polymer film.

FIG. 18G depicts a resulting nanotube array 36' after the parylene matrix was etched away, such as using high-power oxygen plasma treatment for thirty (30) minutes to yield a vertically oriented, robust silica nanotube matrix attached to substrate 30.

EXAMPLE 3

Figure 19A:
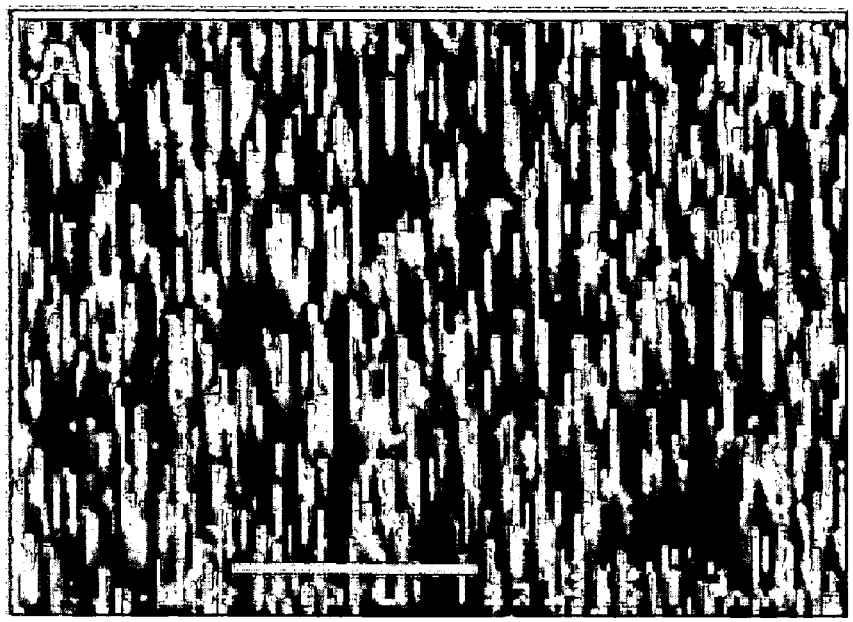
FIG. 19A-19D are images of silicon nanotube array formation according to aspects of the present invention, shown including detail views on insets of FIG. 19B-19D.

FIG. 19A-19D are images of nanotube formation according to the invention, registered as scanning electron micrographs (SEM). A silicon nanowire array is shown in FIG. 19A, with the Si nanowires vertically orientated to form a substantially perfect array. Typical sizes of the silicon nanowires are 50-200 nm, and the length is around 8 µm. On the top of each nanowire can be seen a bright gold tip indicative of the vapor-liquid-solid growth.

Figure 19B:
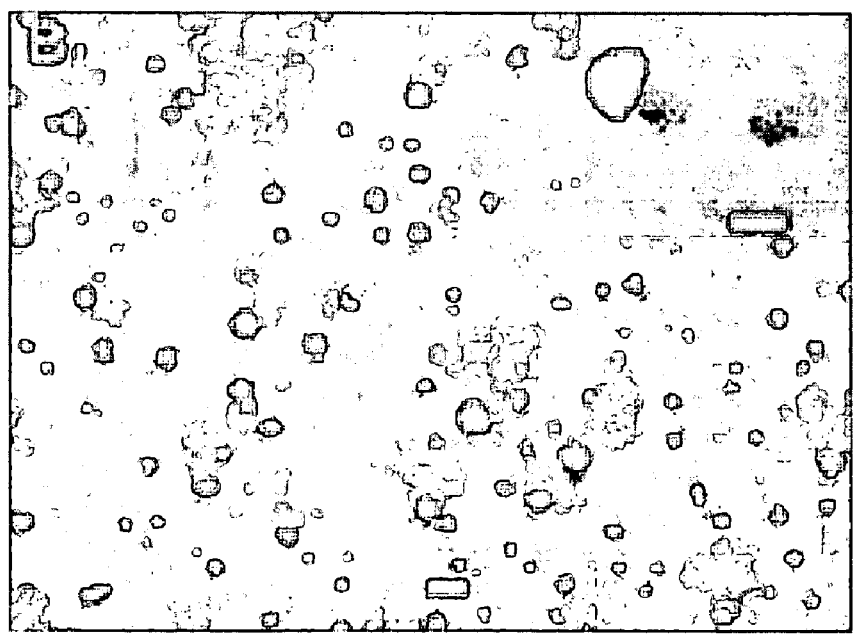

FIG. 19B illustrates the nanotubes after parylene deposition, SiO$_2$ cap removal, and the etching of the silicon cores, wherein a silica nanotube array embedded in parylene membrane is formed. The pores can be readily seen on the polymer surface. The bright spots on the image corresponding to the gold nanoparticle tips, which nearly take the shape of half spheres. The membrane has a relatively flat surface. The inset within FIG. 19B depicts high magnification of two silica nanotubes embedded in the parylene membrane, clearly showing the hollow pores with silica walls.

Figure 19C:
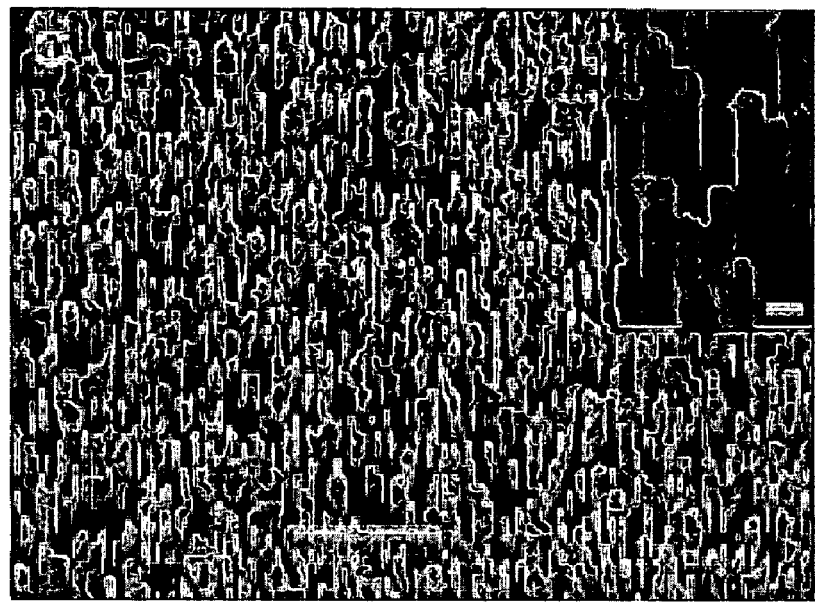
Figure 19D:
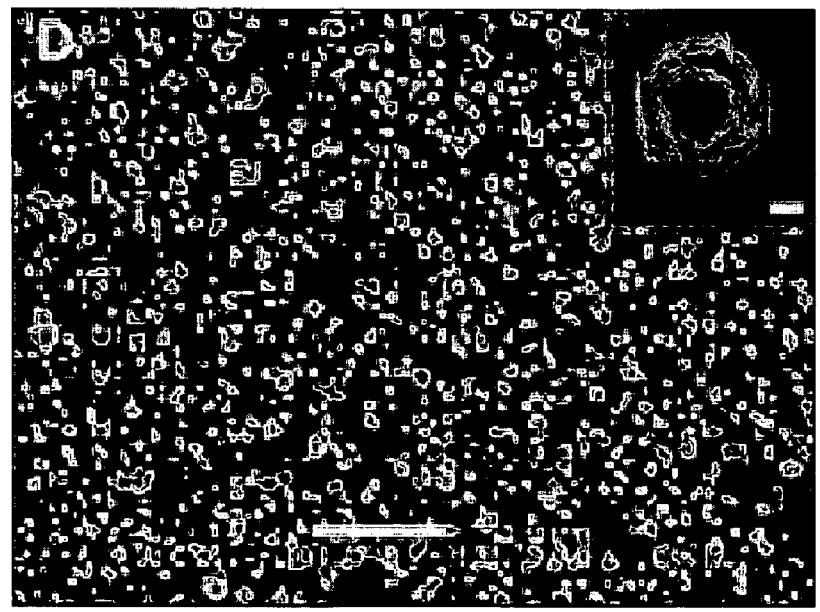

FIG. 19C and FIG. 19D are perspective and top views, respectively, of the nanotube array after oxygen (O$_2$) plasma etching of parylene wherein a free-standing silica nanotube array is obtained. As can be seen, the nanotubes are well aligned and retain the vertical orientation of the starting silicon nanowire templates. The inset of FIG. 19C shows a zoom view of the nanotubes in a high magnification SEM image showing clearly the morphology of the vertical nanotube array. The images reveal that the Si nanowires are vertically oriented in an array, with uniform diameters along their length ranging from approximately 50 nm to 200 nm, with lengths of up to approximately 8 µm, and an average length of about 5 µm. The average diameter of the resulting silica nanotubes exceeds that of the template silicon nanowires, as a result of the structural expansion caused by thermal oxidation. The inset of FIG. 19D is a detailed top view from which the hexagonal shape of the tube is visible. The scale bars on FIG. 19A, 19B, 19C are 10 µm, 1 µm, and 10 µm respectively. The silica walls of the nanotubes were found to exhibit a well-defined hexagonal shape indicative of the <111> orientation of the original Si nanowires and the anisotropic in-plane etching rates.

Figure 20A:
FIG. 20A-20B are images of silica nanotubes according to aspects of the present invention.
Figure 20B:
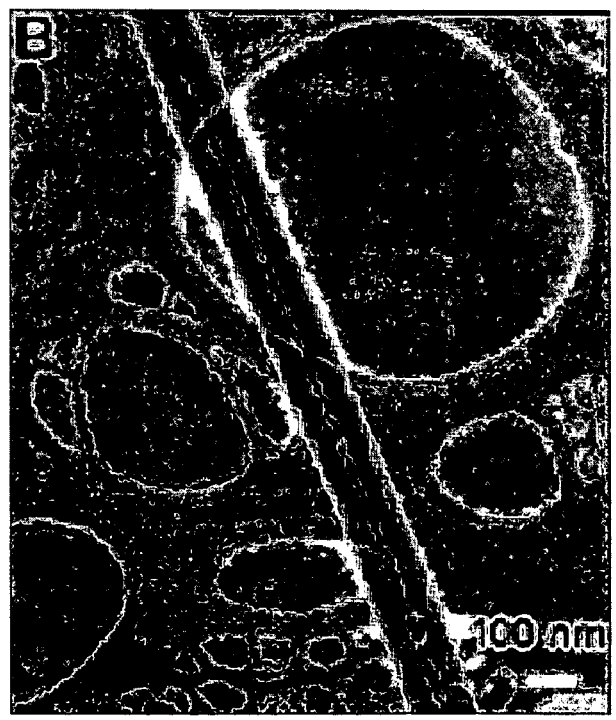

FIGS. 20A and 20B are transmission electron microscopy (TEM) images which further illustrate the high-quality of the silica nanotube formation. In FIG. 20A the uniform inner diameter is shown, which generally persists along the entire length of the nanotube. The pore sizes for the nanotubes range from about 10 nm to 200 nm, with smooth inner and outer walls.

Nanotube thickness was found to be around 70 nm for a 1000° C. thermal treatment, despite the range of pore sizes for the nanotubes. This result is considered reasonable because the oxidation layer thickness is expected to be the same for the nanowires under a constant thermal treatment condition since the thermal oxidation of the silicon is a self-limiting process. The self-limitation of the process can be taken advantage of for controlling tube size and wall thickness by adjusting the characteristics of the thermal treatment process, such as the treatment temperature.

As an example of how nanotube characteristics can be controlled, a sample oxidized at 900° C. has a typical wall thickness of around 55-65 nm, while a temperature of about 800° C. yields a wall thickness of around 30-35 nm. The nanotube shown in FIG. 20B has a pore size of approximately 20 nm, however as can be seen, it still is uniform and has a smooth inner wall. Occasionally branched nanotubes were produced, it should be appreciated that these nanotubes will provide benefits for select nanofluidic and electronic applications.

This multiuse approach of making silica nanotube array templates from silicon nanowire arrays is a well-controlled process capable of controlling the pore size and the array height, while the resultant nanotubes can be readily subjected to different surface modification on inner and outer walls. The respective surface modification of inner and outer walls can be important in applications such as bioseparation and smart molecule transport. In addition, the walls of these nanotubes are formed from pinhole-free condensed thermal oxide, which can be advantageous in terms of its mechanical robustness and fluidic stability.

Consequently, this new class of semiconductor nanotubes represented by the present invention is mechanically robust, electrically and optically active. Therefore, these nanotubes could offer additional opportunities for further fundamental research as well as technological applications in nanocapillary electrophoresis, nanofluidic biochemical sensing, nanoscale electronics and optoelectronics. It should be appreciated that the successful preparation of single-crystalline GaN nanotubes using this "epitaxial casting" approach suggests that it is generally possible to prepare single-crystalline nanotubes of inorganic solids that have non-layered crystal structures.

It should also be appreciated that the techniques described herein may be further extended by forming multiple sheath layers. Each of these sheath layers may comprise different materials, different doping constituents or levels. Still further, longitudinal portions (segments) of the nanotube may be differentially processed to yield different properties between segments of the nanotube structure, or multilayer nanotube structure. The following nanotubular structure are provided by way of example and not by way of limitation.

Figure 21:
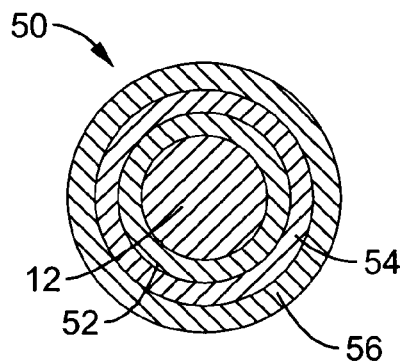
FIG. 21 is a cross-section of a multilayer nanotube according to an aspect of the present invention and shown with a gallium nitride sheath sandwiched between insulating aluminum nitride layers.

FIG. 21 depicts a multilayer nanotube 50 comprising a sacrificial ZnO nanowire 12 (prior to removal) over which a gallium nitride (GaN) sheath 54 is held between two sheaths 52, 56 of aluminum nitride (AlN). It will be appreciated that the sacrificial nanowire may be removed at any time after at least the first sheath layer has been deposited over the nanowire, and it could be removed subsequent to depositing the last sheath layer.

Figure 22:
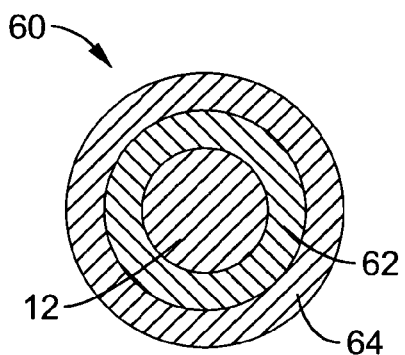
FIG. 22 is a cross-section of a multilayer nanotube according to an aspect of the present invention and shown with a P-doped sheath over an N-doped sheath which surrounds the sacrificial core.
Figure 23:
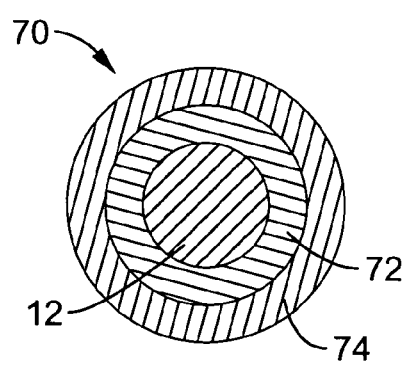
FIG. 23 is a cross-section of a multilayer nanotube according to an aspect of the present invention and shown with an N-doped sheath over a P-doped sheath which surrounds the sacrificial core.

FIG. 22 and FIG. 23 depict forming sheaths of alternately doped material 60. FIG. 22 showing P-doped GaN 62 over a sacrificial core 12 (prior to removal), such as ZnO, and N-doped GaN material 64 over the P-doped material. Similarly, FIG. 23 illustrates the converse of FIG. 19 with P-doped material 74 over N-doped material 72 which sheaths core 12 (prior to its removal). It should be appreciated that from the present methods numerous circuits may be fabricated, including diodes, light emitters, light detectors, electron transport devices (i.e. bipolar transistors, FETs, insulated gate FETs, and so forth) and combinations thereof. Connection to device layers can be provided from the core, or external circumferential connections, while connections may also be embedded into the material layers. The above process methodology may be continued for producing any desired number of nested sheaths within a given nanotube.

Figure 24:
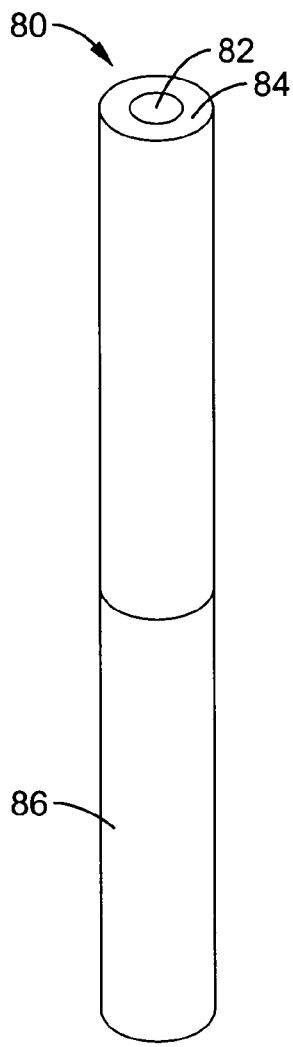
FIG. 24 is a perspective view of a sacrificial core covered with a solid sheath and having two longitudinal nanotube segments according to an aspect of the present invention.
Figure 25:
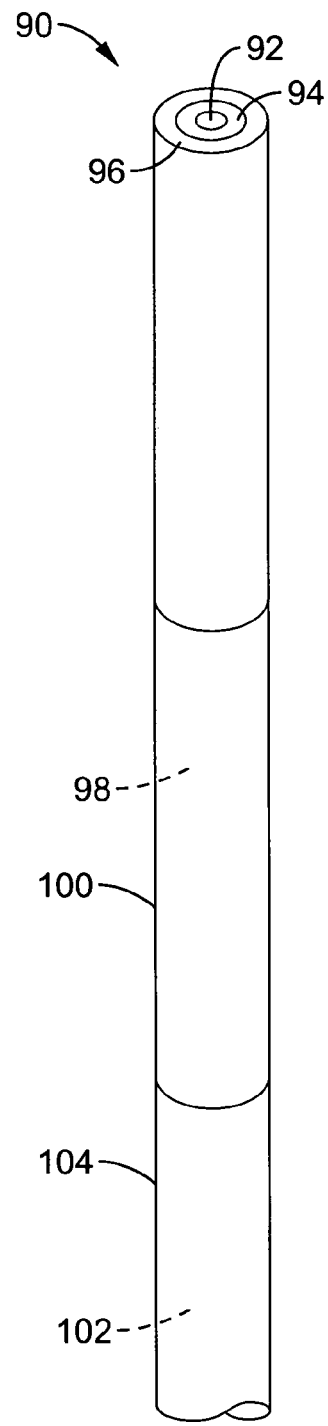
FIG. 25 is a perspective view of a sacrificial core covered with multiple sheaths and having multiple longitudinal nanotube segments according to an aspect of the present invention.

FIG. 24 and FIG. 25 depict forming segmented nanotube sheaths by the present invention, wherein the different segments are formed from different materials, different dopants, different levels of doping, or combinations thereof. These sheaths may be fabricated segment-by-segment in any convenient manner, such as utilizing conventional masking techniques.

In FIG. 24 a nanotube 80 is depicted having two segments of different sheath material 84, 86 disposed longitudinally over a sacrificial core 82. FIG. 25 depicts a nanotube 90 formed from three or more longitudinal segments of different material, differently doped material, or material that is otherwise configured to provide different properties. Furthermore, the nanotube is shown having at least two sheaths of material.

A core 92 is shown prior to removal, with an upper-inner sheath 94, an upper-outer sheath 96, a middle-inner sheath 98, a middle-outer sheath 100, a lower-inner sheath 102, and a lower-outer sheath 104. It should be recognized that any desired number of sheath layers may be deposited and that nanotube may be fabricated with any number of longitudinal segments. It should also be appreciated that insulators and electrical connections on the sheath layers may be formed as portions of different sheath segments. Furthermore, the removed core of the nanotube may be utilized as a fluid via, or lined with material, such as metal, to form another layer (i.e. conductive contact layer).

Figure 26:
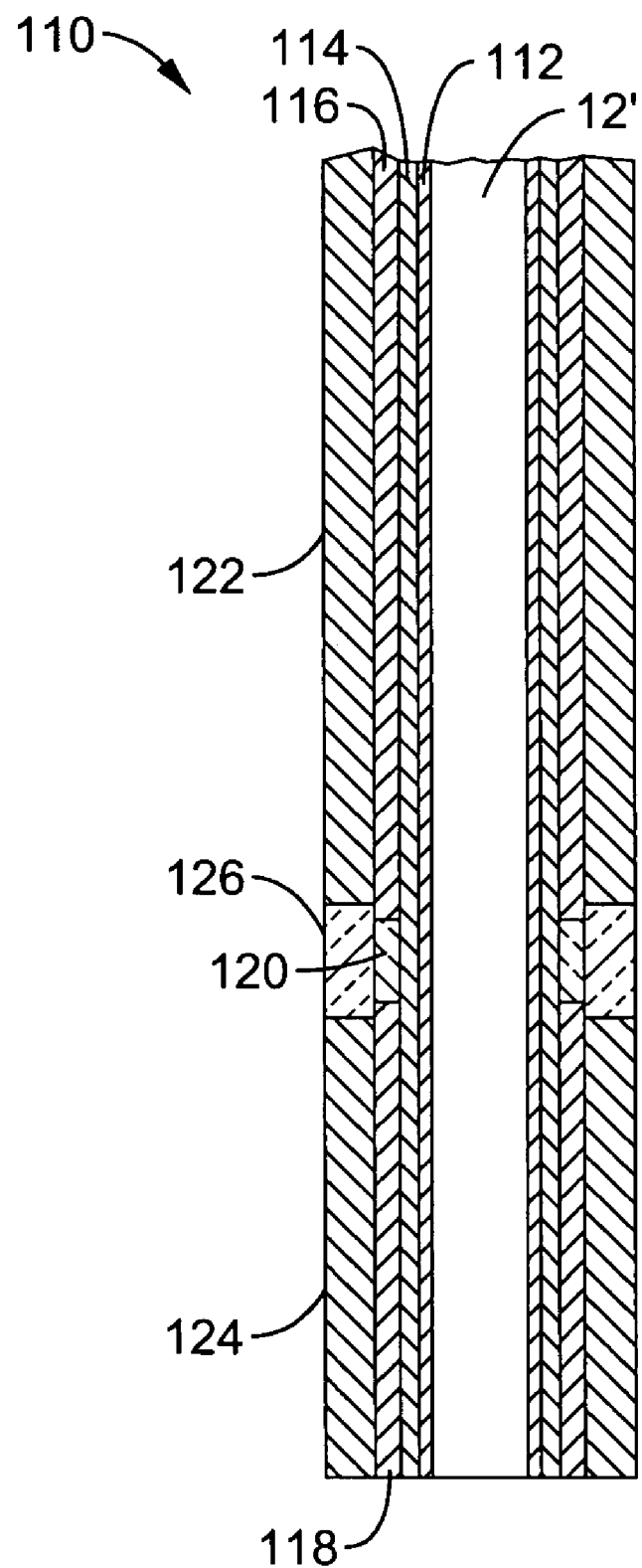
FIG. 26 is a cross-section of fabricating a nanotubular device according to an aspect of the present invention, shown comprising a hollow core NPN transistor.

FIG. 26 illustrates by way of example a cross-section of a nested sheath of layers 110 forming a bipolar transistor. A hollow 12' represents from where the sacrificial nanowire core was removed. The interior of hollow 12' is shown lined as a metallic contact 112. Three sheaths are shown in the figure. A P-doped semiconducting inner sheath 114 is shown. Separated middle sheaths of N-doped semiconductor 116, 118, are depicted between which a central insulating ring 120 is shown surrounding inner sheath 114. Finally a conductive outer sheath is shown with upper conductor 122 and lower conductor 124 separated by insulating sheath segment 126. It will be appreciated that the simple example depicts a form of bipolar NPN transistor along the nanotube length, having exterior emitter contact 122 and collector contact 124 and a base contact 112 lining hollow core 12'. The thickness of the layers may be varied to achieve desired electrical properties, or to enhance rigidity such as provided by the external sheath segments 122, 124, 126.

The transistor is provided by way of example and a wide assortment of devices may be fabricated according to the techniques of the present invention. It should be appreciated that various material and electrical properties may be achieved utilizing the methods of the present invention. Furthermore, various electronic devices, such as diodes, light emitting diodes, lasers, transistors, field effect transistors, and so forth may be produced in accord with the teachings of the present invention.

As can be seen, therefore, embodiments of the present invention include methods of fabricating nanotubes by forming a sheath over a sacrificial core, and then removing the core. Two general methods were described: (i) epitaxial casting and (ii) oxidation and etching. Furthermore, examples of specific nanotube structures were described, such as a GaN nanotube (over a ZnO sheath) using the epitaxial casting method and a $SiO_2$ nanotube (over a Si sheath) using the oxidation and etching method. However, other materials can be used including, without limitation. GaN, Ge, Ag, group II-VI, III-V, elemental group IV (e.g., Si, Ge), and metals as core materials, and further, including without limitation, group II-VI, II-V, elemental group IV, metals, oxides of the above, and polymers as sheath materials. Note also that all of the sheaths can be doped during formation.

Nanofluidic Devices

A number of devices are described in the remainder of the application which can be fabricated from nanotubes in general, and which can be more preferably fabricated from nanotube structures fabricated according to the invention. Although silica nanotubes are generally described herein other forms of fluid compatible nanotubes may be utilized, for example nanotubes made from GaAs, CdSe, GaP, InP, Ge, InAs, GaO, InO and so forth.

By way of example a tube-field-effect transistor (TFET) is described along with a nanocapillary electrophoresis array technology (NEAT) device that can separate and identify molecules within electronic detection systems.

Figure 27:
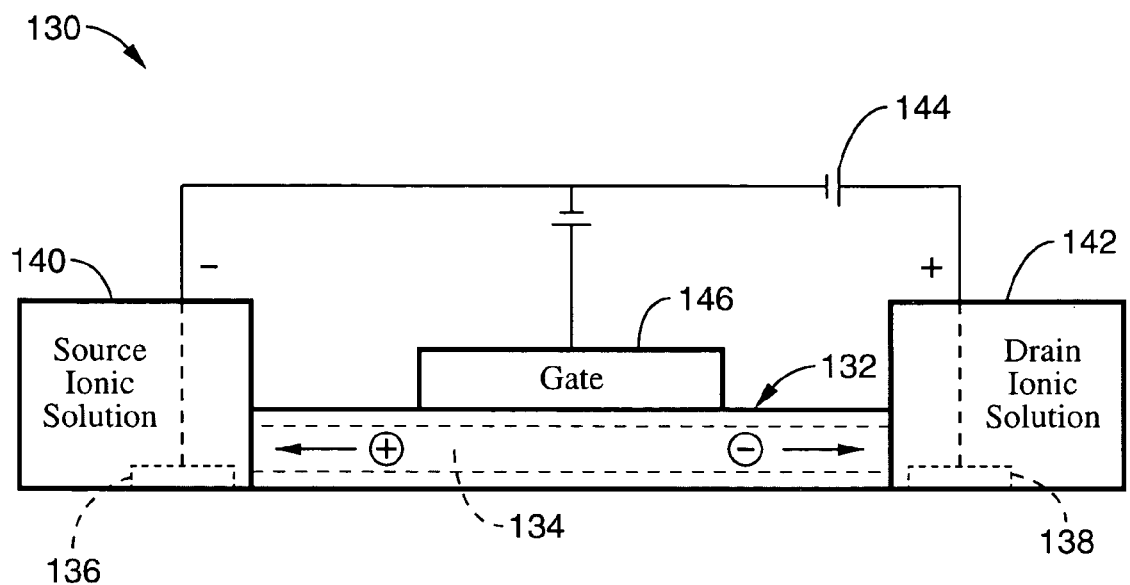
FIG. 27 is a perspective view of a nanofluidic transistor according to an embodiment of the present invention, shown with an electrical source, drain and gate spanning a nanotube segment whose ends are coupled to reservoirs of ionic solution.

FIG. 27 illustrates a schematic diagram of a nanofluidic transistor 130 formed on a semiconducting nanotube 132, such as formed from GaN. The nanotube is shown filled with an ionic solution 134 and coupled on both ends to fluidic reservoirs. Within fluidic reservoirs 140, 142 are a source electrode 136 and drain electrode 138, respectively. In another embodiment, the source and drain electrodes are in the reservoirs and contact the ends of the nanotube, and in another embodiment the source and drain contacts are attached directed to the exterior of the nanotubes near each end which facilitates current flow through the semiconducting wall of the nanotube.

By applying a voltage bias 144 between source 136 and drain 138, a current is induced between source 136 and drain 138 through nanotube 132. A conducting plate (gate) 146 covers part of the length of nanotube 132. A voltage bias on gate 146 will block the ion transport, thus acting like a valve between the source and drain. If biological molecules, which are generally charged, are introduced into the nanotube, they could also be manipulated using the voltage bias on the gate. The use of multiple gates is contemplated, such that ions and biomolecules can be manipulated spatially.

In contrast to the artificial nanopores fabricated using soft lithography or ion milling, the inorganic tubes embodied herein readily circumvent the issues of scaling and pore size limitations. Silica and GaN nanotubes are described as illustrative model sensing systems, with Silica being insulator and GaN being semiconducting, which is particularly well suited for the two sensing mechanisms (NEAT and TFET) which are nanofluidic device embodiments described herein. The NEAT embodiments utilize the insulating silica tubes, or other fluid compatible nanotubes, and sensing is carried out by monitoring the ion conductivity through the individual nanotubes when large molecules are present in the nanofluidic system.

An embodiment of the TFET utilizes semiconductor single crystalline GaN nanotubes as the fundamental nanofluidic sensing elements, for example as shown in FIG. 27. The sensing is carried out by monitoring the conductivity of the nanotubes when possible electron transfer occurs at the analyte/tube interfaces. This TFET would be the analogue of the bio- and chem-field effect transistors, with internal chemical gating within the nanotubes.

In contrast to capillary electrophoresis, as described previously, the proposed NEAT (nanocapillary electrophoresis array technology) will separate and identify the molecules through ligand-receptor binding, and will utilize inexpensive on-chip electronic detection systems.

The use of functionalized nanopores seems to offers the best approach in biomolecular analysis at the limits of sensitivity (single molecule) and specificity (single-base pair mismatch). Ideally, one would like to make arrays of such biosensors such that mixtures of biomolecules could be analyzed simultaneously in a multiplexed manner. The aspects of the present invention overcome the difficulties in maintaining single channels in stabilized membranes by fabricating functionalized artificial nanocapillaries.

One of the goals of this project is to develop Nanocapillary Electrophoresis Array Technology (NEAT) and Tube Field Effect Transistor (TFET) as platforms for ultrasensitive (down to single molecular level) chemical and biological sensors with high specificity. At the heart of NEAT/TFET, will be the use of nanocapillaries 5-20 nm in diameter and made of silicon dioxide ($SiO_2$) or semiconductor GaN.

Figure 28:
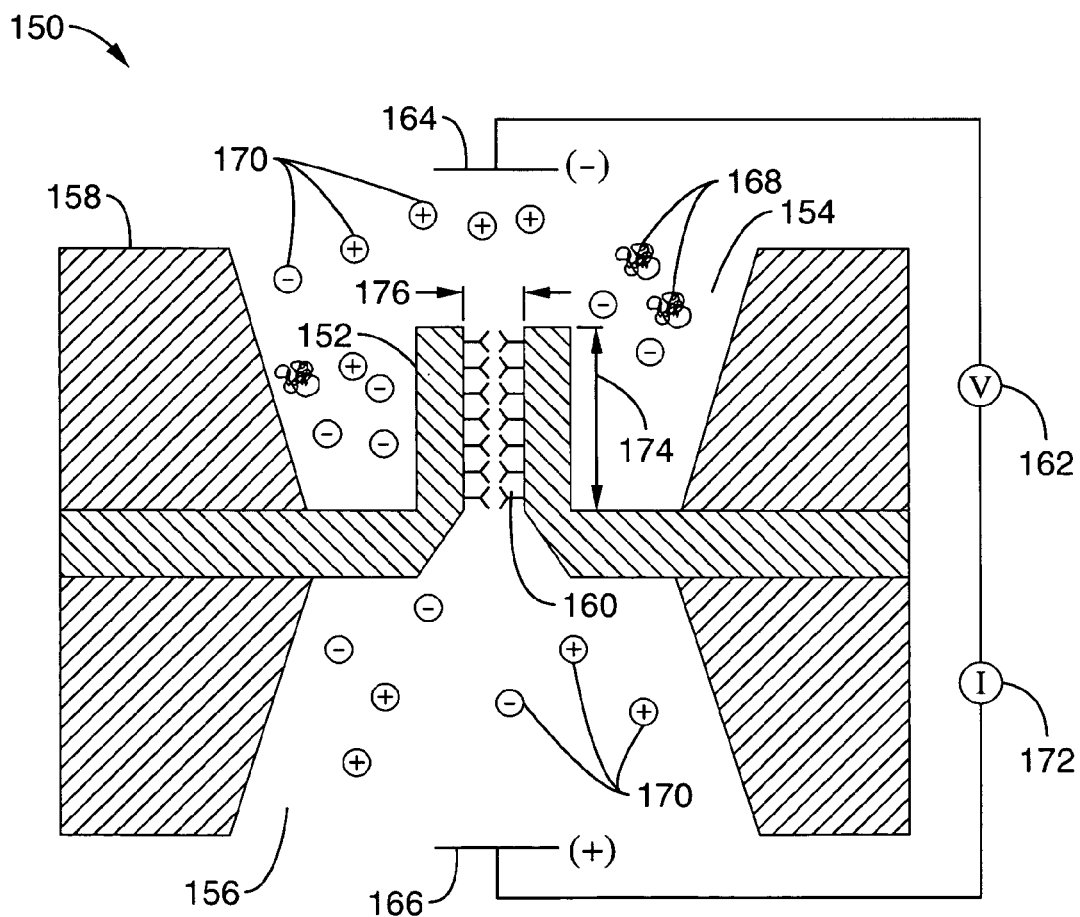
FIG. 28 is a schematic of a nanocapillary (i.e. $SiO_2$ or GaN) according to an embodiment of the present invention, shown bounded by fluidic chambers on either side and functionalized with a select receptor molecule.

FIG. 28 illustrates an embodiment of a nanocapillary electrophoresis device 150. In this embodiment a single nanocapillary 152 made of $SiO_2$ or GaN is shown coupled fluidic chambers 154 (top) on either side, and 156 (bottom) formed within a wafer material 158. The nanocapillary is functionalized with a certain type of receptor molecule 160. By applying a bias voltage V 162 across nanocapillary 152 via electrodes 164 (−), 166 (+), various biomolecules 168 and ions 170 can be electrophoretically transported from top chamber 154 to bottom chamber 156. Ion current is registered by ammeter 172. The depth of fluidic chamber 154 to the top of nanocapillary 152 is given by a distance 174, which for this embodiment is approximately 1-10 μm. The diameter 176 of nanocapillary 152 for this embodiment is approximately 5-20 nm. It should also be noted that an ionic current can be induced between the source and drain electrodes without the application of a bias voltage, such as in response to a pressure differential or other force.

Figure 29:
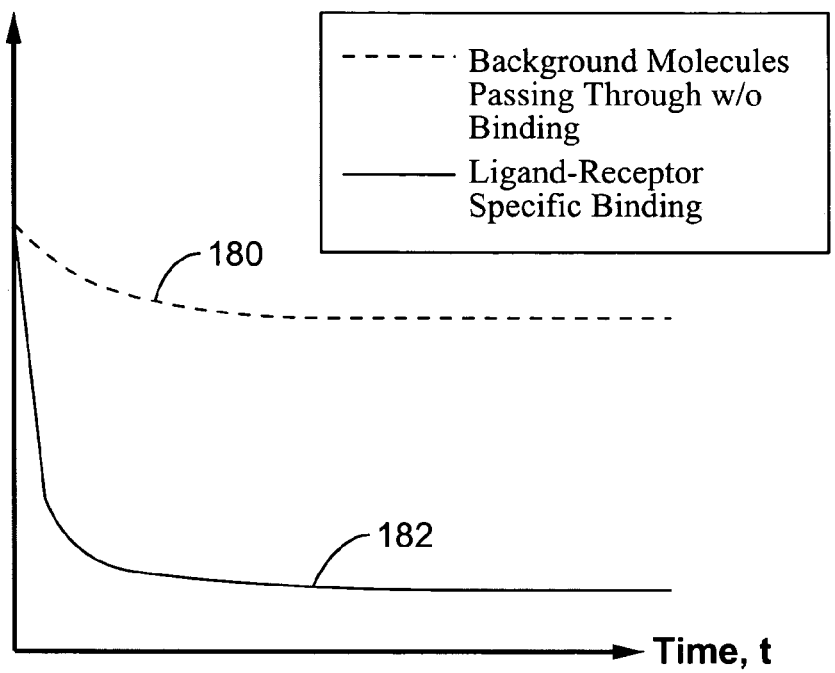
FIG. 29 is a plot of device current for the device of FIG. 28, shown in the case of binding and non-binding.

FIG. 29 is a plot of expected ion current for the device 150, as registered by ammeter 172. A first curve 180 is shown in response to background molecules passing through without binding. A second curve 182 showing a far more substantially current drop in response to specific ligand-receptor binding occurs inside nanocapillary 152. It should be noted that the ion current will drop much more than when biomolecules passes through it without specific binding.

The inner surface of these nanocapillaries in this embodiment are functionalized by probe/receptor ligands. A mixture of biomolecules in an ionic solution will be electrophoretically transported through the nanocapillary while the ionic current or the conductivity of the semiconductor tube is monitored. If a target ligand specifically binds to the probe molecules attached to the wall, the residence time of the ligand inside the nanocapillary will be much longer than that for non binding molecules passing through it. Because the nanocapillaries are on the order of molecular size (5-20 nm diameter), the ionic current will be modulated by the presence or absence of specifically-bound ligands as well as the molecule size. In addition, if there is any charge transfer between the analyte and the semiconductor GaN nanotubes, the conductivity of the tubes can be modified and monitored accordingly.

The concepts behind NEAT are a substantial departure from conventional gel or capillary electrophoresis, which rely on spatial separation of molecules based on their mass and charge, and requires a label to provide an optical signature. Recent work in the field has shown that by monitoring the ion current across a functionalized nanopore (1.5-4 nm inner diameter) formed by transmembrane protein ion channels, it is possible to detect single-molecule binding events with the specificity of single base-pair mismatches of DNA. While this offers the promising prospects of a label-free assay at the limits of sensitivity (single molecule) and specificity (single base pair mismatch), the use of bilayer lipid membranes and transmembrane ion channels poses difficulties with regard to fabricating arrays containing thousands of such devices for multiplexed analysis.

In view of the similarities in pore size between protein ion channels and the nanocapillaries described herein, the ion current through a nanocapillary would also be modulated by the presence or absence of specific ligand-receptor binding. This characteristic makes it possible to quantitatively detect ligand-receptor binding with specificity and sensitivity sufficient for cancer diagnostics and monitoring. Another important innovation in the present invention, is that an embodiment of the invention provides for fabricating large arrays, such as over 100×100 nanocapillaries within a 2 cm×2 cm silicon chip, within each nanocapillary functionalized by a different molecule and having its own microfluidic and electronic input/output system to deliver analytes and detect ionic and source drain currents. The ability to utilize such a chip provides the ability to quantitatively assay literally thousands of biomolecules simultaneously.

Nanotube Synthesis/Fabrication

The growth of robust non-porous nanotubes with uniform inner diameters would be advantageous in potential nanoscale electronics, optoelectronics, and biochemical sensing applications.

There are several desired design criteria for the nanotubes whose fabrication is addressed herein: (1) controlled inner diameter from 1-100 nm; (2) structural robustness, ideally continuous, non-porous and seamless; (3) easy functionalization of inner and outer surfaces; (4) chemically stable; (5) variable length; (6) electrical characteristics (insulating versus semiconducting). Carbon nanotubes and other tubular structures (BN, sulfides) might not be ideally suitable for this purpose for not satisfying some of the requirements. Recently, at least one group has been using the tubular structures prepared using solution templating process (porous alumina as templates) for biological separation purposes. Although this approach has met with some success, the nanotubes prepared this way are not robust and lack integrity making their use problematic for single nanocapillary applications. This aspect of the invention describes a novel process for making the targeted nanotubes that will satisfy all the above requirements for the nanofluidic sensing applications described herein, as well as other nanotube and nanofluidic applications. This novel process uses semiconductor nanowires as templates for the formation of nanotubes.

Vapor-Liquid-Solid Nanowire Growth

Nanostructures with reduced dimensionality such as nanowires are both fundamentally interesting and technologically important. Among all chemical approaches, the vapor-liquid-solid (VLS) process seems to be the most successful one for generating nanowires with single crystalline structures and in large quantities. This process was previously employed to produce micrometer-sized whiskers in the seventies, and more recently nanoscale wires and rods with various compositions. The process starts with the dissolution of gaseous reactants in nanosized liquid droplets of the catalyst metal, followed by nucleation and growth of single crystalline wires or rods. The catalyst could be easily selected based on an analysis of the equilibrium phase diagrams. The methodology is versatile and can be readily applied to synthesis of monocrystalline nanowires of other III-V and II-VI materials. In this embodiment Si nanowire arrays and ZnO nanowire arrays have been selected as templates for nanotube growth.

Epitaxial Casting Approach

The synthesis of single crystalline nanocapillaries with inner diameters of 30-200 nm and wall thicknesses of 5-50 nm has been demonstrated using this methodology. In this epitaxial casting process, hexagonal ZnO nanowires were used as templates for the epitaxial overgrowth of thin GaN layers in a chemical vapor deposition system. The ZnO nanowire templates were subsequently removed by simple thermal reduction, etching and evaporation, resulting in ordered arrays of GaN nanocapillaries on the substrates. Arrays of ZnO nanowires were grown on (110) sapphire wafers using a vapor deposition process developed by the inventors in the lab. These ZnO nanowire arrays are placed inside a MOCVD reaction tube for GaN chemical vapor deposition. Trimethylgallium and ammonia are as precursors and fed into the system with argon or nitrogen carrier gas. The deposition temperature was preferably set at 600-700° C. After the GaN deposition, the samples were treated at approximately 600° C. with 10% H in argon to remove the ZnO nanowire templates.

The starting ZnO nanowire arrays have uniform lengths of about 2-5 μm and diameters of about 30-200 nm. They are well-faceted with hexagonal cross-sections, exhibiting (110) planes on the sides. After the GaN deposition and template removal, the color of the sample turns from white to yellowish or darker. The morphology of the initial nanowire arrays was maintained, except for the increase in the diameters of the resulting nanostructures.

It was found that the majority of the nanostructures are tubular with uniform wall thicknesses. The nanocapillaries have inner diameters ranging from approximately 30-200 nm, similar to the ZnO nanowire arrays, and wall thicknesses between 5-50 nm. Most of the tubes have only one end open, however, tubes with both ends open were also observed.

This vanishing template process is shown in the sequence of FIGS. 4A, 4B and 4C. In FIG. 4A, a nanowire is used as a template to grow a coating of a different material as shown in FIG. 4B. The nanowire is then etched to yield a nanocapillary as shown in FIG. 4C. A scanning electron micrograph of an array of GaN nanocapillaries made by etching ZnO nanowires was shown in FIG. 5B and FIG. 7A. From the transmission electron micrograph of the GaN nanotubes it is found that the inner diameters are approximately 30-200 nm, wall thicknesses 5-50 nm and lengths 2-5 µm.

These observations are consistent with our SEM studies, where round-shaped and less-facetted ends are observed after the GaN coating. It is thus concluded that those open nanocapillary ends are originally located at the GaN and substrate interface, which were fractured open during TEM sample preparation. TEM studies also indicate that the inner cross-section of the nanocapillaries remains pseudo-hexagonal after template removal.

The successful preparation of single crystalline GaN nanocapillaries using this "epitaxial casting" approach suggests that it is possible to prepare single crystalline nanocapillaries of inorganic solids that have non-layered crystal structures. This new class of semiconductor nanotubes/nanocapillaries could offer great opportunities for further fundamental research as well as technological applications in nanoscale electronics and optoelectronics. Particularly important for fabricating the class of devices described herein is: (1) robustness of these semiconductor nanotubes; (2) uniform inner diameters; and (3) inner walls which can be readily functionalized and the availability of both tube ends being made accessible to fluid reservoirs for quantitative measurement.

Thermal Oxidation and Etching Approach

Another approach uses silicon nanowire arrays as templates. The process starts with thermal oxidation of the Si nanowire arrays which results in arrays of thin Si nanowires sheathed by thick layer of silicon oxide. This oxidized nanowire array is then selectively etched with XeF to remove the silicon nanowire cores, leaving an array of ordered silicon dioxide nanotubes with controllable inner diameters. This inner diameter will be controlled by the initial diameters of the silicon nanowires and the thermal oxidation process.

One form of nanocapillary synthesis has been shown in the sequence of FIG. 18A through FIG. 18G. In general the nanocapillaries are created by fabricating Si nanowire arrays, oxidizing them to form a $SiO_2$ cladding, and then etching the inner core of Si leaving a $SiO_2$ nanocapillary. Representative images of an SEM image of a Silica nanotube array is shown in FIG. 19D, with transmission electron micrographs in FIG. 20A and FIG. 20B showing $SiO_2$ nanocapillaries 5-50 nm in diameter, having inner diameters of 5-20 nm and being about 1-10 µm long.

With further optimization and control of the oxidation and etching process, it is expected that nanocapillaries can be formed with inner diameters of less than 5 nm. One major advantage of these nanocapillaries over those prepared using a porous alumina template is that the silica wall is made of condensed silica instead of porous silica, which is commonly the case when sol-gel chemistry is used. In addition, the inner surfaces of the current silica nanocapillaries are very smooth and their sizes are adjustable from 1-100 nm, which is particularly well suited for the current applications. In addition, the silica surface chemistry is readily available for covalent attachment of desired receptors on the inner wall of the nanocapillary. Hence, the GaN and silica tubes should satisfy all the requirements for the proposed nanofluidic sensing applications.

Fabrication of NEAT Device Using Silica Nanotube

It is important to be able to predict the ionic current/as a function of applied bias voltage V for a given nanocapillary length L and diameter d. This requires a theory for modeling electrophoretic fluid transport in nanocapillaries. However, this is a complex issue and a topic of intense current research. The forces that control intermolecular interactions between a hydrophilic surface and water are hydration, electrostatic, and Van Der Waals forces. Hydration forces, which originate from steric interactions resulting from hydrogen bonding of water to a polar surface, generally occur between 1-2 nm. Electrostatic forces resulting from osmotic pressure of counterions near a charged surface typically range from 1-50 nm (Debye length), depending on the bulk ion concentration. Finally, Van Der Waals forces range between 1-50 nm as well. Therefore, it is clear that nanocapillaries, with diameters in the 5-20 nm, fall within the range of these surface and intermolecular forces. Therefore, continuum theories of fluid transport are invalid for these length scales. Solutions of the Poisson-Boltzmann equation to determine equilibrium ion distributions in nanopores can yield grossly incorrect results. In addition, 5-20 nm is a range of length scales that is intractable by molecular dynamics simulations (generally used for 1-5 nm) as well. Hence, statistical mechanical models based on Monte Carlo simulations or Brownian dynamics are generally utilized for modeling transport. At present, there are no design rules for predicting I-V (current-voltage) characteristics as a function of nanocapillary geometry. Hence, simple arguments will be utilized as outlined below to provide some general guidelines, or "rules of thumb", for nanocapillary design.

From past nanopore experiments it is clear that the electrical resistance of the α HL nanopore is about $10^9 \Omega$. The resistance comes from the constricted geometry of α HL nanopore, whose length is about, L≈10 nm and diameter is, d≈1.4 nm. Many of the experiments were performed in 1M KCl or other monovalent ions. The mobilities of many common ions are listed in Table 1. The electrical conductivity σ in bulk water can be predicted as:

$$\sigma = \eta(\mu^+ + \mu^-)ze \quad (1)$$

where η is the ionic concentration, $\mu^+$ and $\mu^-$ are the mobilities of cations and anions, respectively, z is the valence, and e is the charge of an electron. For 1M KCl solution, the electrical conductivity is predicted to be 15.5 $\Omega^{-1} m^{-1}$. Assuming that this value for bulk conductivity could be used for a nanopore, the electrical resistance of a nanopore can be estimated as:

$$R \approx \frac{L}{\sigma d^2} = 0.32 \times 10^9 \Omega \quad (2)$$

While this value is a factor of three smaller than that measured, yet it predicts within the right order of magnitude despite the assumptions.

Although such an approach cannot be used to accurately design nanocapillaries, one could use this approach as a guideline or "rule of thumb". For example, if we are using a 1M KCl solution and we would like to design our nanocapillary with a diameter d=20 nm for an electrical resistance of $10^9 \Omega$, the length can be obtained using Eq. (2) to be L≈6 µm. Hence, for a bias of 1 Volt, such a nanocapillary would produce about 1 nA in ionic current.

Figure 30:
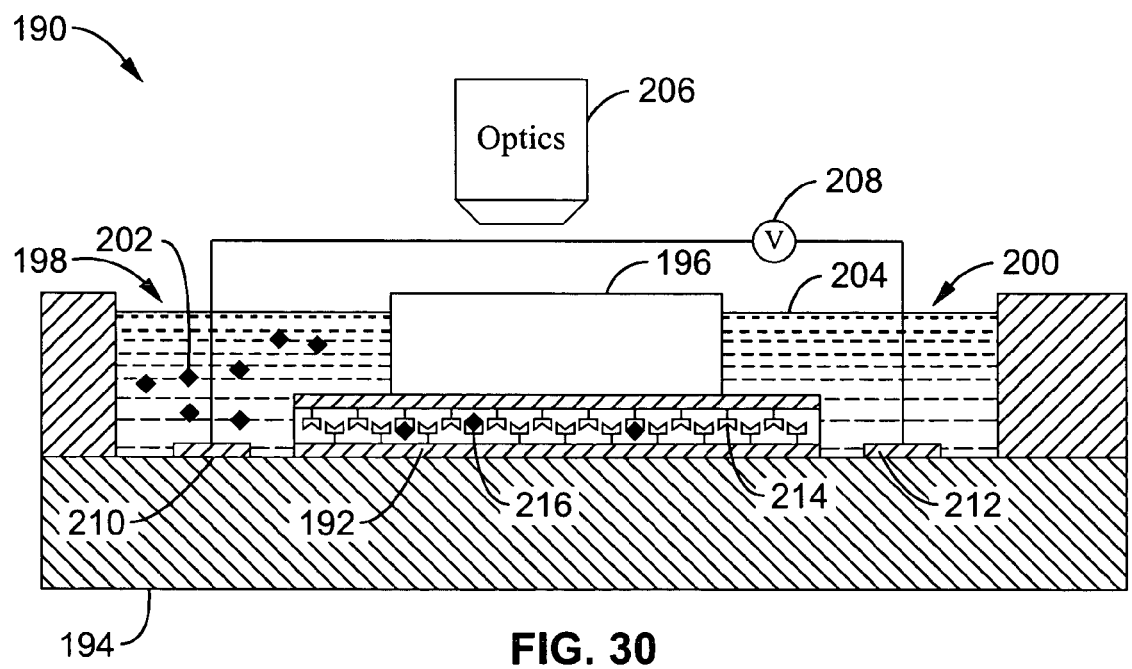
FIG. 30 is a schematic of a nanocapillary laid out on a silicon wafer according to an embodiment of the present invention, showing electrophoretic transport of analytes between microfluidic wells through the nanocapillary.

FIG. 30 illustrates a schematic diagram of a test system 190. $SiO_2$ nanocapillaries 192 are suspended in a solution and spread over (spin cast) on a silicon wafer 194. The nanocapillary being preferably fabricated according to the above techniques. After noting the location of an individual nanocapillary through an optical or an electron microscope 206, a hydrophobic polymer 196 (e.g. photoresist such as SU8 or PDMS) is preferably spun cast on the surface and patterned to open two microfluidic wells 198, 200 at either end of nanocapillary 192. Such an approach (spin cast and lithographically connect) is well established in our group to make electrical connections to nanowires and nanotubes. An ionic solution 202 is introduced in one of the microfluidic wells with deionized water 204 on the other side. A voltage (V) 208 is applied across the nanocapillary and the current (I) is measured between electrode 210 and electrode 212. By noting the I-V characteristics, the diameter of the nanocapillary can be estimated using the calculations discussed above. The nanocapillary is then electrophoretically washed in a dilute ionic solution and then heated to remove water from within the nanocapillary.

Nanocapillary Functionalization

The following embodiments are created using model antibody-antigen interaction within the nanofluidic system. The immobilization of the capture molecules is an important aspect of these experiments and should satisfy the following conditions: (i) the molecules must be preferentially attached to the inner surface of the nanocapillary; (ii) their receptor regions (epitopes) must be exposed for binding to take place; (iii) they should be strongly linked to the nanocapillary surface so that they do not get washed away or removed during binding.

The following is an example strategy for immobilizing antibody and nucleic acid capture sequences on inner surface of the nanocapillary. After dying the nanocapillary device, capillary forces are relied upon to draw in an aqueous solution. If already hydrated, washing and rinsing steps as described below are carried out by introducing new solutions in the microfluidic I/O wells and electrophoretically transporting the solution to the nanocapillary. A general surface functionalization procedure would be as following: (i) react inner surface of $SiO_2$ nanocapillary with diluted solution of 3-aminopropyltrimethoxysilane (APS) in pure methanol; (ii) after removal of excess APS by methanol rinse, react with the heterobifunctional crosslinkers, and followed by the attachment of thiolated DNA on the surface.

The following general steps are followed for proteins: (i) react inner surface of $SiO_2$ nanocapillary with solution of Mercapropropyltrimethoxysilane (MPS) in pure methanol; (ii) remove excess MPS by rinsing in methanol; (iii) take proteins separately and react with a heterobifunctional crosslinker, such as either Sulfo SMCC or Sulfo-GMBS, or similar, and remove the excess crosslinkers using a size-exclusion column; (iv) react the modified proteins with the silanized $SiO_2$ and remove unreacted proteins by washing.

After the nanocapillary is functionalized with the crosslinker molecules, a solution of the capture molecule 214 is introduced in one of the microfluidic wells and electrophoretically flowed into nanocapillary 192, and incubated for the covalent binding to occur. It should be emphasized that the surface functionalization chemistry can be generally applied to many other diverse chemical and biological systems which would allow us to easily establish a database for sensing with our proposed nanofluidic systems. This is largely due to the fact that the inorganic nanotubes can be readily functionalized with simple chemistry, unlike for example carbon nanotubes.

Electrical Measurement System

Once nanocapillary 192 is functionalized with receptor molecules 214, the binding tests start by first introducing the analyte solution in one of the microfluidic wells 198, 200. A direct current (DC) voltage bias $V_{dc}$ is applied across nanocapillary 192 and current $I_{dc}$ measured between electrodes 210, 212 as a function of time. Ions 202 passing through nanocapillary 192 are bound 216 to capture molecules, which alters the current flow through the nanocapillary.

Figure 31:
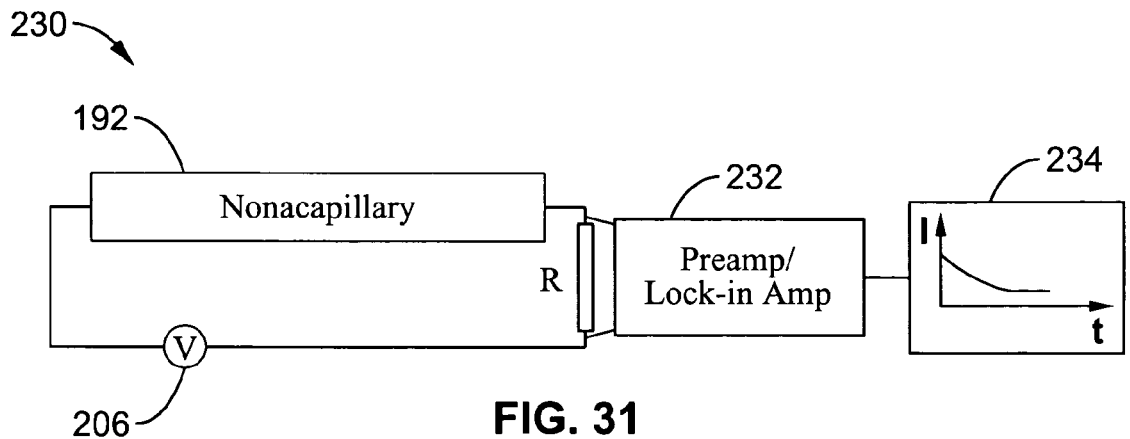
FIG. 31 is an electronic schematic configured for measuring nanocapillary ionic current for embodiments of the present invention.

FIG. 31 illustrates a simple electronic circuit 230 for measuring nanocapillary ionic current. Voltage across resistor R, whose resistance is much less than nanocapillary 192, is amplified and processed using a computer (not shown) to plot I-t 234.

The voltage drop across a resistor R, whose resistance is much less than that of the nanocapillary, is shown being amplified by pre-amp/lock-in amplifier 232. To obtain accurate measurements, it is important to provide a high signal-to-noise ratio within the system. There are three basic sources of noise within the system: Johnson noise, shot noise of the nanocapillary, and noise (1/f, Johnson, shot) of preamplifier 232. While DC measurements are simple, they are subject to more noise primarily because of the 1/f noise and large frequency bandwidth (typically >1 kHz). For example, if it is found that some binding events that occur in the 1-10 mS range, the bandwidth can for instance be configured on the order of 0.1-1 MHz to capture those events. Since the noise voltage, $V_n$ increases with bandwidth as $V_n \propto \sqrt{\Delta f}$ higher bandwidth can lead to low signal-to-noise ratios.

A low-pass filter, which can be preferably programmed within preamplifier 232, can remove 1/f noise if the minimum frequency is kept higher than about 200 Hz. If the signal-to-noise is still not sufficient, a small AC bias $V_{ac}$ at frequency $f_0$ can be superimposed on the DC bias $V_{dc}$. This step allows a lock-in amplifier 232 to lock-in to the current $I_{ac}$ that is modulated at $f_0$ and reduces the bandwidth $\Delta f$ to much smaller values, thereby reducing noise. The frequency $f_0$ can be chosen to be higher than where 1/f is dominant, thus enabling measurements limited only by shot and Johnson noise.

Single Molecular Imaging Within Individual Nanotubes

As discussed above, the test device (FIG. 30) utilizes a transparent photoresist 196 for defining the microfluidic wells. This provides optical access to image the nanocapillary. The use of fluorescently labeled probe molecules (capture sequence ssDNA or antibodies) can be helpful in ensuring that receptors enter the nanocapillary and remain bound to the surface. Once the probe molecules are seen to coat the inner surface of the nanocapillary, the fluorescent probes are bleached away, such as by using higher laser powers to reduce undesirable background. It can also be advantageous to use fluorescent labels of a different color for the ligand that binds to the receptor, and fluorescent labels of a third color for a background molecule. These fluorescent labels enable dissecting the processes occurring inside the nanocapillary by imaging the transport or binding of receptors, ligands, and non-binding molecules.

Advances have been rapidly made in the detection, identification, and spectroscopy of single-molecule species, wherein the sensitivity of the state-of-the-art optical detection in room-temperature solutions is such that characteristics of laser-induced fluorescence (LIF) from individual molecules can be utilized for accurate identification of chemical species. Molecular characteristics amenable to single-molecule detection (SMD) include spectrum (color), quantum yield (fluorescence intensity) excited-state lifetime, and anisotropy.

Further enhancement of optical identification can be achieved by a combination of two or more of the optical traits of sample molecules offering the prospect of ultra-sensitive optical sensing of chemical species. One aspect of the invention is the integration of the NEAT technology with optical single-molecule detection and identification. The overall sensitivity is expected to reach the single-molecule level. Furthermore, system performance such as the true-positive rate is anticipated to improve greatly by complementing molecular sizing of electrical signals with spectroscopic signatures.

Figure 32:
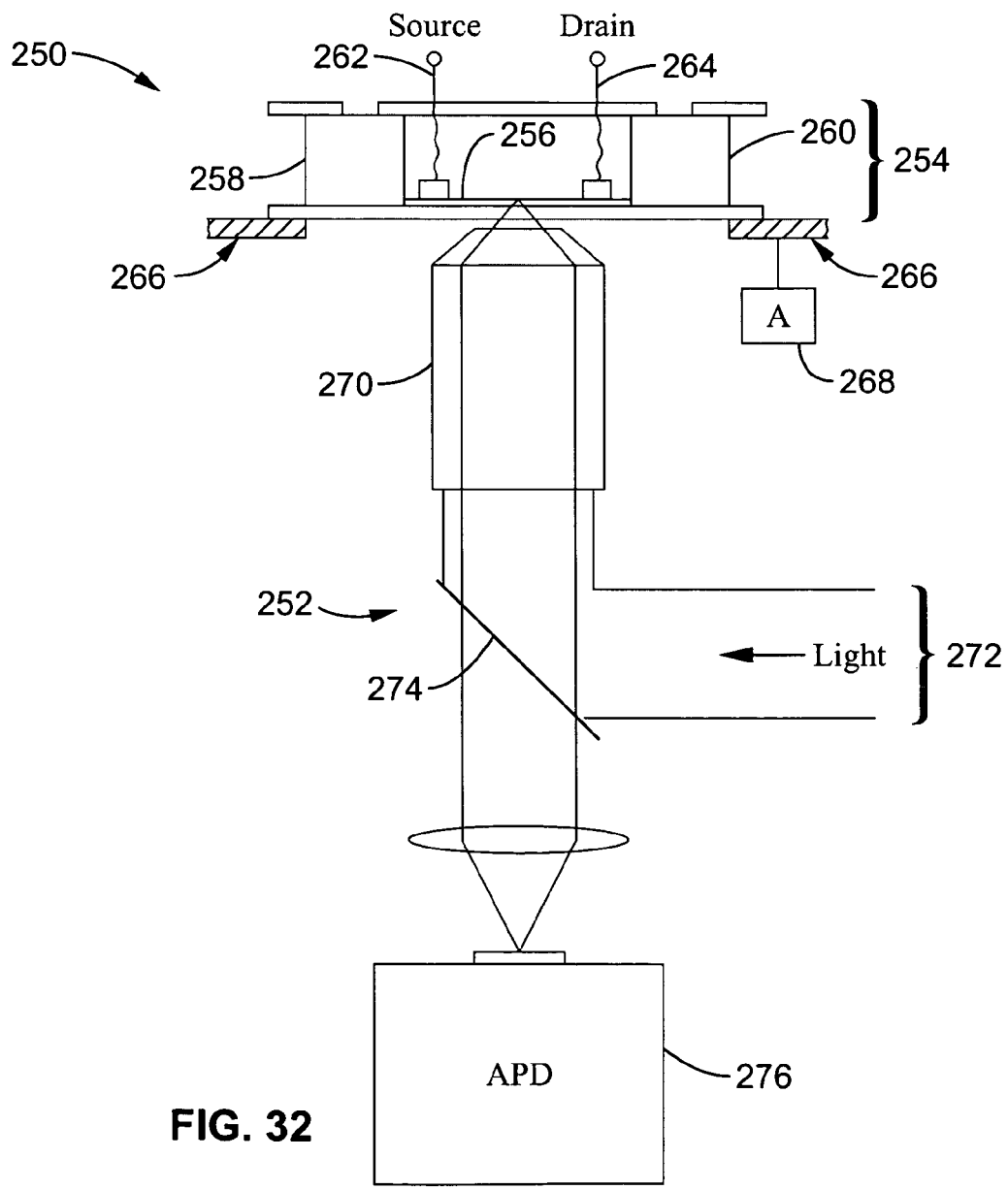
FIG. 32 is a schematic of an integrated NEAT-SMD system according to an aspect of the present invention, shown being tested on a single-molecule microscope.
Figure 33:
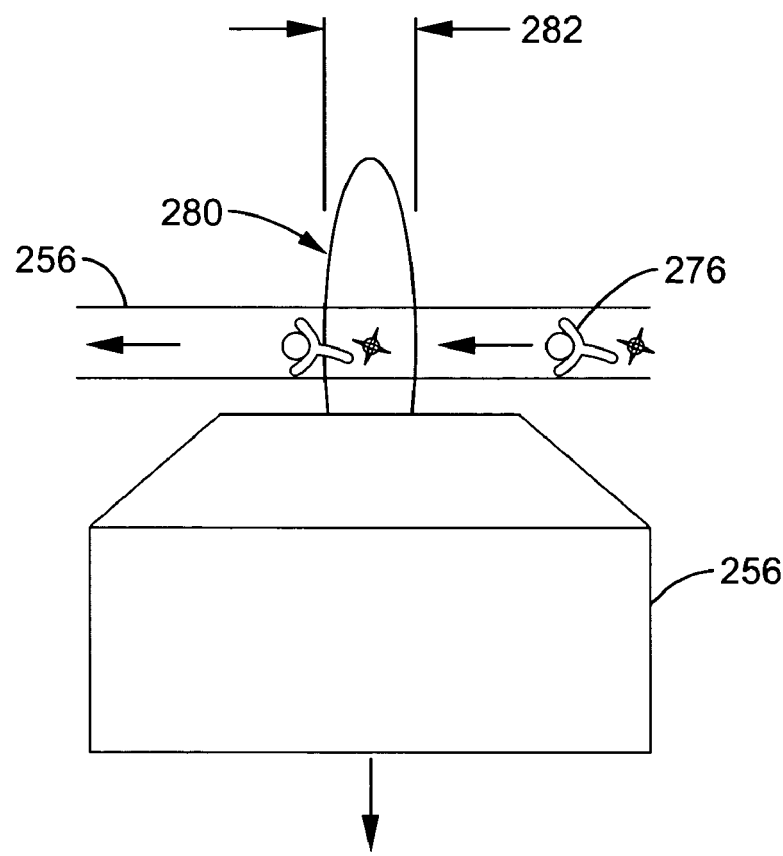
FIG. 33 is a detailed view of the system of FIG. 32 showing the antigen/antibody complex passing through the focal area of the single-molecule microscope.

FIG. 32 and FIG. 33 illustrate an integrated NEAT-SMD system 250, with FIG. 33 being an enlargement (zoom) of the optical excitation and detection volume. The combined electronic and optical measurements are conducted on a single-molecule (SM) microscope 252. Briefly, the NEAT sample 254, with nanocapillary 256 is retained between two reservoirs 258, 260 on a substrate. A source lead 262 and drain lead 264 are coupled to nanocapillary 256. The substrate (i.e. glass) of NEAT sample 254 is secured on movable stage 266 coupled to an actuator 268. For the sake of illustration, the stage is shown under the NEAT substrate, although it is preferably mounted on the top of microscope objective 270. By way of example a computer-controlled piezo translation stage may be utilized which provides sub-nanometer spatial resolution. The NEAT-stage assembly is preferably coupled to an objective 270, for example an oil-immersion, high numeric aperture (N.A.) microscope objective, typically of N.A.=1.4. An excitation laser beam 272 is guided by a dichroic mirror 274 to focus at the sample through objective 270. Fluorescence photons are collected by the same objective, spectrally filtered, and refocused onto a high sensitivity avalanche photodiode (APD) 276. In one embodiment of the invention a computer synchronizes the photon detection and stage movement to find a NEAT unit, and places the excitation/detection focal area 280 (FIG. 33), shown approximately 300 nm in diameter 282, at a suitable position along nanotube 256. Consequently, when a single chromophore-labeled antigen-antibody complex 276 passes through the focal area, a burst of photons is detected and recorded to yield an SM time trajectory as depicted in FIG. 34.

Figure 34:
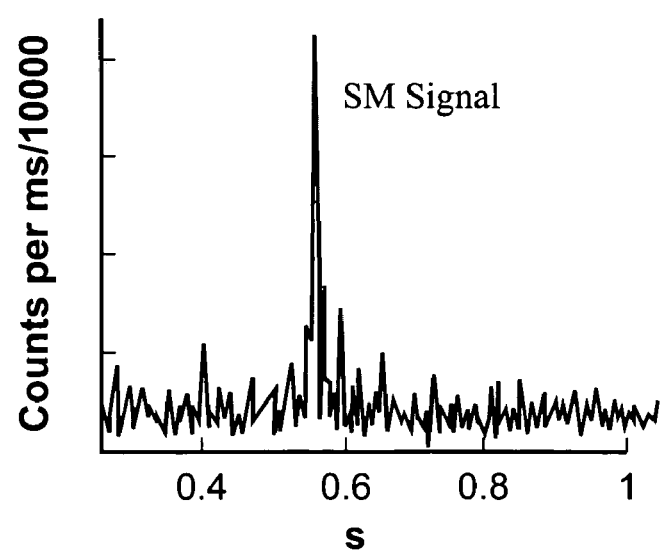
FIG. 34 is a plot of a typical SM trajectory for the system of FIG. 32-33.

A typical SM trajectory measured from diffusing dye-biomolecule conjugates is displayed in FIG. 34, where a burst of photons occurring at ~0.55 seconds corresponds to a single BSA dye conjugate (BSA=bovine serum albumin) diffusing through the focal volume. The background of ~5,500 cps (counts per second) mainly arises from water Raman scattering at the focal volume ($\sim\pi\times(100\ nm)^2\times(1\ um)$). In our NEAT detection, the Raman background will be suppressed by ~10 to 20 folds by virtue of the greatly reduced excitation volume (defined by nanocapillary's diameter, ($\sim\pi\times(100\ nm)^2\times(100\ nm)$). The NEAT-SMD within the present invention represents a significant advancement in sensing technology over the use of microfluidics technology and microcapillary detection.

One test embodiment utilizes the NEAT-SMD devices for identifying single-molecule true-positive events if-and-only-if both the drop of electric current and the influx of fluorescence photons occur concurrently. Such a coincident detection scheme can substantially decrease the false-positive identification rate, that may otherwise arise when either the NEAT or the SMD is used as the sole sensing source. For instance, the occasional photon "shot" noise (sharp spikes reaching 2,000 cps) along the trajectory in FIG. 34 may lead to dubious diagnosis if SMD is separately relied upon. Such false-positive assignments can be eliminated by utilizing coincident detection.

Figure 35:
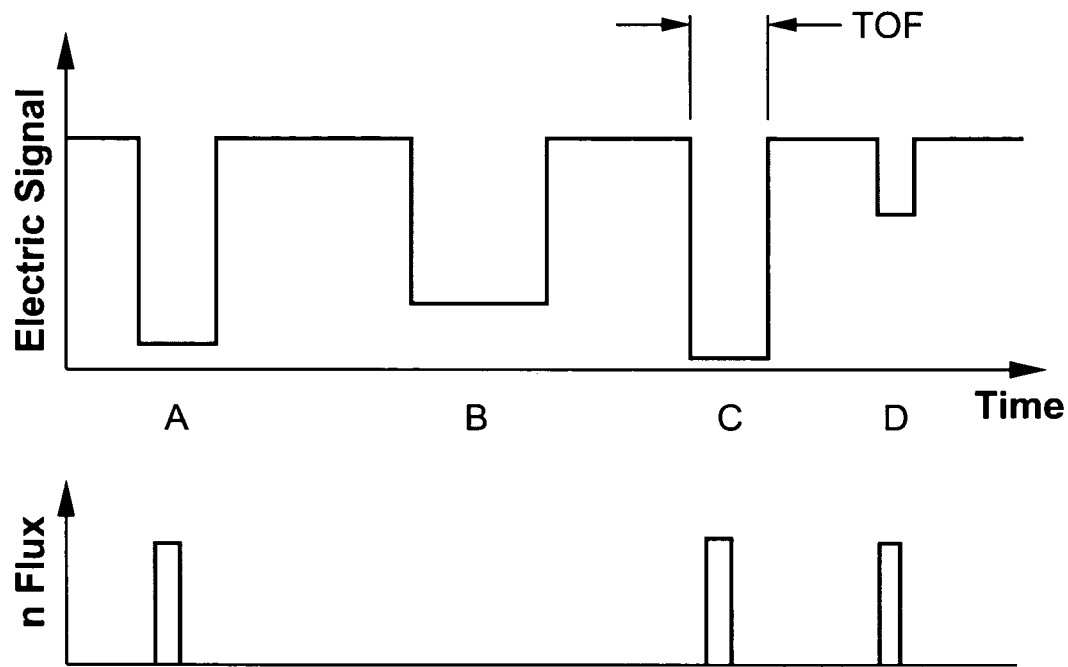
FIG. 35 is a plot of waveforms depicting coincident detection according to an aspect of the present invention which reduces the instances of false-positive assignments.

FIG. 35 illustrates an idealized NRA T-electric and SMD-optical coincidence sensing embodiment. True-positive events, denoted by A and C, are identified by correct TOF and coincident optical signal. B and D represent hypothetical false-positive events in practical applications. The former can be due to some non-specific aggregation of biomolecules, to be discriminated by the lack of the fluorescent marker. The latter can be due to fluorescent probes that do not conjugate to the target biomolecule, to be discriminated by the incorrect TOF signal. The following section describes some tests which characterize the sensitivity, dynamic range, efficiency, and specificity of the described NEAT-SMD.

DNA Sequence Detection

Figure 36:
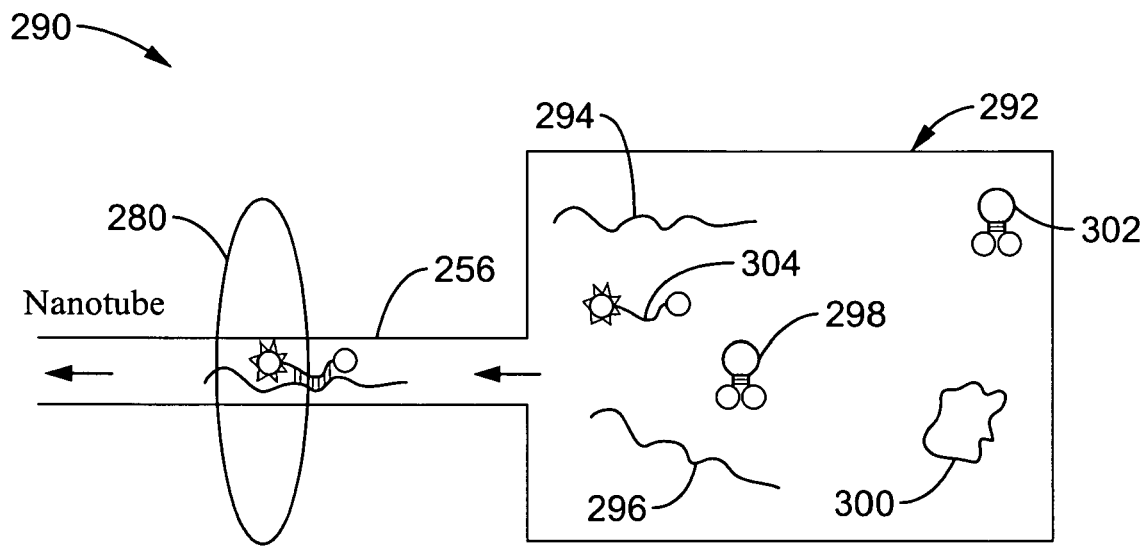
FIG. 36 is a schematic of NEAT-SMD DNA sequence detection according to an aspect of the present invention, showing target and non-target sequences in a reservoir prior to passing through the nanocapillary of the sequence detector.

FIG. 36 illustrates NRA T-SMD DNA sequence detection within nanocapillary 256 within excitation/detection focal area 280. Early detection of malignant DNA sequences is critical in diagnosis and prognosis of gene-related diseases such as cancer. Recently, a quantification of un-amplified DNA samples has been demonstrated with a sensitivity of ~$10^3$ copies/sample and a dynamic range of ~$10^4$, by combined gel electrophoresis and single-molecule imaging. In this regard, the NEAT-SMD sensing scheme described in the present invention may find applications in identifying specific DNA sequences at the single copy level. Referring to the figure, the reservoir 292 contains: (1) DNA fragments of both target sequence 294 and other sequences 296; (2) DNA hairpin molecular beacons containing complementary sequence 298 to the target DNAs; and (3) other biomolecules 300. The excitation/detection volume for SMD is represented by the ellipse.

The initial characterization of this application is exemplified as being carried out utilizing molecular beacons, where a sensing loop complementary to the malevolent sequence is sandwiched between two short stems of complementary sequences in a hairpin formation. In addition, a chromophore and a quencher are labeled respectively at either ends of the hairpin. In this way, the molecular beacon appears "dark" in its closed form 302 but becomes "bright" in its extended form 304 when complementing the target DNA sequence. The hairpin construct is designed such that the majority of beacons are in the closed form in equilibrium to minimize background counts. As discussed earlier, potential interfering agents including the non-target sequences, other biomolecules or non-complemented molecular beacons can be discriminated by the coincident NEAT-SMD detection scheme already described, thereby greatly reducing potential false-positive identifications.

A BRCA1 capture-probe gene sequence such as (5'-CACAACAAAGAGCATACATAGGG-3')

can be utilized for a test target. The molecular beacon containing a complementary primer can be obtained from commercial sources. The initial characterization involves the test target gene and the molecular beacons wherein the sensitivity of NEAT-SMD to single-nucleotide mutation is tested. Solvent conditions, such as ionic strength and metallic ion concentration, are varied systematically to optimize the detection condition. Later-stage development involves adding non-consequential DNA fragments as well as spectator biomolecules such as BSA. Due to the different nature of noise sources to which NEAT is subject (i.e. 1/f, Johnson, shot) and SMD (Poisson, shot), a fast, wavelet transform-based computer algorithm has been developed for the present invention that provides accurate recognition of coincident events.

Immunosensing

To demonstrate the potential of the NEAT-SMD concept in proteomics, the tests are carried out for antibody-protein recognition. Monoclonal mouse antibody, D1.3, will be labeled with fluorescent probes and used as the recognition agent for hen egg lysozyme. The initial phase of the test can utilize purified antibody and lysozyme. In analogy to the above-mentioned DNA testing, the solution conditions, such as pH and ionic strength, are varied systematically to optimize the sensing parameters. In the second phase, non-consequential proteins such as BSA are included to mimic conditions in practical applications where a crude cell extract is applied directly to the sensing reservoir. In negative control experiments, fluorescently labeled anti-BSA are utilized to detect a solution containing both egg lysozyme and BSA. The relative concentration of BSA and egg lysozyme are systematically varied to quantitatively ascertain the statistics; which can be an important step toward utilizing the present NEAT-SMD in clinical applications, especially in those that ascribe to evidence-based medicine. For potential applications, in addition to providing fast and quantitative detection of virulous proteins, the present NEAT-SMD concept may contribute to whole-cell proteomics, in which the number of molecules for a specific protein in a single cell can be accurately determined molecule-by-molecule.

Single Device Demo: TFET Using GaN Nanotubes

Importantly, the electrical and optical characteristics of these single crystalline GaN nanotubes are comparable to those of high quality GaN epilayers grown on ZnO substrates as well as those of GaN nanowires. Low temperature photoluminescence (PL) spectra of these nanotubes were measured using the fourth harmonic output of a YAG laser (266 nm) as an excitation source. No midgap yellow emission has been observed. The band edge emission was observed in these nanotube samples between 375 nm and 360 nm, with the thinner tubes emitting at shorter wavelengths. This slight blueshift of the emission may be attributed to the quantum confinement effect since some of the nanotubes have walls as thin as 5 nm, which is smaller than the exciton Bohr radius of GaN. Electron transport measurements indicate the resistances of these nanotubes are on the order of 10 MΩ at room temperature and increase with decreasing temperature, similar to those of high quality GaN nanowires. FIG. 17 illustrates an I-V measurement on single GaN nanotube at different temperatures.

Figure 37:
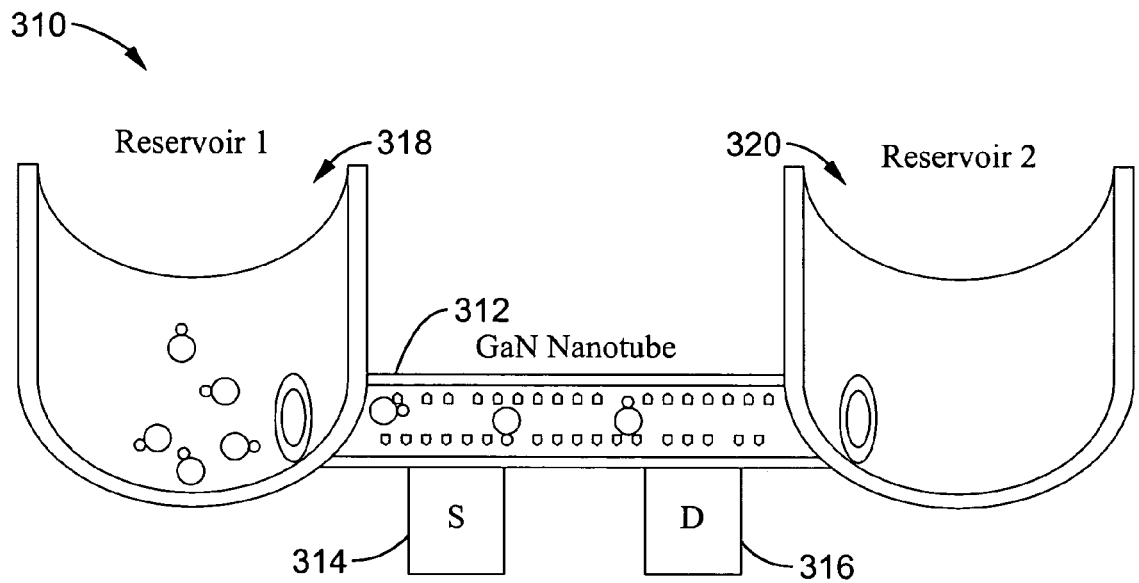
FIG. 37 is a schematic of a TFET device according to an embodiment of the present invention, showing the use of the internal surface only for an enclosed nanofluidic system.

FIG. 37. illustrates an embodiment of the TFET device 310 which uses the internal surface of nanocapillaries which lead to an enclosed nanofluidic system. A functionalized nanocapillary 312 having a source 314 and drain 316, is shown fluidly coupled to reservoirs 318, 320. It should be appreciated that prior to the present invention, semiconductor thin films have been extensively studied for their chemical and biological field effect transistor applications. Embodiments of the nanotubes described herein, such as the GaN nanotubes, have a number of characteristics making them particularly well-suited for use in such applications, including the following: mechanically robust, electrically and optically active, and extremely high internal and external surfaces. This second approach makes use of these characteristics for chemical and biological sensing within a tube-field-effect-transistor (TFET). The figure depicts a TFET having interface functionalization, along with design of microfluidics and reservoirs which can be largely similar to those described for NEAT. A difference between the TFET device in relation to the NEAT device, is that the source-drain current for the TFET is monitored instead of the ionic current as monitored for the NEAT device. It should be recognized that it is fairly common for different molecular species on the surface of the nanotubes to induce different surface charge/potentials and in many cases electron transfer. Either factor can induce the conductivity change within the semiconductor GaN nanotubes. More importantly, both the internal and external surfaces can be utilized as active interaction areas for the sensing purpose, which would dramatically increase the sensitivity of the proposed TFET device.

Another aspect of the present invention for TFETs (or NEAT), is to optionally measure ionic current simultaneously with source-drain current if desired. The simultaneous feedback of multiple electrical signals, optionally in conjunction with single molecular optical signals as detailed previously, allows performing chemical and biological sensing with extreme sensitivity, specificity and far lower false alarm rates.

Device Integration and Parallel Processing

This section describes the design and fabrication of an embodiment of a nanocapillary array chip according to the present invention. The integration of the devices into an array chip is important for providing parallel fluid processing.

This embodiment of the NEAT chip consists of an array of N×M cells, each cell containing a single nanocapillary that has two microfluidic chambers on either side, and the electronic system to detect the current from each of the cells. As described below, these chips comprise multiple wafers integrated together. The described embodiment contains three wafers integrated together: (i) a first wafer containing the nanocapillaries; (ii) a second wafer containing the microfluidics and electronic ground plane; and (iii) a third wafer containing the counter electrodes. These chips are then connected first to a MEMS switching chip and then to a CMOS electronics chip configured for processing the signals. As it would be difficult to fabricate the N×M nanocapillaries with the same geometry and electrophoretic behavior, an embodiment of the present invention is configured to measure the I-V characteristics of each cell in the presence of a reference non-binding molecule (e.g. BSA). This technique provides a reference signal for characterizing each of the nanocapillaries, wherein their responses to new molecular species can be normalized in response to the characterization data. Finally, it is contemplated that by performing binding assays for arrays of targeted chemical and biological species, a database of I-V characteristics should be created. The database preferably being irrespective of specific device characteristics of cells within the array, or be based on the characteristics of a hypothetical reference device (to which actual registered I-V information will be normalized). An embodiment of the database being configured for providing characteristics that correspond to a certain analyte concentrations, which can thereby form the foundation for quantitative assays.

Figure 38:
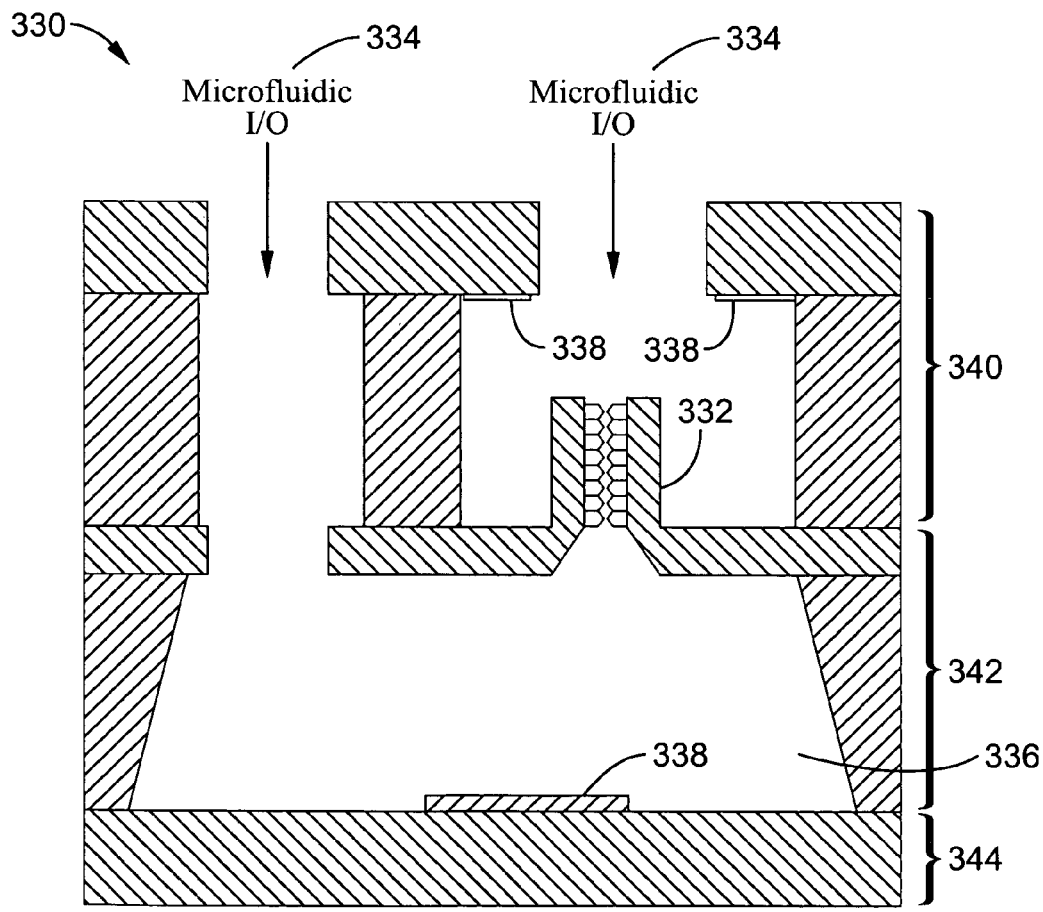
FIG. 38 is a schematic of an individual cell of a nanocapillary array chip according to an embodiment of the present invention, showing a side view of a three wafer fabrication process.

FIG. 38 illustrates an embodiment of a single NEAT cell 330 containing nanocapillary 332, microfluidic I/O 334, reservoirs 336, and electrodes 338. In this specific embodiment, each cell in the array is about 200 µm in size, thus allowing 100×100 cells in a 2 cm×2 cm array, however, it should be appreciated that it can be fabricated in a range of geometries to suit different applications. This embodiment of the NEAT chip is based on the integration of three wafers: microfluidic 340, nanocapillary 342 and electrode 344. Each of these wafers is preferably fabricated individually and then assembled either with adhesives or other low-temperature bonding techniques to form the NEAT array chip.

Figure 39:
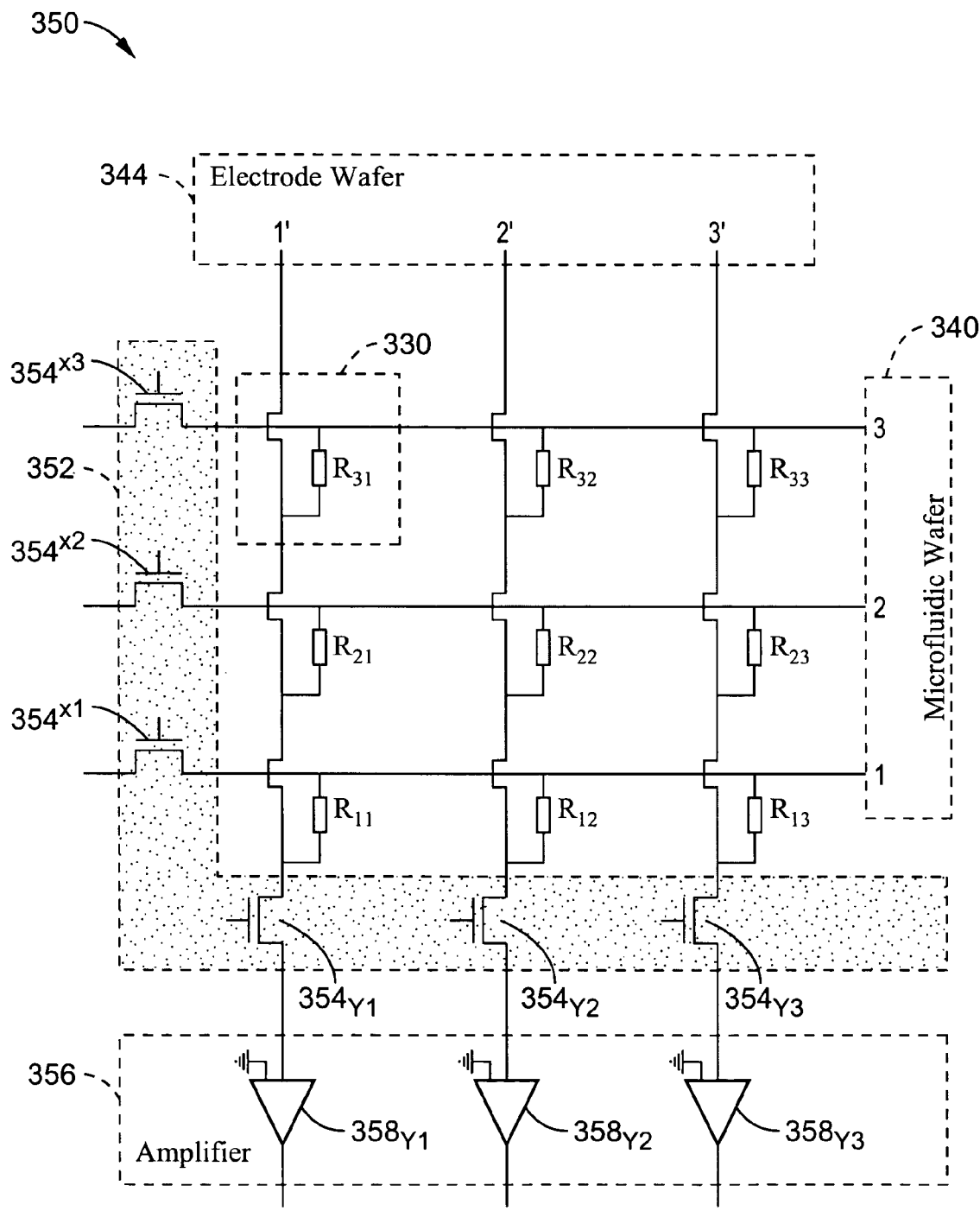
FIG. 39 is an electrical schematic of addressing an array of nanocapillary cells according to an aspect of the present invention, showing driving of each cell and measuring the I-V response across each nanocapillary junction.

FIG. 39 illustrates an embodiment of an electronic system 350 for addressing each cell, 330 from FIG. 38, and measuring the I-V of its nanocapillary shown as resistor $R_{ij}$. After the three-wafer NEAT chip is integrated (or alternatively during integration), it will be connected to a switching matrix 352 and to sense circuits 356. For example, the switching matrix may be embodied in a MEMS switching chip 352, having row switches (or drivers) 354x1, 354x2, 354x3 . . . 354xn, and column switches 354y1, 354y2, 354y3 . . . 354yn. Sensing circuit device 356 may for example comprise a CMOS electronics chip having a plurality of analog amplifiers 358y1, 358y2, 358y3 . . . 358yn which registers the voltages from the columns (or rows insofar as driver/receiver roles reversed), such as the signals being conditioned by amplifiers. The electronic layer may additionally comprise multiplexes, D/A converters, or other interface circuitry to simplify the connection of the device to a host circuit, such as within a microprocessor-based circuit assembly.

It should be appreciated that the MEMs switching chip 352 could be fabricated within one or more of the three wafers, such as within the electrode wafer, insofar as it can be protected from fluids and interconnected appropriately to the other electrode layer (microfluidic wafer) and to the external electronics. The purpose of the MEMS and CMOS chips will be explained below. A system as shown allows an entire row of cells to be measured simultaneously. The wafers according to this embodiment of the NEAT chips can be fabricated as follows.

Microfluidic Wafer

Figure 40A:
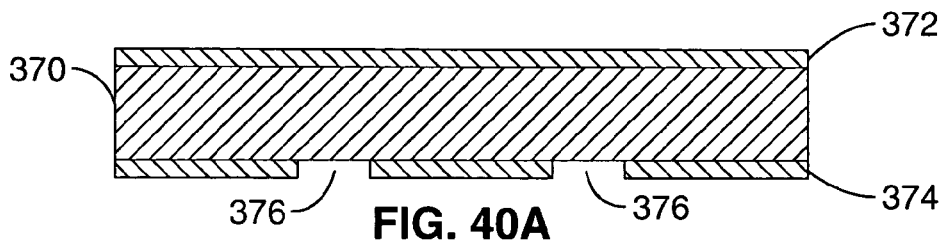
FIG. 40A-40E are cross-sections of microfluidic wafer fabrication according to an aspect of the present invention.
Figure 40B:
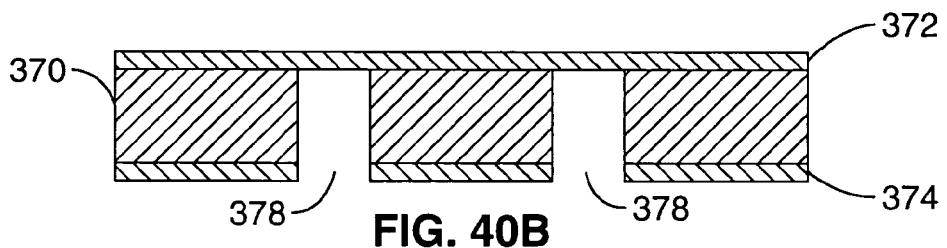
Figure 40C:
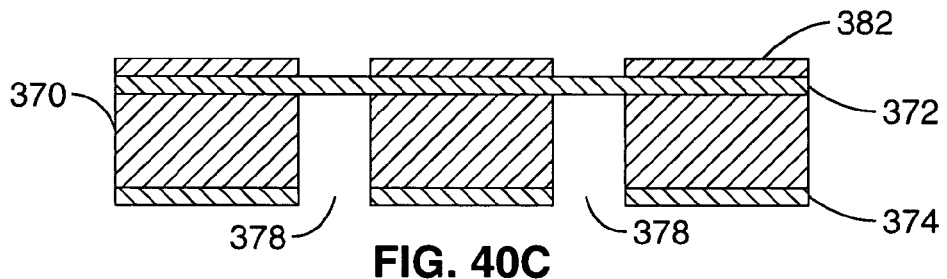
Figure 40D:
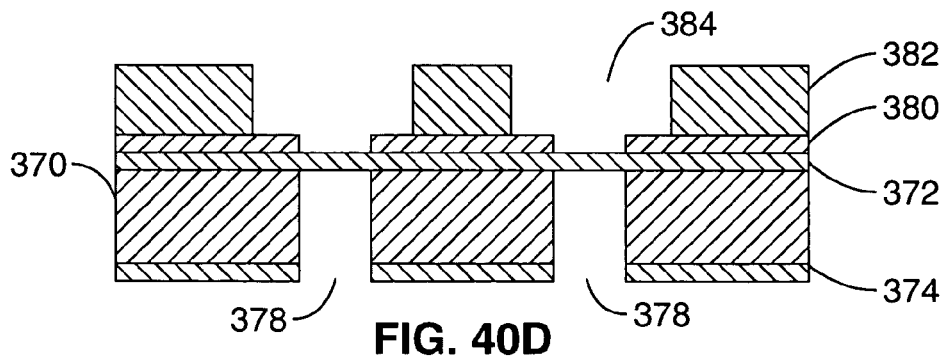
Figure 40E:
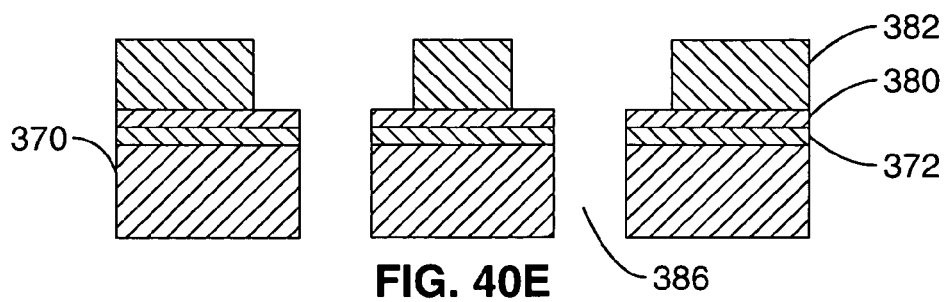

FIG. 40A through 40E illustrates a fabrication process which may be utilized to create the microfluidic wafer 340 (FIG. 38) within the array of NEAT 330 devices. In FIG. 40A, a silicon (Si) wafer 370 is first coated with silicon nitride ($SiN_x$) on a first side 372 and on a second side 374. The wafer is then patterned, such as on second side 376. In FIG. 40B the pattern 376 is used to create two through holes 378 per cell, such as using deep reactive ion etching (DRIE). The $SiN_x$ film on the other side is preferably utilized as an etch stop within this embodiment. In FIG. 40C a metal film (Pt) 380 is deposited on $SiN_x$ and patterned to produce the electrical interconnection lines (i.e. 1, 2, 3, . . . N) seen being coupled to the row and column switches 352 in FIG. 39. In FIG. 40D a thick film of photoresist (i.e. SU8 photoresist) 382 is applied over the metal film and then patterned to produce holes 384 that are aligned with holes 378 in the Si wafer. In FIG. 40E the $SiN_x$ is then etched away to produce through holes 386 for microfluidic I/O.

Nanocapillary Wafer

Figure 41A:
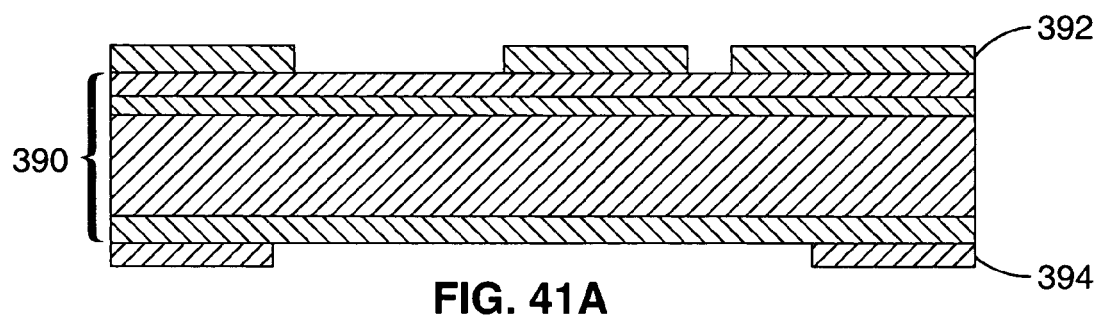
FIG. 41A-41G are cross-sections of nanocapillary wafer fabrication according to an aspect of the present invention.
Figure 41B:
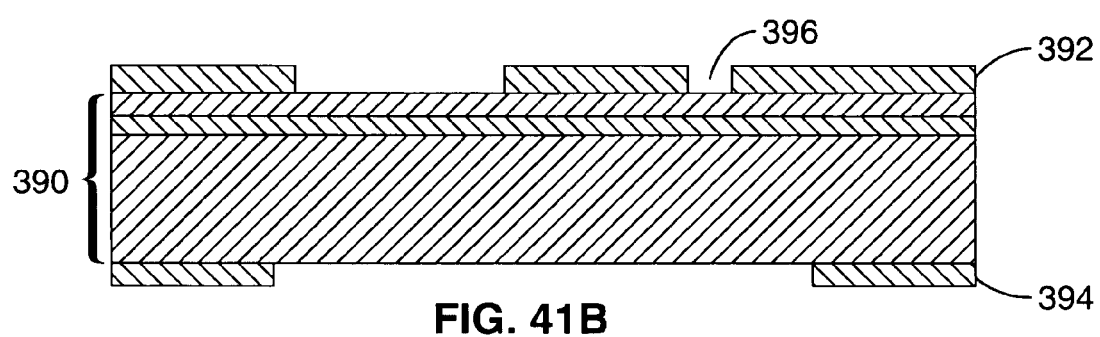
Figure 41C:
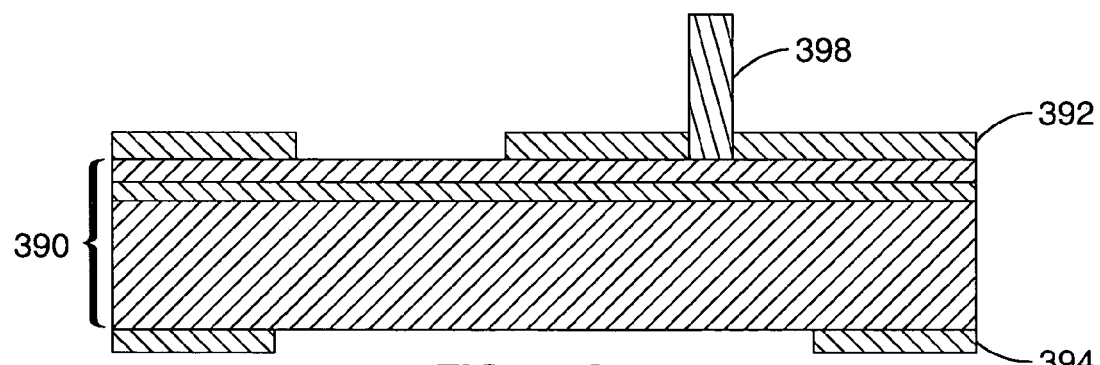
Figure 41D:
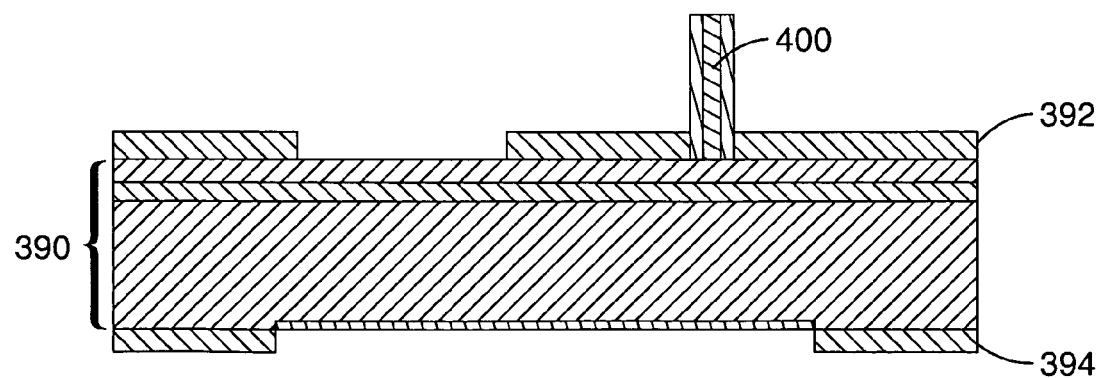
Figure 41E:
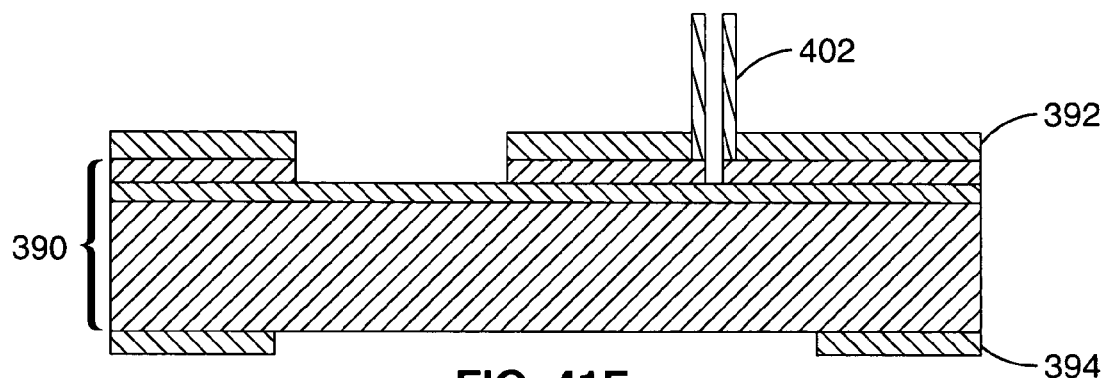
Figure 41F:
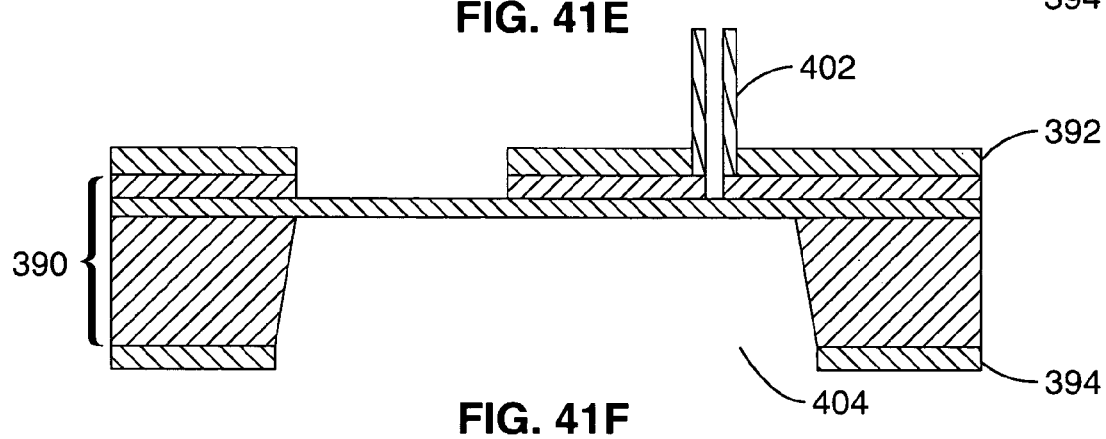
Figure 41G:
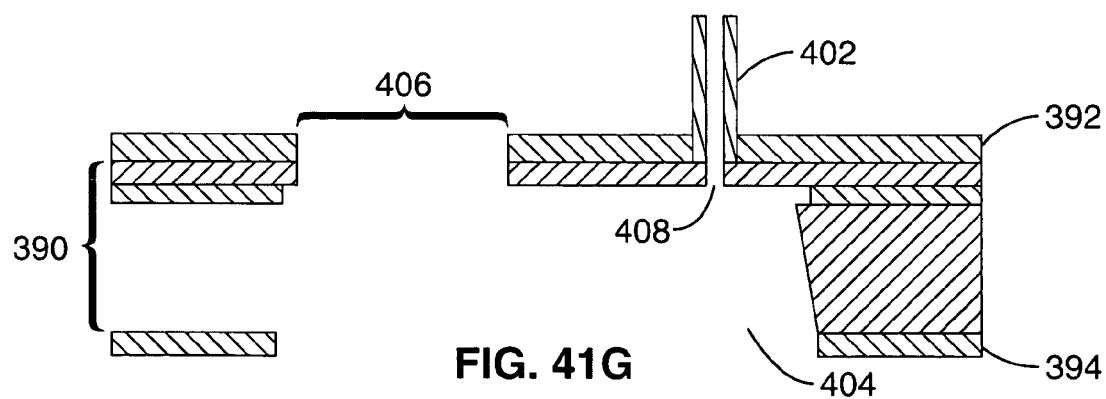
Figure 41H:
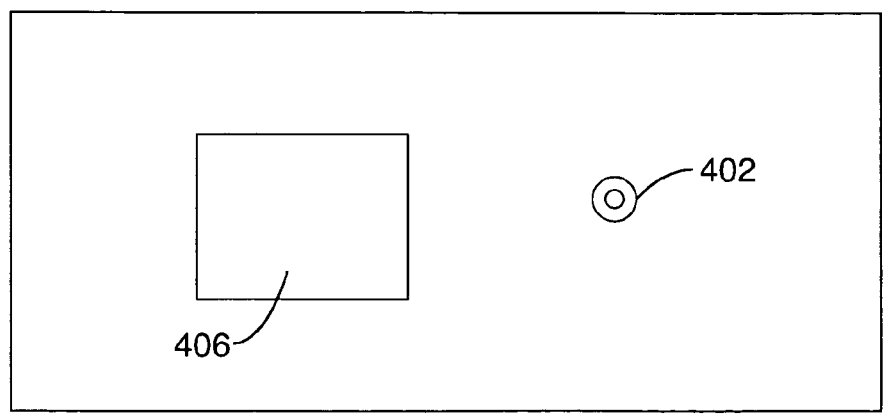
FIG. 41H is a top view of the nanocapillary wafer of FIG. 41A-41G.

FIG. 41A through 41H illustrate a fabrication process which may be utilized to create the nanocapillary wafer 342 (FIG. 38) of a NEAT 330 device (array). In FIG. 41A a silicon on insulator (SOI) wafer is coated on both sides with $SiN_x$ and then patterned on both sides. In FIG. 41B a thin gold film is deposited and patterned 396 so that it remains only within a small box (~1 µm×1 µm) confined by the $SiN_x$. This precaution prevents gold from diffusing when heated. In FIG. 41C a Si nanowire 398 is grown, such as by the chemical vapor deposition process described in a previous section. In FIG. 41D the Si nanowire 398, as well as exposed top and bottom Si surfaces, are thermally oxidized, leaving a Si core 400 in the $SiO_2$ nanowire. In FIG. 41E the top $SiO_2$ is removed by reactive ion etch and the bottom $SiO_2$ is removed by a brief wet etch in buffered HF. Subsequently, the wafer is exposed to XeF which etches exposed Si, including the Si core in the $SiO_2$ nanowire, leaving an $SiO_2$ nanocapillary 402. In FIG. 41F the rest of the exposed Si 404 is etched in TMAH, which selectively etches Si. In FIG. 41G the $SiO_2$ layer is etched from the bottom side, which creates the through hole 406 and creates an opening 408 to nanocapillary 402. FIG. 41H illustrates a corresponding top view of the this cell of the wafer after the fabrication step of according to FIG. 41G is performed.

Electrode Wafer

Compared to the microfluidics and the nanocapillary wafers, the electrode wafer is very simple since it contains only a pattern of M lines (1', 2', 3' . . . M), such as fabricated on either a glass or a Si wafer. Its fabrication will not be described herein, but could be performed by one of ordinary skill in the art with respect to the teachings provided herein.

MEMS Switching Chip

Referring to FIG. 39, each of the line or electrodes on the microfluidic wafer (1, 2, 3, . . . N) and the electrode wafer (1', 2', 3' . . . M) is connected to a switch. A set of input switches allow activating a particular row, wherein the switches on the columns can be selectively activated for registering characteristics of each NEAT cell. Hence, to address the nanocapillary $R_{23}$, one needs to turn on switch 354x2 and switch 354y3. This configuration enables each cell to be addressed individually. Note that if there exist N×M cells within the array, the circuit only requires (N+M) switches, as opposed to (N×M) switches. It should be appreciated that for large values of N and M, such as when N, M≈100, this makes a substantial difference how NEAT could be scaled up.

In this embodiment, MEMS switches are preferred over the use of standard electronic switches utilized in conventional digital electronics. The MEMs switches are generally preferred in this embodiment as they exhibit lower leakage currents in the off-state than those electronic switches fabricated from metal-oxide-semiconductor (MOS) transistors (i.e. fabricated using the current 0.25 µm technology), which leak current even when they are turned off. The off-state leakage current across a MOS transistor switch (source-to-drain current) is about 50 pA per 1 µm of gate length for a source-to-drain voltage $V_{ds}$≈2.2 V. Since only about 1 Volt need be applied, the leakage current drops to about 10-20 pA/µm of gate length. However, since the typical gate lengths are generally on the order of 1-10 µm, the leakage current will be 10-200 pA, which will provide a false positive signal even if the nanocapillary is not functional or addressed. Therefore, conventional electronic switches are generally not well suited for use in this embodiment, unless they can be manufactured with extremely off-state low leakage (i.e. <5 pA per 1 µm of gate length for $V_{ds}$=2.2 V). It is very beneficial for the off-state switch resistance to approach infinity (R→∞) and R<<1 GΩ in its on state. Presently, this is best achieved using a MEMS type switch configuration.

Figure 42A:
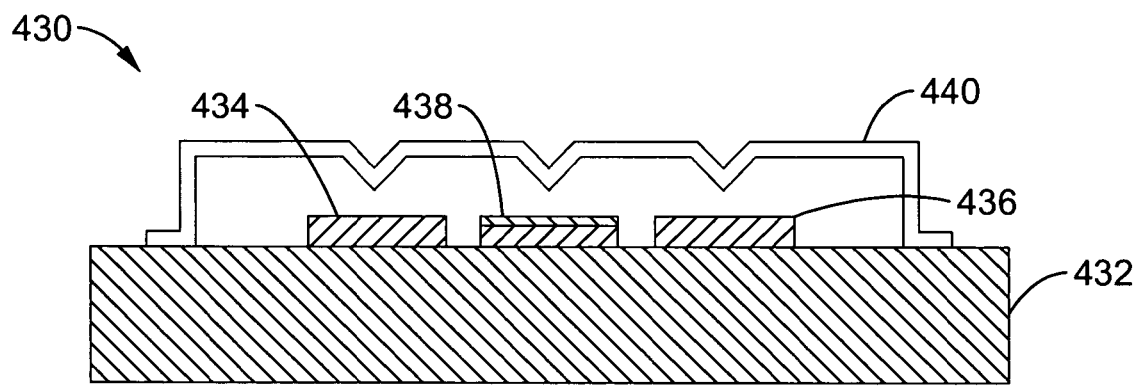
FIG. 42A-42B is a cross-section of a MEMs switch according to an aspect of the present invention, showing the connection and disconnection between lines A and B.
Figure 42B:
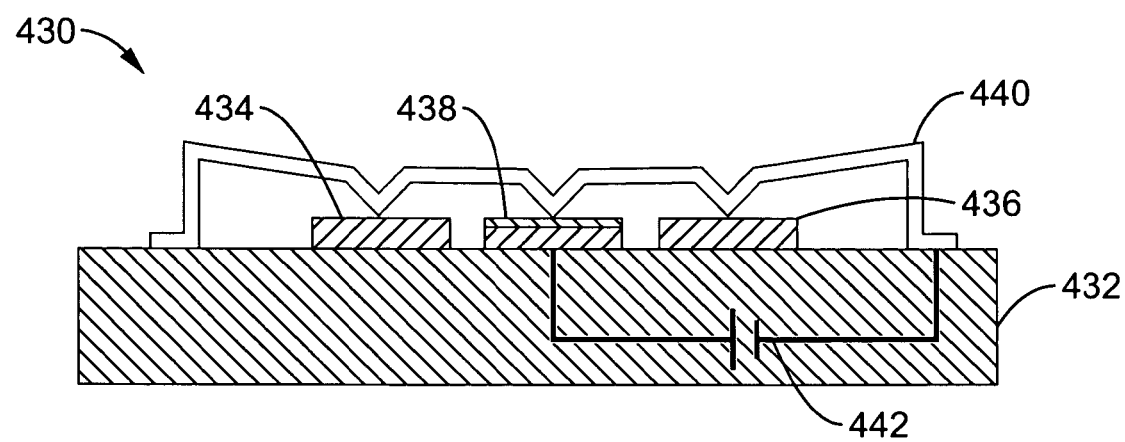

FIG. 42A and FIG. 42B illustrate an example MEMS switch 430 shown in an off-state in FIG. 42A and the on-state in FIG. 42B. A substrate 432 is configured with two separate signal contacts 434, 436 and an insulated activation electrode 438. A spring beam 440 extends above substrate 432 with an activation electrode area and separate signal contacts. In response to an activation potential 442 applied between spring beam 440 and insulated activation electrode 438, spring beam 440 is deflected toward/to activation electrode 438 wherein contacts points along the spring beam establish a connection between signal contact 434 and signal contact 436. Because no contact is established between the two electrodes A and B in the OFF state, R→∞ under DC operations. In its ON state, a bias between the Pt spring and the switching electrode (middle one) connect signal contact 434 with signal contact 436.

Figure 43A:
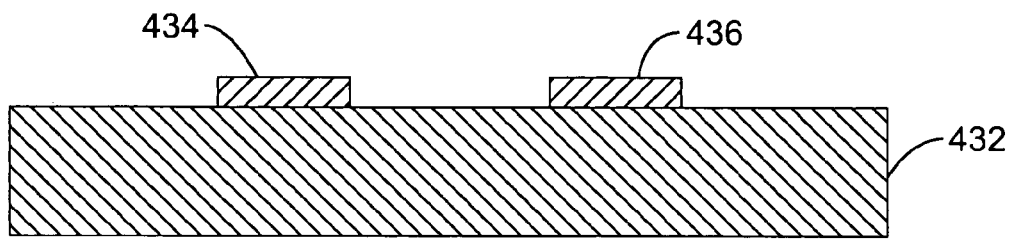
FIG. 43A-43E is a cross-section of fabricating the MEMs switch of FIG. 42A-42B.
Figure 43B:
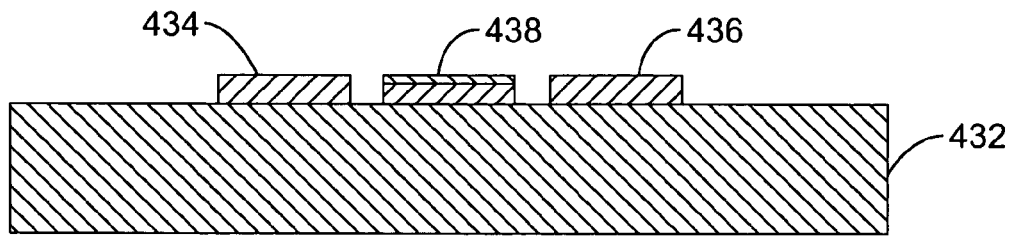
Figure 43C:
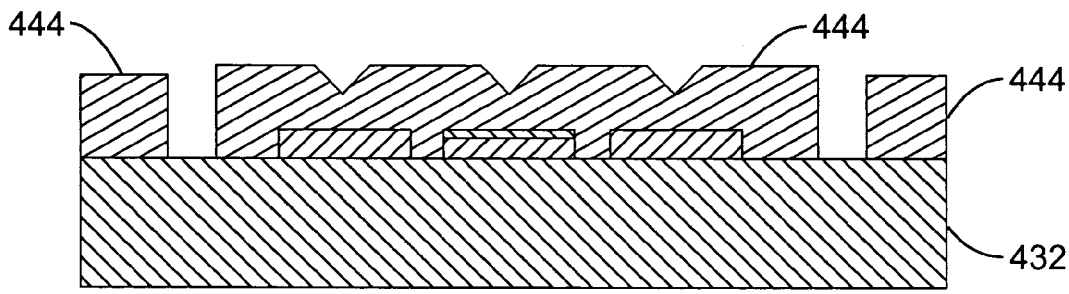
Figure 43D:
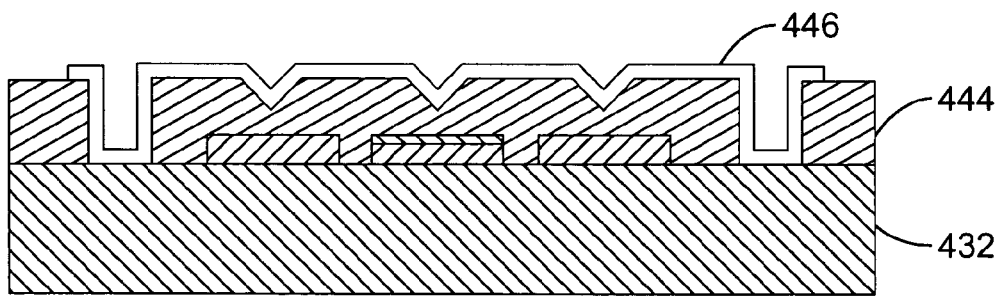
Figure 43E:
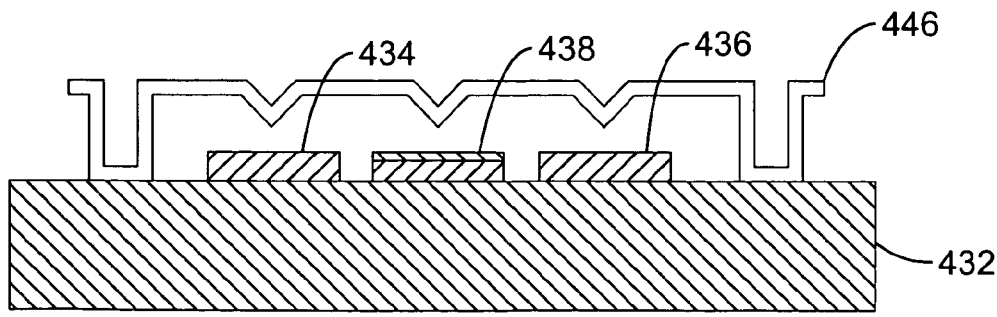

FIG. 43A through FIG. 43E depict a fabrication process for the above preferred MEMs switching device for use within the array of the present invention. In FIG. 43A a Pt film 434, 436 is deposited and patterned on substrate 432 to create a first and second signal contacts. In FIG. 43B a switching electrode 438 is deposited and patterned, and then coated with an insulating film (i.e. polymer) which is patterned as well. In FIG. 43C a sacrificial layer 444 (i.e. polymer) is deposited and etched to define the spring anchors and the contact bumps. In FIG. 43D a metallic film 446, preferably Pt, is deposited and patterned to define the spring structure. In FIG. 43E the sacrificial layer is etched and the device is dried, such as in supercritical $CO_2$, for the spring to release and allow establishing electrical contact between signal contacts 434 and 436. Note that MEMS switches can have reliability problems when the mechanical element sticks, such as due to humidity. However, by reducing contact forces, such as by introducing the small bumps or legs, this sticking problem can be overcome.

The N+M electrodes from the microfluidic and electrode wafers are wire bonded to the MEMS chip having an array of MEMs switches, which then is wire bonded to a CMOS analog amplifier chip or other form of signal processing circuit. The details of the analog amplifiers, or other forms of signal processing circuits, are not described as these functions comprise conventional technology. It should be noted that once the current (10-1000 pA) is amplified and converted to a voltage 10-1000 mV, it can be processed using digital electronics and connected to a computer for processing. This allows storage of the data from each individual channel (1', 2', 3' . . . M) such that to the user, it would appear as if the M channels were being simultaneously read out in real time.

This multiple-step integration process allows carrying out multiplexed chemical and biological sensing since the nanofluidic arrays can be functionalized selectively with different target ligands and independently addressed electrically and optically. This integrated nanofluidic chip also allows establishing an extensive nanocapillary electrophoresis database (protein, DNA, and other chemical and biological hazardous molecules) in a short timeframe for various chemical and biological sensing purposes.

Devices as Practiced

The inventive embodiments described previously have been tested and implemented in various ways as further development proceeds. FIG. 44 through FIG. 55 depict some structures and actual images of devices being practiced.

Figure 44:
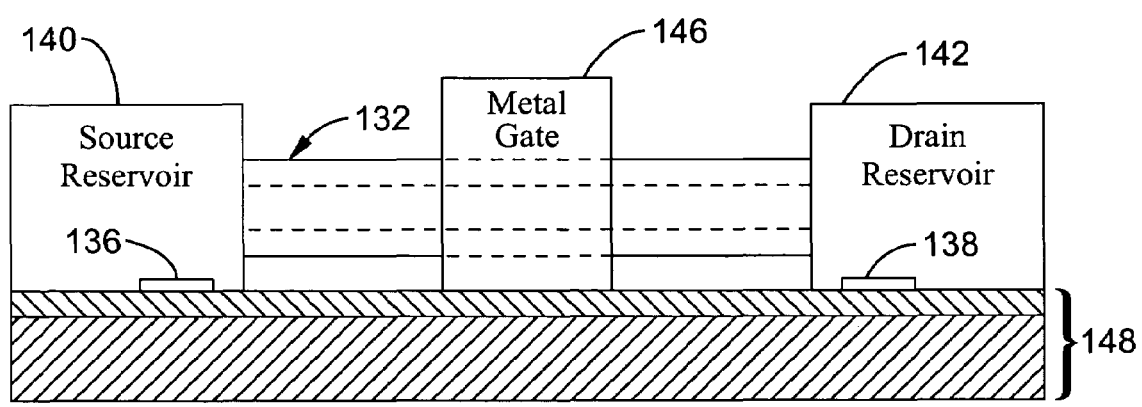
FIG. 44 is a side view of a TFET according to an embodiment of the present invention, shown fabricated on a substrate.

FIG. 44 illustrates a TFET fabricated on an insulated substrate 148, such as $SiO_2$ over Si. Although similar to FIG. 27 the metal gate 146 in this variation at least partially, and more preferably fully, surrounds a center portion of nanotube 132.

Figure 45A:
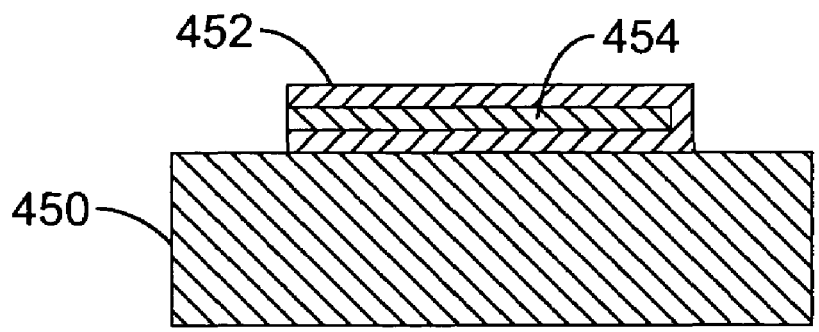
FIG. 45A-45F are cross-sections during TFET fabrication according to an aspect of the present invention.
Figure 45B:
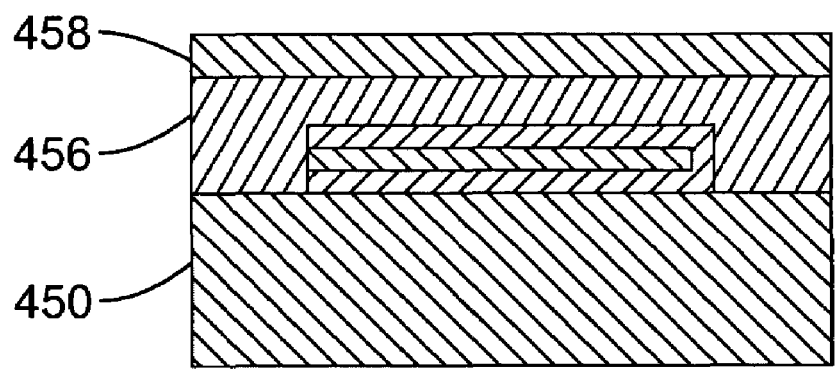
Figure 45C:
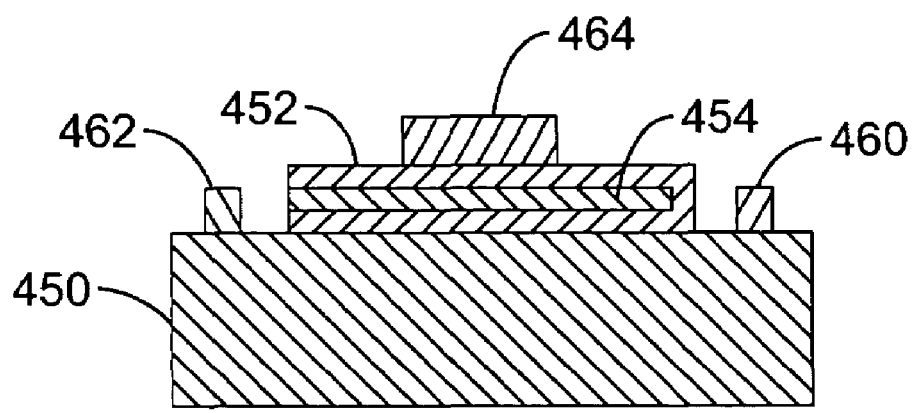
Figure 45D:
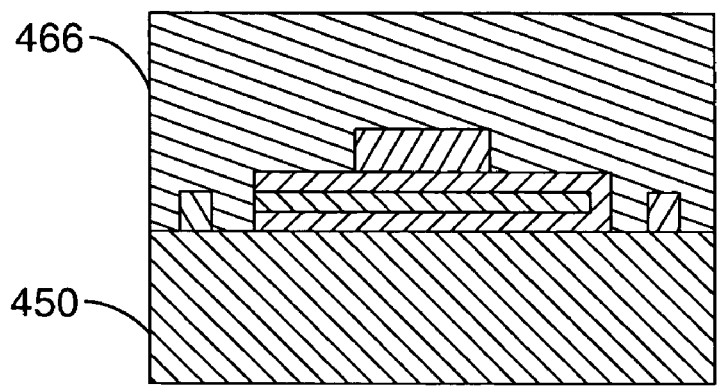
Figure 45E:
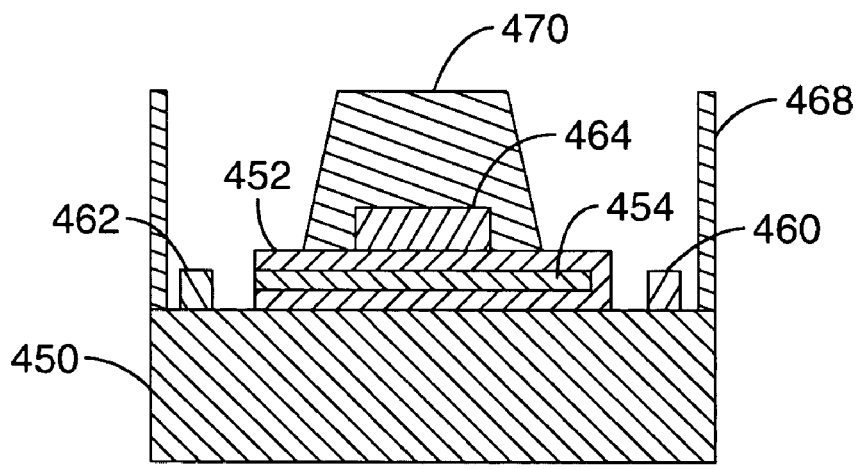
Figure 45F:
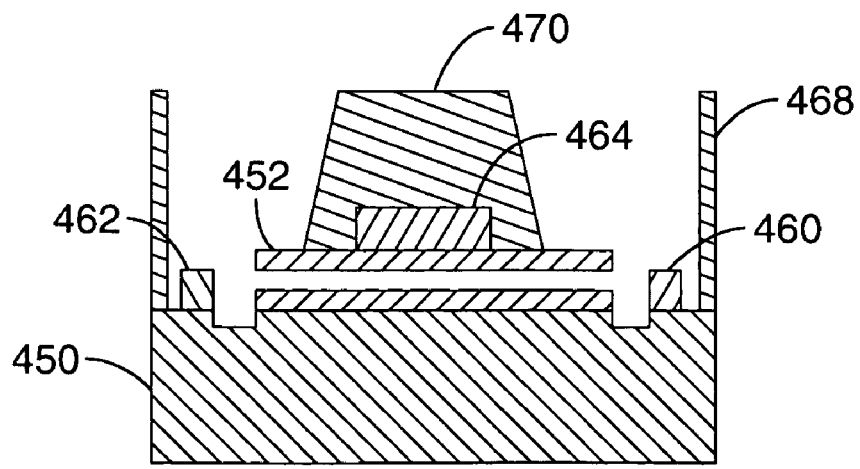

FIG. 45A-45F illustrate an embodiment of TFET fabrication with a silica nanotube. In FIG. 45A a core-shell nanowire having core 454 and shell 452, is shown lengthwise on a substrate 450, such as quartz. In FIG. 45B a metallic layer 456, such as Cr is deposited, followed by a photoresist 458. In FIG. 45C the photoresist 458 is patterned and metal 456 selectively removed, such that a drain contact 460, source contact 462, and gate contact 464 remain. In FIG. 45D a thick photoresist layer 466 is deposited. In FIG. 45E the photoresist is selectively removed leaving a raise protrusion 470 which divides the fluidic well bound by walls 468. Finally, in FIG. 45F the Si core 454 of core-sheath is removed, such as by etching, and the gated TFET device is complete, although the interior of nanotube 452 may be optionally functionalized.

Figure 46:
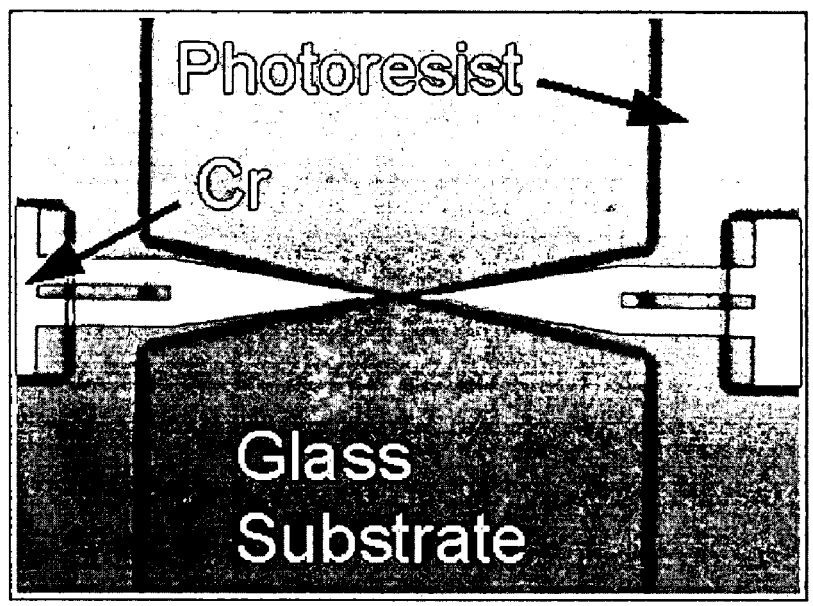
FIG. 46-55 are images from a TFET fabricated according to an embodiment of the present invention.
Figure 47:
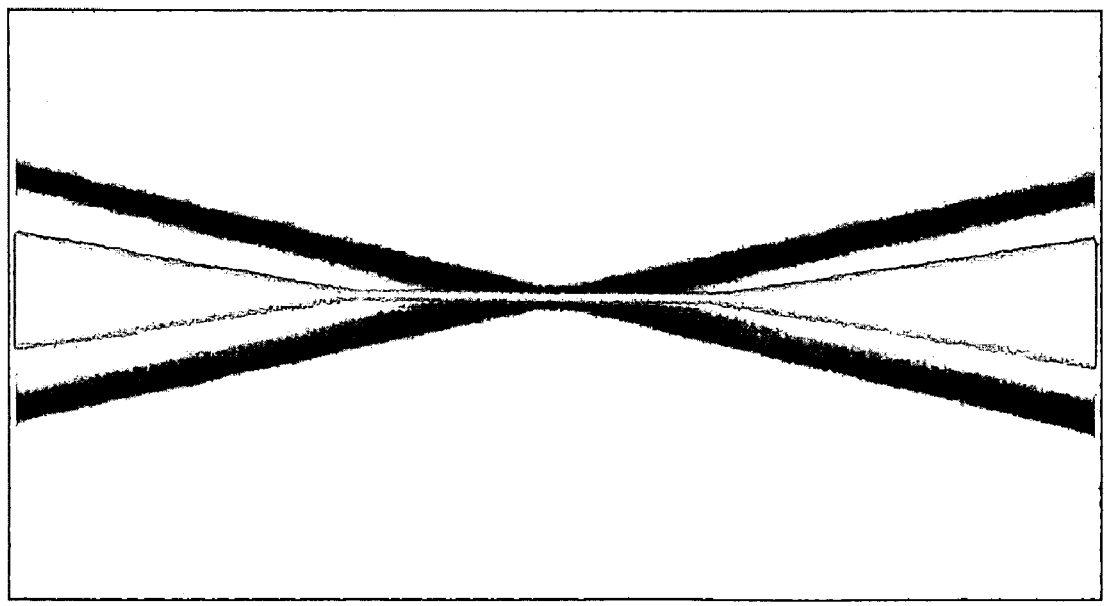
Figure 48:
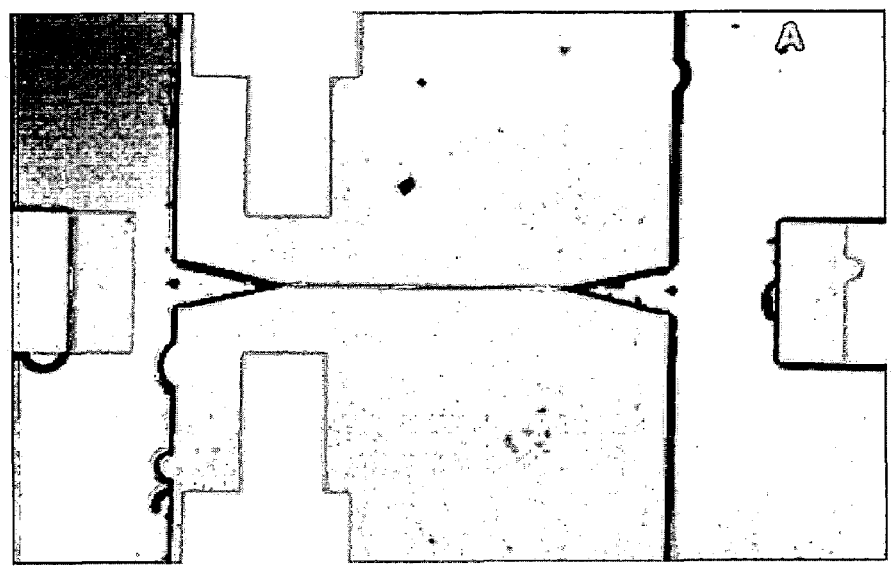
Figure 49:
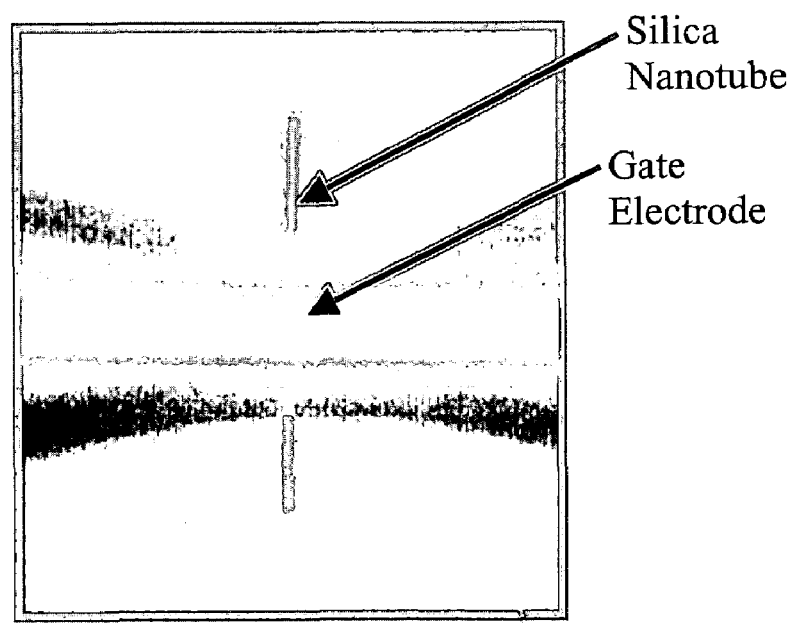
Figure 50:
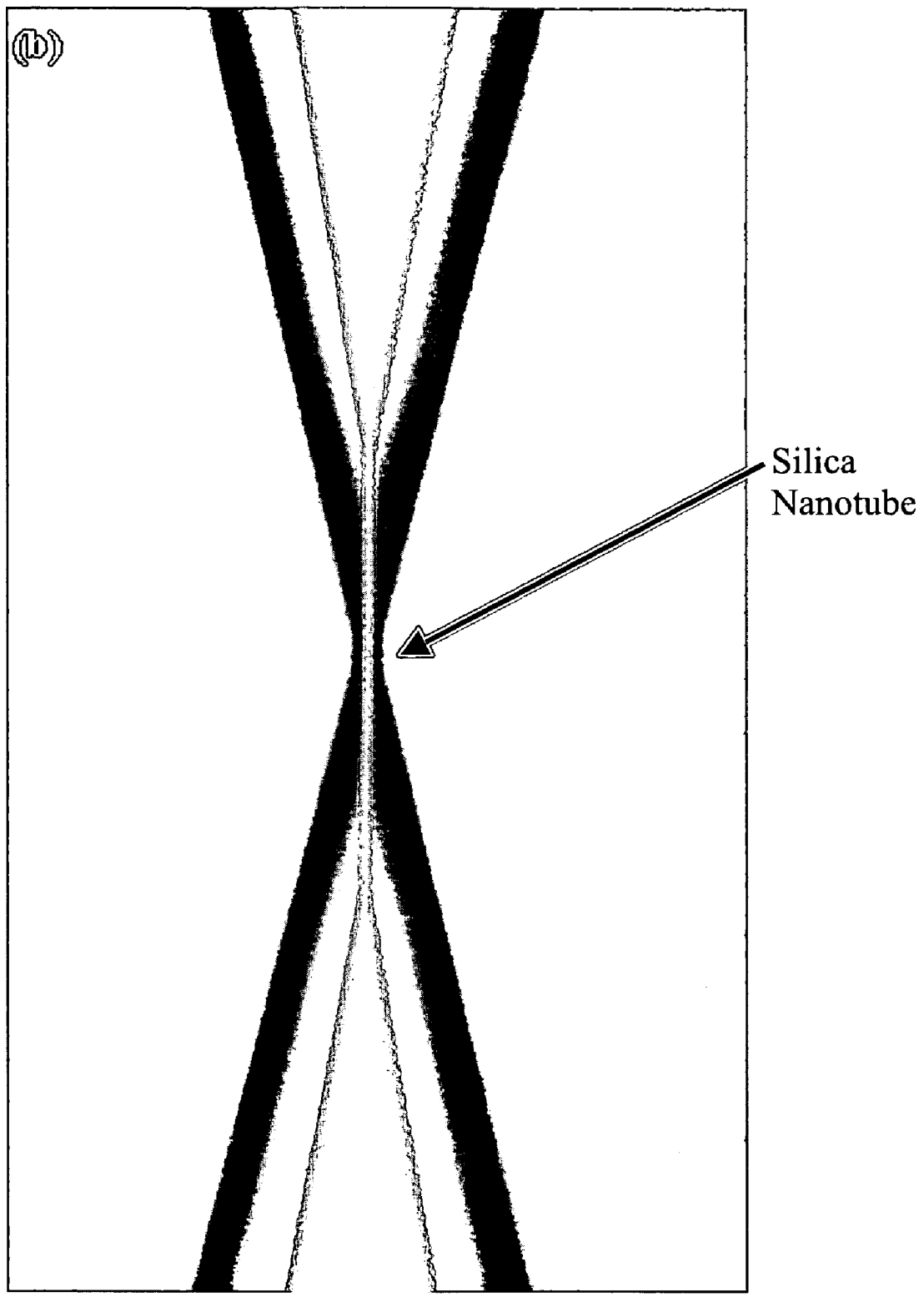
Figure 51:
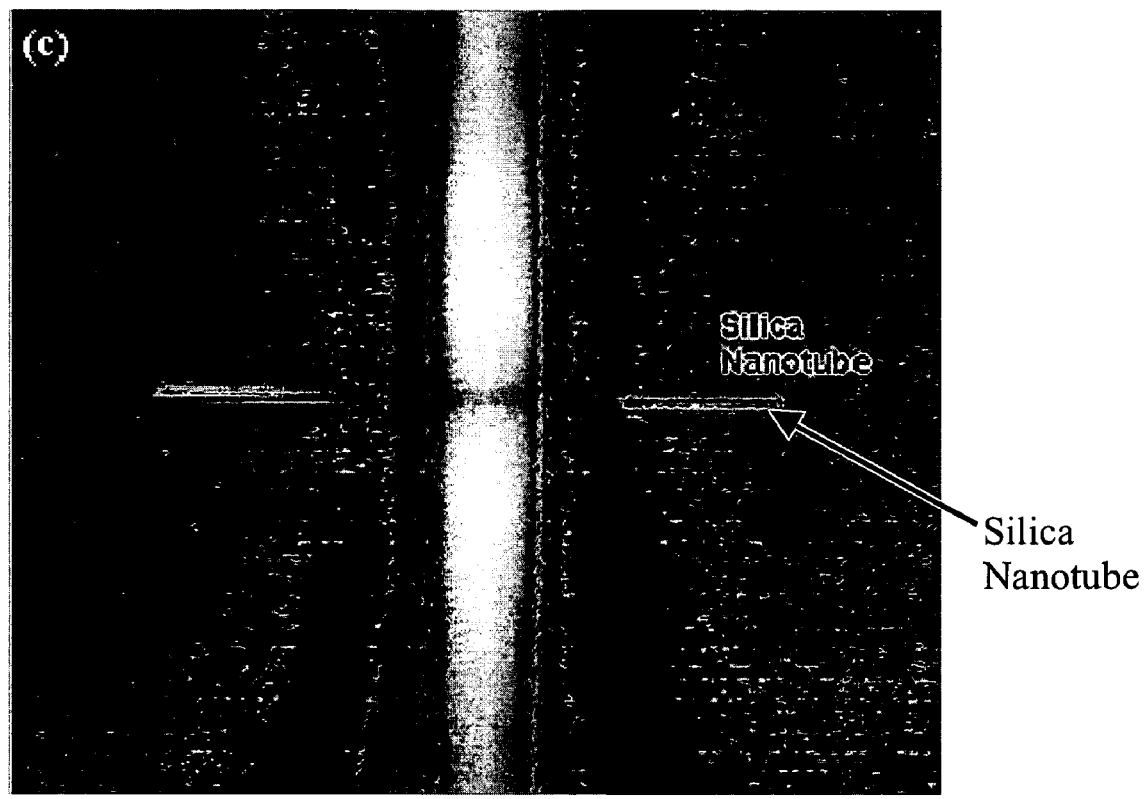
Figure 52:
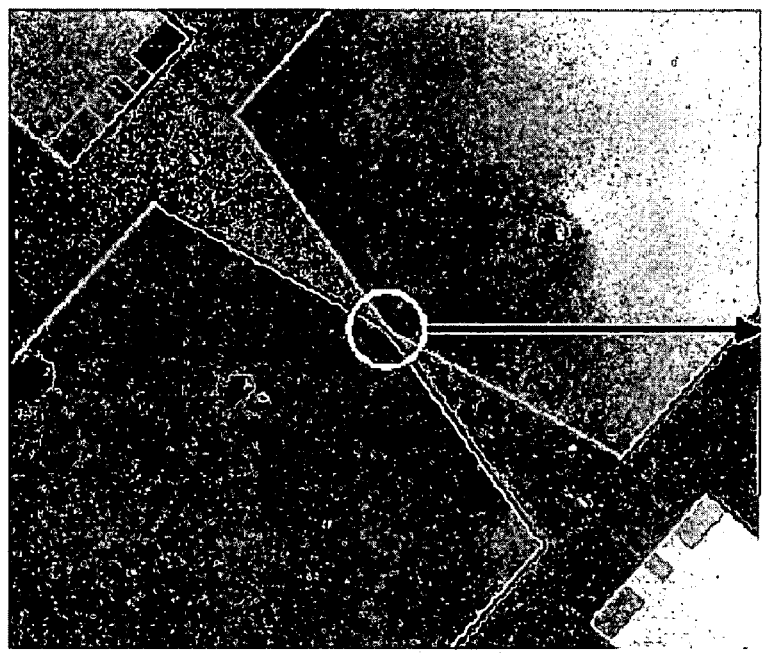

FIG. 46-55 are images from a TFET fabricated according to an embodiment of the present invention. In FIG. 46 a Cr gate on a glass substrate is shown necking down to where it crosses over the nanowire (not visible in this view). It should be appreciated that a thick photoresist covers the gate to separate an upper well from a lower well. In FIG. 47 the gate junction with the nanotube is shown slightly magnified, and the raised nature of the photoresist is slightly evident. FIG. 48 depicts metalization for the source and drain being separated along the line where the gate shown in FIG. 47 traverses, and covered with an insulating layer, such as photoresist. FIG. 49, 50 depict the silica nanotube extending between the source and drain reservoirs and covered by the gate electrode and raised photoresist material. FIG. 51 is another view of the gate and insulation over the silica nanotube. FIG. 52 depicts a less magnified view, wherein raised areas around the reservoirs are seen in relation to where the nanotube crosses between source and drain reservoirs.

Figure 53:
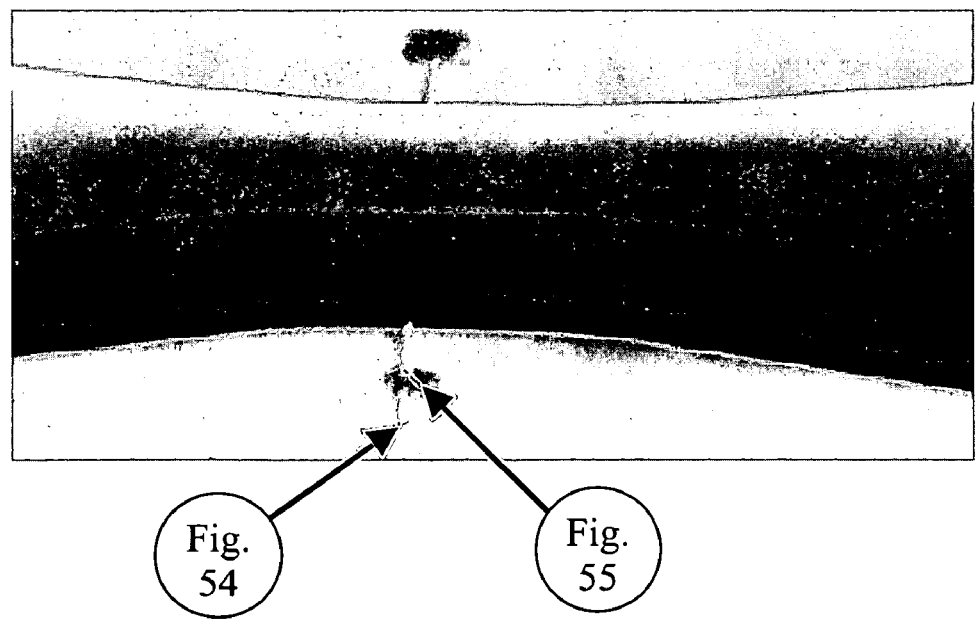
Figure 54:
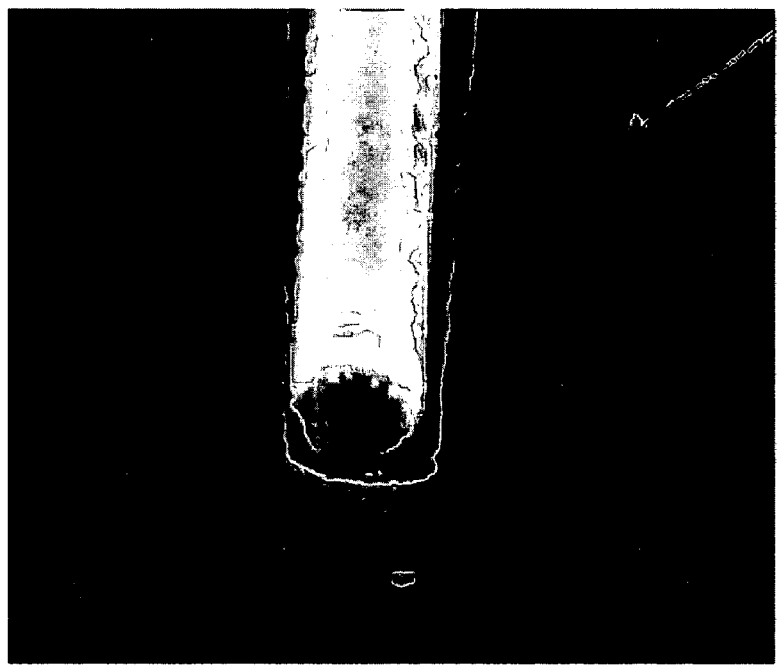

FIG. 53 depicts an off angle view of the nanotube between reservoirs and covered by the gate electrode and raised insulation. The elevated nature of the photoresist is clearly evident in this view. Near the ends of the nanotube are shown drain and source contact connections on either side of the gate. It should be appreciated that these contacts are attached towards the ends (not necessary at the ends but separated from one another along the length of the nanotube). These connections are made through a hole in the thin layer of insulation over the source and drain electrode, the nanotube being formed down against the source and drain layer and metalization overlaid to connect the nanotube to the underlying conductor. A closed end of the nanotube (prior to core removal) is shown in FIG. 54 and the connection between the nanotube and the underlying source/drain conductor is shown in FIG. 55.

Broader Impacts of Research and Benefits to Society

The present invention has demonstrated a new paradigm for chemical and biological sensing, and addresses the goals of NSF-Sensor network of developing innovative technologies to enable efficient detection and profiling of molecular changes through cross-disciplinary interactions between chemistry, engineering, semiconductor processing, statistical physics, and electronics. The NEAT/TFET devices proposes a new paradigm for molecular analysis for chemical and biological molecules. The technology provides a common sensing platform for health, environment and battlefield applications, while emphasizing high sensitivity, high specificity, cost effectiveness, and user friendliness. It is believed this new technology will enhance the availability of such technologies to civilian and homeland security purposes.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Ionic Mobilities in Bulk Water at 298 K.

| (+) Ions | Mobility ($10^{-8}$ m$^2$/s – V) | (−) Ions | Mobility ($10^{-8}$ m$^2$/s – V) |
|---|---|---|---|
| $H^+$ | 36.23 | $OH^-$ | 20.64 |
| $Na^+$ | 5.19 | $Cl^-$ | 7.91 |
| $K^+$ | 7.62 | $Br^-$ | 8.09 |
| $Zn^{2+}$ | 5.47 | $SO_4^{2-}$ | 8.29 |

What is claimed is:

1. A fluidic nanotube, comprising:
   a tubular member having first and second ends, and an inner bore between said first and second ends;
   said tubular member having a non-porous inner wall;
   said tubular member comprising a non-carbon, hydrophilic material;
   wherein said nanotube comprises a single crystalline structure.

2. A nanotube as recited in claim 1, wherein said nanotube is formed by the steps comprising:
   forming a core material;
   depositing the non-carbon, hydrophilic nanotube material over said core material; and
   removing said core material.

3. A nanotube as recited in claim 2, wherein said core material is sacrificed during said removal step.

4. A nanotube as recited in claim 2, wherein said core material comprises a sacrificial template for said nanotube.

5. A nanotube as recited in claim 2:
   wherein said core material has ends and a side surface; and
   wherein said nanotube material is deposited on said side surface to form a cylindrical sheath through which said core material extends.

6. A nanotube as recited in claim 2, wherein said core material is single-crystalline.

7. A nanotube as recited in claim 2, wherein said nanotube material is formed as an epitaxial casting over said core.

8. A nanotube as recited in claim 2, wherein said core material comprises a material selected from the group of materials consisting essentially of zinc oxide (ZnO), silicon (Si), gallium nitride (GaN), germanium (Ge), silver (Ag), gold (Au), group Il-VI materials, group Ill-V materials, elemental group IV materials, and metals.

9. A nanotube as recited in claim 2, wherein the material selected for said nanotube material has a sufficiently similar crystalline structure and lattice constant as the material selected for said core material to allow epitaxial growth of said nanotube material on said core material.

10. A nanotube as recited in claim 2, wherein said inner wall comprises a substantially uniform diameter.

11. A nanotube as recited in claim 2, wherein said is nanotube substantially isotropic.

12. A nanotube as recited in claim 2, wherein said inner wall is substantially seamless.

13. A nanotube as recited in claim 1, wherein said nanotube is a functional component of a nanodevice.

14. A nanotube as recited in claim 1, wherein said tubular member comprises multiple longitudinal segments.

15. A nanotube as recited in claim 1, wherein said inner wall is substantially continuous.

16. A nanotube as recited in claim 1, wherein said inner wall comprises a substantially uniform diameter.

17. A nanotube as recited in claim 1, wherein said nanotube is substantially isotropic.

18. A nanotube as recited in claim 1, wherein said inner wall is substantially seamless.

* * * * *